US009315818B2

(12) United States Patent
Sela et al.

(10) Patent No.: US 9,315,818 B2
(45) **Date of Patent: *Apr. 19, 2016**

(54) PLANT EXPRESSION CONSTRUCTS AND METHODS OF UTILIZING SAME

(75) Inventors: Ilan Sela, Ramot-HaShavim (IL); Rita Mozes-Koch, Yavne (IL); Yuval Peretz, Rechovot (IL); Herve Huet, Yehud (IL)

(73) Assignees: Yissum Research Development Company of the Hebrew University of Jerusalem, Jerusalem (IL); Morflora Israel Ltd., Moshav Sharsheret (IL)

( * ) Notice: Subject to any disclaimer, the term of this patent is extended or adjusted under 35 U.S.C. 154(b) by 785 days.

This patent is subject to a terminal disclaimer.

(21) Appl. No.: 12/308,121

(22) PCT Filed: Jun. 7, 2007

(86) PCT No.: PCT/IL2007/000688

§ 371 (c)(1), (2), (4) Date: Oct. 22, 2009

(87) PCT Pub. No.: WO2007/141790

PCT Pub. Date: Dec. 13, 2007

(65) Prior Publication Data

US 2010/0071088 A1 Mar. 18, 2010

Related U.S. Application Data

(60) Provisional application No. 60/811,406, filed on Jun. 7, 2006, provisional application No. 60/876,999, filed on Dec. 26, 2006.

(51) Int. Cl.
*C12N 15/82* (2006.01)

(52) U.S. Cl.
CPC ........ *C12N 15/8203* (2013.01); *C12N 15/8282* (2013.01)

(58) Field of Classification Search
USPC .......................................................... 800/279
See application file for complete search history.

(56) References Cited

U.S. PATENT DOCUMENTS

| | | | | |
|---|---|---|---|---|
| 5,981,236 A * | 11/1999 | Kridl et al. | 435/91.41 |
| 6,147,278 A | 11/2000 | Rogers et al. | |
| 6,392,121 B1 | 5/2002 | Mason et al. | |
| 8,722,966 B2 | 5/2014 | Sela et al. | |
| 2003/0079248 A1* | 4/2003 | Mason et al. | 800/280 |
| 2014/0250547 A1 | 9/2014 | Sela et al. | |

FOREIGN PATENT DOCUMENTS

| | | |
|---|---|---|
| AU | 2009269575 | 1/2010 |
| CN | 1425772 | 6/2003 |
| WO | WO 99/50429 | 10/1999 |
| WO | WO 00/20557 | 4/2000 |
| WO | WO 01/94604 | 12/2001 |
| WO | WO 2007/141790 | 12/2007 |
| WO | WO 2010/004561 | 1/2010 |

OTHER PUBLICATIONS

Varsani et al. A highly divergent South African geminivirus species illumiunates the ancient evolutionary history of this family (2009) Virol. J. 6: 36.*
Guo et al. Protein tolerance to random amino acidf change (2004) PNAS 101: 9205-9210.*
Hayes et al. Stability and expression of bacterial genes in replicating geminivirus vectors in plants (1989) Nucleic Acids Res. 17: 2391-2403.*
Andret-Link et al. Transmission specifictiy of plant viruses by vectors (2005) J. Plant Path. 87: 153-165.*
Hamilton et al. (2002) GenBank Accession No. NC_001507.1.*
Rigden et al. Plant virus DNA replication processes in Agrobacterium: insight into the origins of geminiviruses (1996) Proc. Nat. Acad. Sci. 93: 10280-10284.*
Orozco et al. Functional domains of a geminivirus replication protein (1997) J.B.C. 272: 9840-9846.*
Gleba et al Engineering viral expression vectors for plants: the full virus and the deconstructed virus strategies (2004) Curr. Opin. Plant Biol. 7: 182-188.*
Response Dated May 3, 2010 to Communication Pursuant to Article 94(3) EPC of Dec. 8, 2009 From the European Patent Office Re.: Application No. 07736428.9.
Response Dated Sep. 27, 2011 to Communication Pursuant to Article 94(3) EPC of May 19, 2011 From the European Patent Office Re.: Application No. 07736428.9.
International Preliminary Report on Patentability Dated Dec. 10, 2008 From the International Bureau of WIPO Re.: Application No. PCT/IL2007/000688.
Communication Pursuant to Article 94(3) EPC Dated Dec. 8, 2009 From the European Patent Office Re.: Application No. 07736428.9.
International Search Report and the Written Opinion Dated Jan. 17, 2008 From the International Searching Authority Re.: Application No. PCT/IL2007/000688.
International Search Report and the Written Opinion Dated Oct. 27, 2009 From the International Searching Authority Re.: Application No. PCT/IL2009/000682.
Czosnek et al. "Tomato Yellow Leaf Curl Virus, a Geminivirus With a Single Genomic Component: Molecular Analysis of Infection and New Ways for Tomato Protection", Acta Horiculturae, XP009123949, 377: 251-257, Oct. 1, 1994. p. 253, § 6, p. 255, § 3.
Kasrawi et al. "Sources of Resistance to Tomato-Yellow-Leaf-Curl-Virus (TYLCV) in Lycopersicon Species", Euphytica, XP009124008, 37(1): 61-64, Jan. 1, 1988. p. 62, col. 2, § 2.
Lapidot "Screeing for TYLCV-Resistant Plants Using Whitefly-Mediated Inoculation", Tomato Yellow Leaf Curl Virus Disease: Management, Molecular Biology, Breeding for Resistance, XP009124014, p. 329-342, Jan. 1, 2007. p. 334, § 3.

(Continued)

*Primary Examiner* — David T Fox
*Assistant Examiner* — Jared Shapiro

(57) ABSTRACT

A Geminivirus based expression construct being capable of systemic symptomeless spread in a plant host is provided as well as methods of utilizing same for plant gene expression, gene silencing and plant protection.

15 Claims, 23 Drawing Sheets

(56) References Cited

OTHER PUBLICATIONS

Petty et al. "Complementable and Noncomplementable Host Adaption Defects in Bipartite Geminiviruses", Virology, XP002550014, 212(1): 263-267, 1995. p. 263, col. 2, § 2.
Shadwick et al. "Infection, Propagation, Distribution and Stability of Plant Virus in Hairy Root Cultures", Journal of Biotechnology, XP022232036, 131(3): 318-329, Sep. 6, 2007.
Tamilselvi et al. "A Geminivirus AYVV-Derived Shuttle Vector for Tobacco BY2 Cells", Plant Cell Reports, XP002550015, 23(1-2): 81-90, Aug. 2004.
Response Dated Feb. 18, 2011 to Communication Pursuant to Article 94(3) EPC of Aug. 10, 2010 From the European Patent Office Re.: Application No. 07736428.9.
Communication Pursuant to Article 94(3) EPC Dated May 19, 2011 From the European Patent Office Re. : Application No. 07736428.9.
Response Dated Sep. 20, 2011 to Communication Pursuant to Article 94(3) EPC of May 19, 2011 From the European Patent Office Re.: Application No. 07736428.9.
International Preliminary Report on Patentability Dated Jan. 20, 2011 From the International Bureau of WIPO Re. Application No. PCT/IL2009/000682.
Communication Pursuant to Article 94(3) EPC Dated Aug. 10, 2010 From the European Patent Office Re.: Application No. 07736428.9.
Atkinson et al. "Post-Transcriptional Silencing of Chalcone Synthase in Petunia Using a Geminivirus-Based Episomal Vector", The Plant Journal, 15(5): 593-604, 1998.
Behjatnia et al. "Identification of the Replication-Associated Protein Binding Domain Within the intergenic Region of Tomato Leaf Curl Geminivirus", Nucleic Acids Research, 26(4): 925-931, 1998.
Beisson et al. "Begomovirus", Sixth ICTV Report, rf_gemini.htm.
Hong et al. "Novel System for the Simultaneous Analysis of Geminivirus DNA Replication and Plant Interactions in Nicotiana Benthamiana", Journal of Virology, 77(24): 13315-13322, 2003.
Mor et al. "Geminivirus Vectors for High-Level Expression of Foreign Proteins in Plant Cells", Biotechnology and Bioengineering, 81(4): 430-437, 2003.
Morilla et al. "A Versatile Transreplication-Based System to Identify Cellular Proteins Involved in Geminivirus Replication", Journal of Virology, 80(7): 3624-3633, 2006.
Noris et al. "Resistance to Tomato Yellow Leaf Curl Geminivirus in Nicotiana Benthamiana Plants Transformed With a Truncated Viral C1 Gene", Virology, 224: 130-138, 1996.
Padidam et al. "The Role of AV2 (Precoat) and Coat Protein in Viral Replication and Movement in Tomato Leaf Curl Geminivirus", Virology, 224: 390-404, 1996.
European Search Report and the European Search Opinion Dated Mar. 1, 2012 From the European Patent Office Re. Application No. 11009695.5.
Examination Report Dated Feb. 21, 2012 From the Instituto Mexicano de la Propriedad Industrial Re. Application No. MX/a/2011/000214 and Its Summary in English.
Communication Pursuant to Article 94(3) EPC Dated Dec. 4, 2013 From the European Patent Office Re. Application No. 09787461.4.
Inquiry of the State Examination Dated Nov. 28, 2013 From the Patent Office of the Russian Federation (ROSPATENT), Federal Institute of Industrial Property Re. Application No. 2011103072 and Its Translation Into English.
Notice of Allowance Dated Dec. 30, 2013 From the US Patent and Trademark Office Re. U.S. Appl. No. 13/003,151.
Communication Pursuant to Article 94(3) EPC Dated Jan. 3, 2013 From the European Patent Office Re. Application No. 11009695.5.
Requirement for Additional Materials Dated Jan. 19, 2014 From the State Intellectual Property Service of Ukraine, State Enterprise 'Ukrainian Institute for Industrial Property' Re. Application No. 201100882 and Its Translation Into English.
Official Action Dated Jan. 31, 2013 From the US Patent and Trademark Office Re. U.S. Appl. No. 13/003,151.
Settlage et al. "Geminivirus C3 Protein: Replication Enhancement and Protein Interactions", Journal of Virology, 79(15): 9885-9895, Aug. 2005.
Van Wezel et al. "Gene C2 of the Monopartite Geminivirus Tomato Yellow Leaf Curl Virus China Encodes a Pathogenicity Determinant That Is Localized in the Nucleus", Molecular Plant-Microbe Interactions: MPM1, 14(9): 1125-1128, 2001.
Communication Pursuant to Article 94(3) EPC Dated Feb. 17, 2014 From the European Patent Office Re. Application No. 11009695.5.
Communication Pursuant to Article 94(3) EPC Dated Feb. 19, 2013 From the European Patent Office Re. Application No. 09787461.4.
Translation of Office Action Dated Feb. 20, 2013 From the State Intellectual Property Office of the People's Republic of China Re. Application No. 200980129925.3.
Decision of Rejection Dated Apr. 1, 2014 From the State Intellectual Property Office of the People's Republic of China Re. Application No. 200980129925.3 and Its Translation Into English.
Notification of the Results of Patentability Examination Dated Apr. 11, 2014 From the Patent Office of the Russian Federation (ROSPATENT), Federal Institute of Industrial Property Re. Application No. 2011103072 and Its Translation Into English.
Patent Examination Report Dated May 12, 2014 From the Australian Government, IP Australia Re. Application No. 2009269575.
Substantive Examination Report Dated Apr. 25, 2014 From the Intellectual Property Office of the Philippines, Bureau of Patents Re. Application No. 1/2011/500032.
Communication Pursuant to Article 94(3) EPC Dated Jun. 11, 2012 From the European Patent Office Re.: Application No. 07736428.9.
Search Report and Written Opinion Dated Apr. 18, 2012 From the Intellectual Property Office of Singapore Issued by the Danish Patent and Trademark Office on Mar. 15, 2012 Re. Application No. 201100063-5.
Translation of Office Action Dated May 3, 2012 From the State Intellectual Property Office of the People's Republic of China Re. Application No. 200980129925.3.
Request for Examination Dated May 7, 2013 From the Patent Office of the Russian Federation (ROSPATENT), Federal Institute of Industrial Property Re. Application No. 2011103072 and Its Translation Into English.
Examination Report Dated Jul. 21, 2014 From the Ministry of Science and Technology, National Office of Intellectual Property of the Socialist Republic of Vietnam Re. Application No. 1-2011-00288 and Its Translation Into English.
Preliminary Decision on Refusal Dated Jul. 3, 2013 From the State intellectual Property Service of Ukraine, State Enterprise 'Ukrainian Institute for Industrial Property' Re. Application No. 201100882 and Its Translation Into English.
Subsequent Substantive Examination Report Dated Jul. 7, 2014 From the Intellectual Property Office of the Philippines, Bureau of Patents, Intellectual Property Center Re. Application No. 1/2011/500032.
Communication Pursuant to Article 94(3) EPC Dated Aug. 1, 2013 From the European Patent Office Re. Application No. 11009695.5.
Examination Report Dated Jun. 12, 2012 From the Instituto Mexicano de la Propiedad Industrial Re. Application No. MX/a/2011/000214 and Its Summary in English.
Examination Report Dated Feb. 21, 2012 From the Instituto Mexicano de la Propicdad Industrial Re. Application No. MX/a/2011/000214 and Its Summary in English.
Atkinson et al. "Post-Transcriptional Silencing of Chalcone Synthase in Petunia Using a Geminivirus-Based Episomal Vector", The Plant Journal, XP002108260, 15(5): 593-604, Sep. 1998.
Behjatnia et al. "Identification of the Replication-Associated Protein Binding Domain Within the Intergenic Region of Tomato Leaf Curl Geminivirus", Nucleic Acids Research, XP002302151, 26(4): 925-931, Feb. 15, 1998.
Hong et al. "Novel System for the Simultaneous Analysis of Geminivirus DNA Replication and Plant Interactions in Nicotiana Benthamiana", Journal of Virology, XP002462130, 77(24): 13315-13322, Dec. 2003. Fig.1.
Mor et al. "Geminivirus Vectors for High-Level Expression of Foreign Proteins in Plant Cells", Biotechnology and Bioengineering, XP002462129, 81(4): 430-437, Feb. 20, 2003. Fig.2.

(56) References Cited

OTHER PUBLICATIONS

Morilla et al. "A Versatile Transrcplication-Based System to Identify Cellular Proteins Involved in Geminivirus Replication", Journal of Virology, XP002462131, 80(7): 3624-3633, Apr. 2006. Fig.1.
Noris et al. "Resistance to Tomato Yellow Leaf Curl Geminivirus in Nicotiana Benthamiana Plants Transformed With a Truncated Viral C1 Gene", Virology, XP002142359, 224(1): 130-138, 1996.
Padidam et al. "The Role of AV2 (Precoat) and Coat Protein in Viral Replication and Movement in Tomato Leaf Curl Geminivirus", Virology, XP002177585, 224(2): 390-404, 1996.
Peretz et al. "A Universal Expression/Silencing Vector in Plants [C][OA]", Plant Physiology, XP002550013, 145(4): 1251-1263, Dec. 2007. Abstract.
Petty et al. "Complementable and Noncomplementable Host Adaption Defects in Bipartite Geminiviruses", Virology, XP002550014, 212(1): 263-267, Sep. 10, 1995. p. 263, col. 2, § 2.
Official Action Dated Aug. 28, 2013 From the US Patent and Trademark Office Re. U.S. Appl. No. 13/003,151.
Restriction Official Action Dated Sep. 6, 2912 From the US Patent and Trademark Office Re. U.S. Appl. No. 13/003,151.
Communication Pursuant to Article 94(3) EPC Dated Sep. 23, 2014 From the European Patent Office Re. Application No. 09787461.4.
Office Action Dated Sep. 30, 2013 From the State intellectual Property Office of the People's Republic of China Re. Application No. 200980129925.3 and Its Translation Into English.
Search Report Dated Oct. 10, 2012 From the Danish Patent Office on Behalf of the Intellectual Property Office of Singapore Re. Application No. 201100063-5.
Examination Report Dated Jun. 26, 2015 From the Instituto Mexicano de la Propiedad Industrial IMPI Re. Application No. MX/a/2013/002589 and Its Translation Into English.
Requisition by the Examiner Dated May 20, 2015 From the Canadian Intellectual Property Office Re. Application No. 2,730,075.

* cited by examiner

```
  1 MSKRPGDIIISTPVSKVRRRLNFDSPYSSRAAVPIVQGTNKRRSWTYRPM 50
    || ||||||||||||||||||||  |                    || |
  1 MSXRPGDIIISTPVSKVRRRLNFXGP....................YRXM 30
             .         .         .         .         .
 51 YRKPRIYRMYRSPDVPRGCEGPCKVQSYEQRDDIKHTGIVRCVSDVTRGS 100
    |||||      .   |   . | |         :    :  || ||| ||
 31 YRKPRNTECIEALMFPVDVKAPLKXSXMSNGMILSXLVLFGCVXDVTXGS 80
             .         .         .         .         .
101 GITHRVGKRFCVKSIYFLGKVWMDENIKKQNHTNQVMFFLVRDRRPYGNS 150
    ||||||||||||||||||||||||||||||||||||||||||||||||||
 81 GITHRVGKRFCVKSIYFLGKVWMDENIKKQNHTNQVMFFLVRDRRPYGNS 130
             .         .         .         .         .
151 PMDFGQVFNMFDNEPSTATVKNDLRDRFQVMRKFHATVIGGPSGMKEQAL 200
    ||||||||||||||||||||||||||||||||||||||||||||||||||
131 PMDFGQVFNMFDNEPSTATVKNDLRDRFQVMRKFHATVIGGPSGMKEQAL 180
             .         .         .         .         .
201 VKRFFKINSHVTLFIFIQEAAKYENHTENALLLYMACTHASNPVYATMKI 250
    ||||||||||||     |||||||||||||||||||||||||||||||||
181 VKRFFKINSHVT..YNHQEAAKYENHTENALLLYMACTHASNPVYATMKI 228
             .
251 RIYFYDSISN 260
    ||||||||||
229 RIYFYDSISN 238
```

Fig. 1c

```
  1 GTTGAAATGAATCGGTGTCTCTCAAAGCTCTATGGCAATCGGTGTATCGG  50
    ||||||||||||||||||| ||||||||||||||||||||||||||||||
  1 gttgaaatgaatcggtgtccctcaaagctctatggcaatcggtgtatcgg  50

 51 TGTCTTACTTATACCTGGACACCTAATGGCTATTTGGTAATTTCATAAAT 100
    ||||||||||||| ||||||||||||||||||||||||||||||||||||
 51 tgtcttacttatacttggacacctaatggctatttggtaatttcataaat 100

101 GTTCATTGCAATTCAAAATTCAAAATTCAAAAATCAAATCTTTAAAGCGG 150
    ||||||| |||||||||||||||||||||||||||||| |||||||||||
101 gttcatttcaattcaaaattcaaaattcaaaaatcaaatcattaaagcgg 150

151 CCATCCGTATAATATTACCGGATGGCCGCGCCTTTTGTTTTTATGTGGTC 200
    |||||||||||||||||||||||||||||||||||||| |||||||||||
151 ccatccgtataatattaccggatggccgcgccttttccttttatgtggtc 200

201 CCCACGAGGGTTACACAGACGTCACTGTCAACCAATCAAATTGCATTCTC 250
    |||||||||||||||||||| || | |||||||||||||||||||||||
201 cccacgagggttacacagatgttattgtcaaccaatcaaattgcattctc 250

251 AAACGTTAGATAAGTGTTCATTTGTCTTTATATACTTGGTCCCCAAGTTT 300
    ||||||||||||||||||||||||||||||||||||||||||||||||||
251 aaacgttagataagtgttcatttgtctttatatacttggtccccaagttt 300

301 TTTGTCTTGCAATATGTGGGACCCACTTCTTAATGAATTTCCTGAATCTG 350
    ||||||||||||||||||||||||||||||||||||||||||||||||||
301 tttgtcttgcaatatgtgggacccacttcttaatgaatttcctgaatctg 350

351 TTCACGGATTTCGTTGTATGTTAGCTATTAAATATTTGCAGTCCGTTGAG 400
    ||||||||||||||||||||||||||||||||||||||||||||||||||
351 ttcacggatttcgttgtatgttagctattaaatatttgcagtccgttgag 400

401 GAAACTTACGAGCCCAATACATTGGGCCACGATTTAATTAGGGATCTTAT 450
    ||||||||||||||||||||||||||||||||||||||||||||||||||
401 gaaacttacgagcccaatacattgggccacgatttaattagggatcttat 450

451 ATCTGTTGTAAGGGCCCCGTGACTATGTCGAAGCGACCAGGCGATATAAT 500
    |||||||||||||||| |||||||||||||||||||||||||||||||||
451 atctgttgtaaggg.cccgtgactatgtcgaagcgaccaggcgatataat 499

501 CATTTCCACGCCCGTCTCGAAGGTTCGCCGAAGGCTGAACTTCGACGGCC 550
    |||||||||||||||||||||||||||||||||||||||||||||| |||
500 catttccacgcccgtctcgaaggttcgccgaaggctgaacttcgacagcc 549

551 CA................................................ 552
    ||
550 catacagcagccgtgctgctgtccccattgtccaaggcacaaacaagcga 599

553 ...........TACAGGCCCATGTACCGAAAGCCCAGAA.ATACAGAAT 589
               ||||||||||||||||||||||||||||| |||||||||
600 cgatcatggacgtacaggcccatgtaccgaaagcccagaatatacagaat 649

590 GTATCGAAGCCCTGATGTTCCCCGTGGATGTGAAGGCCCCTTTAAAGTCC 639
    ||||||||||||||||||||||||||||||||||||||||| ||||||||
650 gtatcgaagccctgatgttccccgtggatgtgaaggcccatgtaaagtcc 699

640 AGTCTTATGAGCAACGGGATGATATTAAGCATCCTGGTATTGTTCGGTTG 689
    |||||||||||||||||||||||||||||||| ||||||||||| ||||
700 agtcttatgagcaacgggatgatattaagcatactggtattgttc.gttg 748
```

Fig. 1d

```
 690 TGTTAGTGATGTTACTCGTGGATCTGGAATTACTCACAGAGTGGGTAAGA  739
     ||||||||||||||||||||||||||||||||||||||||||||||||||
 749 tgttagtgatgttactcgtggatctggaattactcacagagtgggtaaga  798

 740 GGTTCTGTGTTAAATCGATATATTTTTTAGGTAAAGTCTGGATGGATGAA  789
     ||||||||||||||||||||||||||||||||||||||||||||||||||
 799 ggttctgtgttaaatcgatatattttttaggtaaagtctggatggatgaa  848

 790 AATATCAAGAAGCAGAATCACACTAATCAGGTCATGTTCTTCTTGGTCCG  839
     ||||||||||||||||||||||||||||||||||||||||||||||||||
 849 aatatcaagaagcagaatcacactaatcaggtcatgttcttcttggtccg  898

 840 TGATAGAAGGCCCTATGGAAACAGCCCAATGGATTTTGGACAGGTTTTTA  889
     ||||||||||||||||||||||||||||||||||||||||||||||||||
 899 tgatagaaggccctatggaaacagcccaatggattttggacaggttttta  948

 890 ATATGTTCGATAATGAGCCCAGTACCGCAACCGTGAAGAATGATTTGCGT  939
     ||||||||||||||||||||||||||||||||||||||||||||||||||
 949 atatgttcgataatgagcccagtaccgcaaccgtgaagaatgatttgcgt  998

 940 GATAGGTTTCAAGTGATGAGGAAATTTCATGCTACAGTTATTGGTGGGCC  989
     ||||||||||||||||||||||||||||||||||||||||||||||||||
 999 gataggtttcaagtgatgaggaaatttcatgctacagttattggtgggcc  1048

 990 CTCTGGAATGAAGGAACAGGCATTAGTTAAGAGATTTTTTAAAATTAACA  1039
     ||||||||||||||||||||||||||||||||||||||||||||||||||
1049 ctctggaatgaaggaacaggcattagttaagagatttttaaaattaaca   1098

1040 GTCATGTAACTTATAAT......CATCAGGAGGCAGCAAAGTACGAGAAC  1083
     ||||||||||||    |      ||||||||||||||||||||||||||
1099 gtcatgtaactttatttatattcattcaggaggcagcaaagtacgagaac  1148

1084 CATACTGAAAACGCCTTGTTATTGTATATGGCATGTACGCATGCCTCTAA  1133
     ||||||||||||||||||||||||||||||||||||||||||||||||||
1149 catactgaaaacgccttgttattgtatatggcatgtacgcatgcctctaa  1198

1134 TCCAGTGTATGCAACTATGAAAATACGCATCTATTTCTATGATTCAATAT  1183
     ||||||||||||||||||||||||||||||||||||||||||||||||||
1199 tccagtgtatgcaactatgaaaatacgcatctatttctatgattcaatat  1248

1184 CAAATTAATAAAATTTATATTTTATATCATGAGTTTCTGTTACATTTATT  1233
     ||||||||||||||||||||||||||||||||||||||||||||||||||
1249 caaattaataaaatttatattttatatcatgagtttctgttacatttatt  1298

1234 GTGTTTTCAAGTACATCATACAATACATGATCAACTGCTCTGATTACATT  1283
     ||||||||||||||||||||||||||||||||||||||||||||||||||
1299 gtgttttcaagtacatcatacaatacatgatcaactgctctgattacatt  1348

1284 GTTAATGGAAATTACACCAAGACTATCTAAATACTTAAGAACTTCATATC  1333
     ||||||||||||||||||||||||||||||||||||||||||||||||||
1349 gttaatggaaattacaccaagactatctaaatacttaagaacttcatatc  1398

1334 TAAATACTCTTAAGAAATGACCAGTCTGAGGCTGTAATGTCGTCCAAATT  1383
     ||||||||||||||||||||||||||||||||||||||||||||||||||
1399 taaatactcttaagaaatgaccagtctgaggctgtaatgtcgtccaaatt  1448

1384 CGGAAGTTGAGAAAACATTTGTGAATCCCCATTACCTTCCTGATGTTGTG  1433
     |||||||  |||||||||||||||||||||||||||||||||||||||||
1449 cggaagtcgagaaaacatttgtgaatccccattaccttcctgatgttgtg  1498
```

Fig. 1d (Cont.)

```
1434 GTTGAATCTTATCTGAATGGAAATGATGTCGTGGTTCATTAGAAATGGCC 1483
     ||||||||||||||||||||||||||||||||||||||||||||||||||
1499 gttgaatcttatctgaatggaaatgatgtcgtggttcattagaaatggcc 1548
              .         .         .         .         .
1484 TCTGGCTGTGTTCTGTTATCTTGAAATAGAGGGGGATTGTTATCTCCCAG 1533
     ||||||||||||||||||||||||||||||||||  |  |||||||||||
1549 tctggctgtgttctgttatcttgaaatagaggggattgtttatctcccag 1598
              .         .         .         .         .
1534 ATAAAAACGCCATTCTCTGCCTGAGGAGCAGTGATGAGTTCCCCTGTGCG 1583
     ||||||||||||||||||||||||||||||||||||||||||||||||||
1599 ataaaaacgccattctctgcctgaggagcagtgatgagttcccctgtgcg 1648
              .         .         .         .         .
1584 TGAATCCATGATTATTGCAGTTGAGGTGGAGGTAGTATGAGCAGCCACAG 1633
     ||||||||||||||||||||||||||||||||||||||||||||||||||
1649 tgaatccatgattattgcagttgaggtggaggtagtatgagcagccacag 1698
              .         .         .         .         .
1634 TCTAGGTCTACACGCTTACGCCTTATTGGTTTCTTCTTGGCTATCTTGTG 1683
     ||||||||||||||||||||||||||||||||||||||||||||||||||
1699 tctaggtctacacgcttacgccttattggtttcttcttggctatcttgtg 1748
              .         .         .         .         .
1684 TTGGACCTTGATTGATACTTGCGAACAGTGGCTCGTAGAGGGTGACGAAG 1733
     ||||||||||||||||||||||||||||||||||||||||||||||||||
1749 ttggaccttgattgatacttgcgaacagtggctcgtagagggtgacgaag 1798
              .         .         .         .         .
1734 GTTGCATTCTTGAGAGCCCAATTTTTCAAGGATATGTTTTTTTCTTCGTC 1783
     ||||||||||||||||||||||||||||||||||||||||||||||||||
1799 gttgcattcttgagagcccaatttttcaaggatatgtttttttcttcgtc 1848
              .         .         .         .         .
1784 TAGATATTCCCTATATGATGAGGTAGGTCCTGGATTGCAGAGGAAGATAG 1833
     |||||||||||||||||| |||||||||||||||||||||||||||||||
1849 tagatattccctatatgaggaggtaggtcctggattgcagaggaagatag 1898
              .         .         .         .         .
1834 TGGGAATTCCCCCTTTAATTTGAATGGGCTTCCCGTACTTTGTGTTGCTT 1883
     ||||||||||||||||||||||||||||||||||||||||||||||||||
1899 tgggaattccccctttaatttgaatgggcttcccgtactttgtgttgctt 1948
              .         .         .         .         .
1884 TGCCAGTCCCTCTGGGCCCCCATGAATTCCTTGAAGTGCTTTAAATAATG 1933
     ||||||||||||||||||||||||||||||||||||||||||||||||||
1949 tgccagtccctctgggcccccatgaattccttgaagtgctttaaataatg 1998
              .         .         .         .         .
1934 CGGGTCTACGTCATCAATGACGTTGTACCACGCATCATTACTGTACACCT 1983
     ||||||||||||||||||||||||||||||||||||||||||||||||||
1999 cgggtctacgtcatcaatgacgttgtaccacgcatcattactgtacacct 2048
              .         .         .         .         .
1984 TTGGGCTTAGGTCTAGATGTCCACATAAATAATTATGTGGGCCTAGAGAC 2033
     ||||||||||||||||||||||||||||||||||||||||||||||||||
2049 ttgggcttaggtctagatgtccacataaataattatgtgggcctagagac 2098
              .         .         .         .         .
2034 CTGGCCCACATTGTTTTGCCTGTTCTGCTATCACCCTCAATGACAATACT 2083
     ||||||||||||||||||||||||||||||||||||||||||||||||||
2099 ctggcccacattgttttgcctgttctgctatcaccctcaatgacaatact 2148
              .         .         .         .         .
2084 TATGGGTCTCCATGGCCGCGCAGCGGAATACACGACGTTCTCGGCGACCC 2133
     ||||||||||||||||||||||||||||||||||||||||||||||||||
2149 tatgggtctccatggccgcgcagcggaatacacgacgttctcggcgaccc 2198
```

Fig. 1d (Cont.)

```
2134 ACTCTTCAAGTTCATCTGGAACTTGATTAAAAGAAGAAGAAAGAAATGGA 2183
     ||||||||||||||||||||||||||||||||||||||||||||||||||
2199 actcttcaagttcatctggaacttgattaaaagaagaagaaagaaatgga 2248
              .         .         .         .         .
2184 GAAACATAAACTTCTAAAGGAGGACTAAAAATCCTATCTAAATTTGAACT 2233
     ||||||||||||||||||||||||||||||||||||||||||||||||||
2249 gaaacataaacttctaaaggaggactaaaaatcctatctaaatttgaact 2298
              .         .         .         .         .
2234 TAAATTATGAAATTGTAAAATATAGTCCTTTGGGGCCTTCTCTTTTAATA 2283
     ||||||||||||||||||||||||||||||||||||||||||||||||||
2299 taaattatgaaattgtaaaatatagtcctttggggccttctcttttaata 2348
              .         .         .         .         .
2284 TATTGAGGGCCTCGGATTTACTGCCTGAATTGAGTGCTTCGGCATATGCG 2333
     ||||||||||||||||||||||||||||||||||||||||||||||||||
2349 tattgagggcctcggatttactgcctgaattgagtgcttcggcatatgcg 2398
              .         .         .         .         .
2334 TCGTTGGCAGATTGCTGACCTCCTCTAGCTGATCTGCCATCGATTTGGAA 2383
     |||||||||||||||||||||||||||||||||||||||||||||||| |
2399 tcgttggcagattgctgacctcctctagctgatctgccatcgatttggga 2448
              .         .         .         .         .
2384 AACTCCAAAATCAATGAAGTCTCCGTCTTTCTCCACGTAGGTCTTGACAT 2433
     |||||||||||||||||||| |||||||||||||||||||||||||||||
2449 aactccaaaatcaatgaagtttccgtctttctccacgtaggtcttgacat 2498
              .         .         .         .         .
2434 CTGTTGAGCTCTTAGCTGCCTGAATGTTCGGATGGAAATGTGCTGACCTG 2483
     ||||||||||||||||||||||||||||||||||||||||||||||||||
2499 ctgttgagctcttagctgcctgaatgttcggatggaaatgtgctgacctg 2548
              .         .         .         .         .
2484 TTTGGTGATACCAGGTCGAAGAACCGTTGGTTCTTACATTGGTATTTGCC 2533
     ||||| ||||||| ||||||||||||||||||||||||||||||||||||
2549 tttggggataccaagtcgaagaaccgttggttcttacattggtatttgcc 2598
              .         .         .         .         .
2534 TTCGAATTGGATAAGCACATGGAGATGTGGTTCCCCATTCTCGTGGAGTT 2583
     ||||||||||||||||||||||||||||||||||||||||||||||||||
2599 ttcgaattggataagcacatggagatgtggttccccattctcgtggagtt 2648
              .         .         .         .         .
2584 CTCTGCAAACTTTGATGTATTTTTTATTTGTTGGGGTTTCTAGGTTTTTT 2633
     || |||||||||||||||||||||||||||||||||||||||| ||||||
2649 ctttgcaaactttgatgtattttttatttgttggggtttctagttttttt 2698
              .         .         .         .         .
2634 AATTGGGAAAGTGCTTCCTCTTTAGAGAGAGAACAATTGGGATATGTTAG 2683
     ||||||||||||||||||||||||||||||||||||||||||||||||||
2699 aattgggaaagtgcttcctctttagagagagaacaattgggatatgttag 2748
              .         .         .
2684 GAAATAATTTTTGGCATATATTTTAAATAAACGAGGCAT 2722
     |||||||||||||||||||||||||||||||||||||||
2749 gaaataatttttggcatatattttaaataaacgaggcat 2787
```

Fig. 1d (Cont.)

Fig. 5a
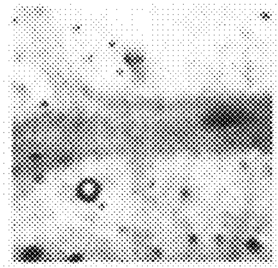
Fig. 5b
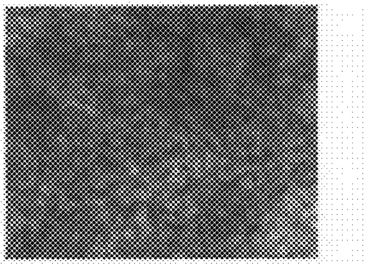
Fig. 5c
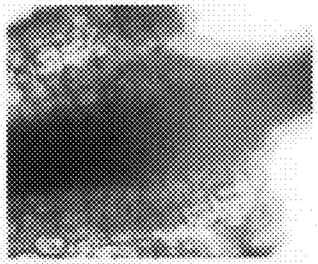
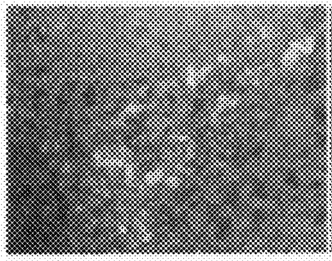
Fig. 5d
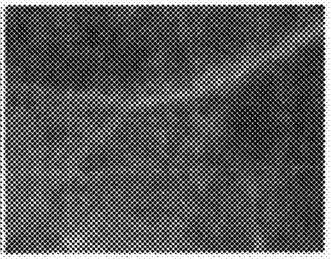
Fig. 5e
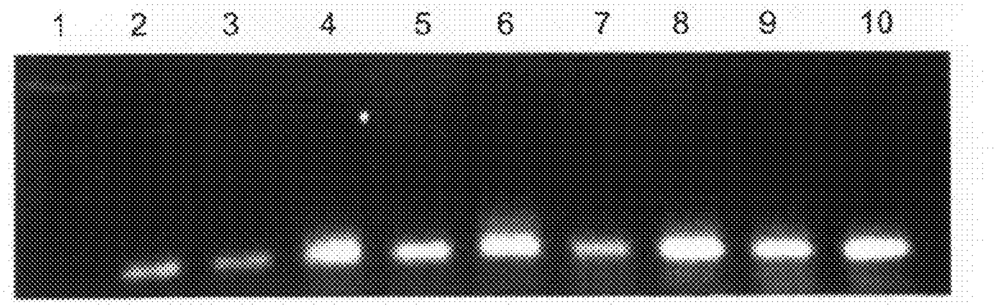
Fig. 6

SEQUENCE LISTING

```
<160> NUMBER OF SEQ ID NOS: 52

<210> SEQ ID NO 1
<211> LENGTH: 5509
<212> TYPE: DNA
<213> ORGANISM: Artificial sequence
<220> FEATURE:
<223> OTHER INFORMATION: IL-60-BS

<400> SEQUENCE: 1

gttgaaatga atcggtgtct ctcaaagctc tatggcaatc ggtgtatcgg tgtcttactt     60

atacctggac acctaatggc tatttggtaa tttcataaat gttcattgca attcaaaatt    120

caaaattcaa aaatcaaatc tttaaagcgg ccatccgtat aatattaccg gatggccgcg    180

ccttttgttt ttatgtggtc cccacgaggg ttacacagac gtcactgtca accaatcaaa    240

ttgcattctc aaacgttaga taagtgttca tttgtcttta tatacttggt ccccaagttt    300

tttgtcttgc aatatgtggg acccacttct taatgaattt cctgaatctg ttcacggatt    360

tcgttgtatg ttagctatta aatatttgca gtccgttgag gaaacttacg agcccaatac    420

attgggccac gatttaatta gggatcttat atctgttgta agggccccgt gactatgtcg    480

aagcgaccag gcgatataat catttccacg cccgtctcga aggttcgccg aaggctgaac    540

ttcgacggcc catacaggcc catgtaccga aagcccagaa atacagaatg tatcgaagcc    600

ctgatgttcc ccgtggatgt gaaggcccct ttaaagtcca gtcttatgag caacgggatg    660

atattaagca tcctggtatt gttcggttgt gttagtgatg ttactcgtgg atctggaatt    720

actcacagag tgggtaagag gttctgtgtt aaatcgatat attttttagg taaagtctgg    780

atggatgaaa atatcaagaa gcagaatcac actaatcagg tcatgttctt cttggtccgt    840

gatagaaggc cctatggaaa cagcccaatg gattttggac aggtttttaa tatgttcgat    900

aatgagccca gtaccgcaac cgtgaagaat gatttgcgtg ataggtttca agtgatgagg    960

aaatttcatg ctacagttat tggtgggccc tctggaatga aggaacaggc attagttaag   1020

agatttttta aaattaacag tcatgtaact tataatcatc aggaggcagc aaagtacgag   1080

aaccatactg aaaacgcctt gttattgtat atggcatgta cgcatgcctc taatccagtg   1140

tatgcaacta tgaaaatacg catctatttc tatgattcaa tatcaaatta ataaaattta   1200

tattttatat catgagtttc tgttacattt attgtgtttt caagtacatc atacaataca   1260

tgatcaactg ctctgattac attgttaatg gaaattacac caagactatc taaatactta   1320

agaacttcat atctaaatac tcttaagaaa tgaccagtct gaggctgtaa tgtcgtccaa   1380

attcggaagt tgagaaaaca tttgtgaatc cccattacct tcctgatgtt gtggttgaat   1440

cttatctgaa tggaaatgat gtcgtggttc attagaaatg gcctctggct gtgttctgtt   1500

atcttgaaat agagggggat tgttatctcc cagataaaaa cgccattctc tgcctgagga   1560

gcagtgatga gttcccctgt gcgtgaatcc atgattattg cagttgaggt ggaggtagta   1620
```

-continued

```
tgagcagcca cagtctaggt ctacacgctt acgccttatt ggtttcttct tggctatctt   1680

gtgttggacc ttgattgata cttgcgaaca gtggctcgta gagggtgacg aaggttgcat   1740

tcttgagagc ccaatttttc aaggatatgt ttttttcttc gtctagatat tccctatatg   1800

atgaggtagg tcctggattg cagaggaaga tagtgggaat tccccccttta atttgaatgg   1860

gcttcccgta ctttgtgttg ctttgccagt ccctctgggc cccatgaat tccttgaagt   1920

gctttaaata atgcgggtct acgtcatcaa tgacgttgta ccacgcatca ttactgtaca   1980

cctttgggct taggtctaga tgtccacata aataattatg tgggcctaga gacctggccc   2040

acattgtttt gcctgttctg ctatcaccct caatgacaat acttatgggt ctccatggcc   2100

gcgcagcgga atacacgacg ttctcggcga cccactcttc aagttcatct ggaacttgat   2160

taaaagaaga agaaagaaat ggagaaacat aaacttctaa aggaggacta aaaatcctat   2220

ctaaatttga acttaaatta tgaaattgta aaatatagtc ctttggggcc ttctctttta   2280

atatattgag ggcctcggat ttactgcctg aattgagtgc ttcggcatat gcgtcgttgg   2340

cagattgctg acctcctcta gctgatctgc catcgatttg gaaaactcca aaatcaatga   2400

agtctccgtc tttctccacg taggtcttga catctgttga gctcttagct gcctgaatgt   2460

tcggatggaa atgtgctgac ctgtttgggg ataccaagtc gaagaaccgt tggttcttac   2520

attggtattt gccttcgaat tggataagca catggagatg tggttcccca ttctcgtgga   2580

gttctttgca aactttgatg tatttttat ttgttggggt ttctagtttt tttaattggg   2640

aaagtgcttc ctctttagag agagaacaat tgggatatgt taggaaataa tttttggcat   2700

atattttaaa taaacgaggc atgttgaaat gaatcggtgt ccctcaaagc tctatggcaa   2760

tcggtgtatc ggtgtcttac ttatacttgg acacctaatg gctatttggt aatttcataa   2820

atgttcattt caattcaaaa ttcaaaattc aaaaatcaaa tcattaaagc ggccatccgt   2880

ataatattac cggatggccg cgccttttcc ttttatgtgg tccccacgag ggttacacag   2940

atgttattgt caaccaatca aattgcattc tcaaacgtta gataagtgtt catttgtctt   3000

tatatacttg gtccccaagt tttttgtctt gcaatatgtg ggacccactt cttaatgaat   3060

ttcctgaatc tgttcacgga tttcgttgta tgttagctat taaatatttg cagtccgttg   3120

aggaaactta cgagcccaat acattgggcc acgatttaat tagggatctt atatctgttg   3180

taagggcccg tgactatgtc gaagcgacca ggcgatataa tcatttccac gcccgtctcg   3240

aaggttcgcc gaaggctgaa cttcgacagc ccatacagca gccgtgctgc tgtccccatt   3300

gtccaaggca caaacaagcg acgatcatgg acgtacaggc ccatgtaccg aaagcccaga   3360

atatacagaa tgtatcgaag ccctgatgtt ccccgtggat gtgaaggccc atgtaaagtc   3420

cagtcttatg agcaacggga tgatattaag catactggta ttgttcgttg tgttagtgat   3480

gttactcgtg gatctggaat tactcacaga gtgggtaaga ggttctgtgt taaatcgata   3540

tattttttag gtaaagtctg gatggatgaa aatatcaaga agcagaatca cactaatcag   3600

gtcatgttct tcttggtccg tgatagaagg ccctatggaa acagcccaat ggattttgga   3660

caggttttta atatgttcga taatgagccc agtaccgcaa ccgtgaagaa tgatttgcgt   3720

gataggtttc aagtgatgag gaaatttcat gctacagtta ttggtgggcc ctctggaatg   3780

aaggaacagg cattagttaa gagatttttt aaaattaaca gtcatgtaac tttatttata   3840

ttcattcagg aggcagcaaa gtacgagaac catactgaaa acgccttgtt attgtatatg   3900

gcatgtacgc atgcctctaa tccagtgtat gcaactatga aaatacgcat ctatttctat   3960
```

```
gattcaatat caaattaata aaatttatat tttatatcat gagtttctgt tacatttatt   4020

gtgttttcaa gtacatcata caatacatga tcaactgctc tgattacatt gttaatggaa   4080

attacaccaa gactatctaa atacttaaga acttcatatc taaatactct taagaaatga   4140

ccagtctgag gctgtaatgt cgtccaaatt cggaagtcga gaaaacattt gtgaatcccc   4200

attaccttcc tgatgttgtg gttgaatctt atctgaatgg aaatgatgtc gtggttcatt   4260

agaaatggcc tctggctgtg ttctgttatc ttgaaataga ggggattgtt tatctcccag   4320

ataaaaacgc cattctctgc ctgaggagca gtgatgagtt cccctgtgcg tgaatccatg   4380

attattgcag ttgaggtgga ggtagtatga gcagccacag tctaggtcta cacgcttacg   4440

ccttattggt ttcttcttgg ctatcttgtg ttggaccttg attgatactt gcgaacagtg   4500

gctcgtagag ggtgacgaag gttgcattct tgagagccca atttttcaag gatatgtttt   4560

tttcttcgtc tagatattcc ctatatgagg aggtaggtcc tggattgcag aggaagatag   4620

tgggaattcc ccctttaatt tgaatgggct tcccgtactt tgtgttgctt tgccagtccc   4680

tctgggcccc catgaattcc ttgaagtgct ttaaataatg cgggtctacg tcatcaatga   4740

cgttgtacca cgcatcatta ctgtacacct ttgggcttag gtctagatgt ccacataaat   4800

aattatgtgg gcctagagac ctggcccaca ttgttttgcc tgttctgcta tcaccctcaa   4860

tgacaatact tatgggtctc catggccgcg cagcggaata cacgacgttc tcggcgaccc   4920

actcttcaag ttcatctgga acttgattaa aagaagaaga aagaaatgga gaaacataaa   4980

cttctaaagg aggactaaaa atcctatcta aatttgaact taaattatga aattgtaaaa   5040

tatagtcctt tggggccttc tcttttaata tattgagggc ctcggattta ctgcctgaat   5100

tgagtgcttc ggcatatgcg tcgttggcag attgctgacc tcctctagct gatctgccat   5160

cgatttggga aactccaaaa tcaatgaagt ttccgtcttt ctccacgtag gtcttgacat   5220

ctgttgagct cttagctgcc tgaatgttcg gatggaaatg tgctgacctg tttggtgata   5280

ccaggtcgaa gaaccgttgg ttcttacatt ggtatttgcc ttcgaattgg ataagcacat   5340

ggagatgtgg ttccccattc tcgtggagtt ctctgcaaac tttgatgtat tttttatttg   5400

ttggggtttc taggtttttt aattgggaaa gtgcttcctc tttagagaga gaacaattgg   5460

gatatgttag gaaataattt ttggcatata ttttaaataa acgaggcat               5509


<210> SEQ ID NO 2
<211> LENGTH: 2722
<212> TYPE: DNA
<213> ORGANISM: Artificial sequence
<220> FEATURE:
<223> OTHER INFORMATION: IL-60

<400> SEQUENCE: 2

gttgaaatga atcggtgtct ctcaaagctc tatggcaatc ggtgtatcgg tgtcttactt     60

atacctggac acctaatggc tatttggtaa tttcataaat gttcattgca attcaaaatt    120

caaaattcaa aaatcaaatc tttaaagcgg ccatccgtat aatattaccg gatggccgcg    180

ccttttgttt ttatgtggtc cccacgaggg ttacacagac gtcactgtca accaatcaaa    240

ttgcattctc aaacgttaga taagtgttca tttgtcttta tatacttggt ccccaagttt    300

tttgtcttgc aatatgtggg acccacttct taatgaattt cctgaatctg ttcacggatt    360

tcgttgtatg ttagctatta aatatttgca gtccgttgag gaaacttacg agcccaatac    420

attgggccac gatttaatta gggatcttat atctgttgta agggccccgt gactatgtcg    480

aagcgaccag gcgatataat catttccacg cccgtctcga aggttcgccg aaggctgaac    540
```

-continued

```
ttcgacggcc catacaggcc catgtaccga aagcccagaa atacagaatg tatcgaagcc    600
ctgatgttcc ccgtggatgt gaaggcccct ttaaagtcca gtcttatgag caacgggatg    660
atattaagca tcctggtatt gttcggttgt gttagtgatg ttactcgtgg atctggaatt    720
actcacagag tgggtaagag gttctgtgtt aaatcgatat attttttagg taaagtctgg    780
atggatgaaa atatcaagaa gcagaatcac actaatcagg tcatgttctt cttggtccgt    840
gatagaaggc cctatggaaa cagcccaatg gattttggac aggtttttaa tatgttcgat    900
aatgagccca gtaccgcaac cgtgaagaat gatttgcgtg ataggtttca agtgatgagg    960
aaatttcatg ctacagttat tggtgggccc tctggaatga aggaacaggc attagttaag   1020
agatttttta aaattaacag tcatgtaact tataatcatc aggaggcagc aaagtacgag   1080
aaccatactg aaaacgcctt gttattgtat atggcatgta cgcatgcctc taatccagtg   1140
tatgcaacta tgaaaatacg catctatttc tatgattcaa tatcaaatta ataaaattta   1200
tattttatat catgagtttc tgttacattt attgtgtttt caagtacatc atacaataca   1260
tgatcaactg ctctgattac attgttaatg gaaattacac caagactatc taaatactta   1320
agaacttcat atctaaatac tcttaagaaa tgaccagtct gaggctgtaa tgtcgtccaa   1380
attcggaagt tgagaaaaca tttgtgaatc cccattacct tcctgatgtt gtggttgaat   1440
cttatctgaa tggaaatgat gtcgtggttc attagaaatg gcctctggct gtgttctgtt   1500
atcttgaaat agagggggat tgttatctcc cagataaaaa cgccattctc tgcctgagga   1560
gcagtgatga gttcccctgt gcgtgaatcc atgattattg cagttgaggt ggaggtagta   1620
tgagcagcca cagtctaggt ctacacgctt acgccttatt ggtttcttct tggctatctt   1680
gtgttggacc ttgattgata cttgcgaaca gtggctcgta gagggtgacg aaggttgcat   1740
tcttgagagc ccaattttc aaggatatgt tttttcttc gtctagatat tccctatatg     1800
atgaggtagg tcctggattg cagaggaaga tagtgggaat tccccccttta atttgaatgg   1860
gcttcccgta ctttgtgttg ctttgccagt ccctctgggc ccccatgaat tccttgaagt   1920
gctttaaata atgcgggtct acgtcatcaa tgacgttgta ccacgcatca ttactgtaca   1980
cctttgggct taggtctaga tgtccacata aataattatg tgggcctaga gacctggccc   2040
acattgtttt gcctgttctg ctatcaccct caatgacaat acttatgggt ctccatggcc   2100
gcgcagcgga atacacgacg ttctcggcga cccactcttc aagttcatct ggaacttgat   2160
taaaagaaga agaaagaaat ggagaaacat aaacttctaa aggaggacta aaaatcctat   2220
ctaaatttga acttaaatta tgaaattgta aaatatagtc ctttggggcc ttctctttta   2280
atatattgag ggcctcggat ttactgcctg aattgagtgc ttcggcatat gcgtcgttgg   2340
cagattgctg acctcctcta gctgatctgc catcgatttg gaaaactcca aaatcaatga   2400
agtctccgtc tttctccacg taggtcttga catctgttga gctcttagct gcctgaatgt   2460
tcggatggaa atgtgctgac ctgtttggtg ataccaggtc gaagaaccgt tggttcttac   2520
attggtattt gccttcgaat tggataagca catggagatg tggttcccca ttctcgtgga   2580
gttctctgca aactttgatg tatttttat ttgttggggt ttctaggttt tttaattggg    2640
aaagtgcttc ctctttagag agagaacaat tgggatatgt taggaaataa tttttggcat   2700
atattttaaa taaacgaggc at                                            2722
```

<210> SEQ ID NO 3
<211> LENGTH: 238
<212> TYPE: PRT

<213> ORGANISM: Artificial sequence
<220> FEATURE:
<223> OTHER INFORMATION: IL-60 coat protein
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid

<400> SEQUENCE: 3

```
Met Ser Xaa Arg Pro Gly Asp Ile Ile Ile Ser Thr Pro Val Ser Lys
1               5                   10                  15

Val Arg Arg Arg Leu Asn Phe Xaa Gly Pro Tyr Arg Xaa Met Tyr Arg
            20                  25                  30

Lys Pro Arg Asn Thr Glu Cys Ile Glu Ala Leu Met Phe Pro Val Asp
        35                  40                  45

Val Lys Ala Pro Leu Lys Xaa Ser Xaa Met Ser Asn Gly Met Ile Leu
    50                  55                  60

Ser Xaa Leu Val Leu Phe Gly Cys Val Xaa Asp Val Thr Xaa Gly Ser
65                  70                  75                  80

Gly Ile Thr His Arg Val Gly Lys Arg Phe Cys Val Lys Ser Ile Tyr
                85                  90                  95

Phe Leu Gly Lys Val Trp Met Asp Glu Asn Ile Lys Lys Gln Asn His
            100                 105                 110

Thr Asn Gln Val Met Phe Phe Leu Val Arg Asp Arg Arg Pro Tyr Gly
        115                 120                 125

Asn Ser Pro Met Asp Phe Gly Gln Val Phe Asn Met Phe Asp Asn Glu
    130                 135                 140

Pro Ser Thr Ala Thr Val Lys Asn Asp Leu Arg Asp Arg Phe Gln Val
145                 150                 155                 160

Met Arg Lys Phe His Ala Thr Val Ile Gly Gly Pro Ser Gly Met Lys
                165                 170                 175

Glu Gln Ala Leu Val Lys Arg Phe Phe Lys Ile Asn Ser His Val Thr
            180                 185                 190

Tyr Asn His Gln Glu Ala Ala Lys Tyr Glu Asn His Thr Glu Asn Ala
        195                 200                 205

Leu Leu Leu Tyr Met Ala Cys Thr His Ala Ser Asn Pro Val Tyr Ala
    210                 215                 220
```

-continued

```
Thr Met Lys Ile Arg Ile Tyr Phe Tyr Asp Ser Ile Ser Asn
225                 230                 235

<210> SEQ ID NO 4
<211> LENGTH: 2787
<212> TYPE: DNA
<213> ORGANISM: Tomato yellow leaf curl virus

<400> SEQUENCE: 4

gttgaaatga atcggtgtcc ctcaaagctc tatggcaatc ggtgtatcgg tgtcttactt     60

atacttggac acctaatggc tatttggtaa tttcataaat gttcatttca attcaaaatt    120

caaaattcaa aaatcaaatc attaaagcgg ccatccgtat aatattaccg gatggccgcg    180

ccttttcctt ttatgtggtc cccacgaggg ttacacagat gttattgtca accaatcaaa    240

ttgcattctc aaacgttaga taagtgttca tttgtcttta tatacttggt ccccaagttt    300

tttgtcttgc aatatgtggg acccacttct taatgaattt cctgaatctg ttcacggatt    360

tcgttgtatg ttagctatta aatatttgca gtccgttgag gaaacttacg agcccaatac    420

attgggccac gatttaatta gggatcttat atctgttgta agggcccgtg actatgtcga    480

agcgaccagg cgatataatc atttccacgc ccgtctcgaa ggttcgccga aggctgaact    540

tcgacagccc atacagcagc cgtgctgctg tccccattgt ccaaggcaca aacaagcgac    600

gatcatggac gtacaggccc atgtaccgaa agcccagaat atacagaatg tatcgaagcc    660

ctgatgttcc ccgtggatgt gaaggcccat gtaaagtcca gtcttatgag caacgggatg    720

atattaagca tactggtatt gttcgttgtg ttagtgatgt tactcgtgga tctggaatta    780

ctcacagagt gggtaagagg ttctgtgtta aatcgatata ttttttaggt aaagtctgga    840

tggatgaaaa tatcaagaag cagaatcaca ctaatcaggt catgttcttc ttggtccgtg    900

atagaaggcc ctatggaaac agcccaatgg attttggaca ggtttttaat atgttcgata    960

atgagcccag taccgcaacc gtgaagaatg atttgcgtga taggtttcaa gtgatgagga   1020

aatttcatgc tacagttatt ggtgggccct ctggaatgaa ggaacaggca ttagttaaga   1080

gattttttaa aattaacagt catgtaactt tatttatatt cattcaggag gcagcaaagt   1140

acgagaacca tactgaaaac gccttgttat tgtatatggc atgtacgcat gcctctaatc   1200

cagtgtatgc aactatgaaa atacgcatct atttctatga ttcaatatca aattaataaa   1260

atttatattt tatatcatga gtttctgtta catttattgt gttttcaagt acatcataca   1320

atacatgatc aactgctctg attacattgt taatggaaat tacaccaaga ctatctaaat   1380

acttaagaac ttcatatcta aatactctta agaaatgacc agtctgaggc tgtaatgtcg   1440

tccaaattcg gaagtcgaga aaacatttgt gaatccccat taccttcctg atgttgtggt   1500

tgaatcttat ctgaatggaa atgatgtcgt ggttcattag aaatggcctc tggctgtgtt   1560

ctgttatctt gaaatagagg ggattgttta tctcccagat aaaaacgcca ttctctgcct   1620

gaggagcagt gatgagttcc cctgtgcgtg aatccatgat tattgcagtt gaggtggagg   1680

tagtatgagc agccacagtc taggtctaca cgcttacgcc ttattggttt cttcttggct   1740

atcttgtgtt ggaccttgat tgatacttgc gaacagtggc tcgtagaggg tgacgaaggt   1800

tgcattcttg agagcccaat ttttcaagga tatgtttttt tcttcgtcta gatattccct   1860

atatgaggag gtaggtcctg gattgcagag gaagatagtg ggaattcccc ctttaatttg   1920

aatgggcttc ccgtactttg tgttgctttg ccagtccctc tgggccccca tgaattcctt   1980

gaagtgcttt aaataatgcg ggtctacgtc atcaatgacg ttgtaccacg catcattact   2040
```

```
gtacaccttt gggcttaggt ctagatgtcc acataaataa ttatgtgggc ctagagacct   2100

ggcccacatt gttttgcctg ttctgctatc accctcaatg acaatactta tgggtctcca   2160

tggccgcgca gcggaataca cgacgttctc ggcgacccac tcttcaagtt catctggaac   2220

ttgattaaaa gaagaagaaa gaaatggaga aacataaact tctaaaggag gactaaaaat   2280

cctatctaaa tttgaactta aattatgaaa ttgtaaaata tagtcctttg gggccttctc   2340

ttttaatata ttgagggcct cggatttact gcctgaattg agtgcttcgg catatgcgtc   2400

gttggcagat tgctgacctc ctctagctga tctgccatcg atttgggaaa ctccaaaatc   2460

aatgaagttt ccgtctttct ccacgtaggt cttgacatct gttgagctct tagctgcctg   2520

aatgttcgga tggaaatgtg ctgacctgtt tggggatacc aagtcgaaga accgttggtt   2580

cttacattgg tatttgcctt cgaattggat aagcacatgg agatgtggtt ccccattctc   2640

gtggagttct ttgcaaactt tgatgtattt tttatttgtt ggggtttcta gtttttttaa   2700

ttgggaaagt gcttcctctt tagagagaga acaattggga tatgttagga aataattttt   2760

ggcatatatt ttaaataaac gaggcat                                        2787
```

```
<210> SEQ ID NO 5
<211> LENGTH: 280
<212> TYPE: PRT
<213> ORGANISM: Tomato yellow leaf curl virus

<400> SEQUENCE: 5

Met Ser Lys Arg Pro Gly Asp Ile Ile Ile Ser Thr Pro Val Ser Lys
1               5                   10                  15

Val Arg Arg Arg Leu Asn Phe Asp Ser Pro Tyr Ser Ser Arg Ala Ala
            20                  25                  30

Val Pro Ile Val Gln Gly Thr Asn Lys Arg Arg Ser Trp Thr Tyr Arg
        35                  40                  45

Pro Met Tyr Arg Lys Pro Arg Ile Tyr Arg Met Tyr Arg Ser Pro Asp
    50                  55                  60

Val Pro Arg Gly Cys Glu Gly Pro Cys Lys Val Gln Ser Tyr Glu Gln
65                  70                  75                  80

Arg Asp Asp Ile Lys His Thr Gly Ile Val Arg Cys Val Ser Asp Val
                85                  90                  95

Thr Arg Gly Ser Gly Ile Thr His Arg Val Gly Lys Arg Phe Cys Val
            100                 105                 110

Lys Ser Ile Tyr Phe Leu Gly Lys Val Trp Met Asp Glu Asn Ile Lys
        115                 120                 125

Lys Gln Asn His Thr Asn Gln Val Met Phe Phe Leu Val Arg Asp Arg
    130                 135                 140

Arg Pro Tyr Gly Asn Ser Pro Met Asp Phe Gly Gln Val Phe Asn Met
145                 150                 155                 160

Phe Asp Asn Glu Pro Ser Thr Ala Thr Val Lys Asn Asp Leu Arg Asp
                165                 170                 175

Arg Phe Gln Val Met Arg Lys Phe His Ala Thr Val Ile Gly Gly Pro
            180                 185                 190

Ser Gly Met Lys Glu Gln Ala Leu Val Lys Arg Phe Phe Lys Ile Asn
        195                 200                 205

Ser His Val Thr Leu Phe Ile Phe Ile Gln Glu Ala Ala Lys Tyr Glu
    210                 215                 220

Asn His Thr Glu Asn Ala Leu Leu Leu Tyr Met Ala Cys Thr His Ala
225                 230                 235                 240
```

Ser Asn Pro Val Tyr Ala Thr Met Lys Ile Arg Ile Tyr Phe Tyr Asp
245 250 255

Ser Ile Ser Asn Ser Asn Pro Val Tyr Ala Thr Met Lys Ile Arg Ile
260 265 270

Tyr Phe Tyr Asp Ser Ile Ser Asn
275 280

<210> SEQ ID NO 6
<211> LENGTH: 116
<212> TYPE: PRT
<213> ORGANISM: Tomato yellow leaf curl virus

<400> SEQUENCE: 6

Met Trp Asp Pro Leu Leu Asn Glu Phe Pro Glu Ser Val His Gly Phe
1 5 10 15

Arg Cys Met Leu Ala Ile Lys Tyr Leu Gln Ser Val Glu Glu Thr Tyr
20 25 30

Glu Pro Asn Thr Leu Gly His Asp Leu Ile Arg Asp Leu Ile Ser Val
35 40 45

Val Arg Ala Arg Asp Tyr Val Glu Ala Thr Arg Arg Tyr Asn His Phe
50 55 60

His Ala Arg Leu Glu Gly Ser Pro Lys Ala Glu Leu Arg Gln Pro Ile
65 70 75 80

Gln Gln Pro Cys Cys Cys Pro His Cys Pro Arg His Lys Gln Ala Thr
85 90 95

Ile Met Asp Val Gln Ala His Val Pro Lys Ala Gln Asn Ile Gln Asn
100 105 110

Val Ser Lys Pro
115

<210> SEQ ID NO 7
<211> LENGTH: 357
<212> TYPE: PRT
<213> ORGANISM: Tomato yellow leaf curl virus

<400> SEQUENCE: 7

Met Pro Arg Leu Phe Lys Ile Tyr Ala Lys Asn Tyr Phe Leu Thr Tyr
1 5 10 15

Pro Asn Cys Ser Leu Ser Lys Glu Glu Ala Leu Ser Gln Leu Lys Lys
20 25 30

Leu Glu Thr Pro Thr Asn Lys Lys Tyr Ile Lys Val Cys Lys Glu Leu
35 40 45

His Glu Asn Gly Glu Pro His Leu His Val Leu Ile Gln Phe Glu Gly
50 55 60

Lys Tyr Gln Cys Lys Asn Gln Arg Phe Phe Asp Leu Val Ser Pro Asn
65 70 75 80

Arg Ser Ala His Phe His Pro Asn Ile Gln Ala Ala Lys Ser Ser Thr
85 90 95

Asp Val Lys Thr Tyr Val Glu Lys Asp Gly Asn Phe Ile Asp Phe Gly
100 105 110

Val Ser Gln Ile Asp Gly Arg Ser Ala Arg Gly Gly Gln Gln Ser Ala
115 120 125

Asn Asp Ala Tyr Ala Glu Ala Leu Asn Ser Gly Ser Lys Ser Glu Ala
130 135 140

Leu Asn Ile Leu Lys Glu Lys Ala Pro Lys Asp Tyr Ile Leu Gln Phe
145 150 155 160

```
His Asn Leu Ser Ser Asn Leu Asp Arg Ile Phe Ser Pro Pro Leu Glu
                165                 170                 175

Val Tyr Val Ser Pro Phe Leu Ser Ser Ser Phe Asn Gln Val Pro Asp
            180                 185                 190

Glu Leu Glu Glu Trp Val Ala Glu Asn Val Val Tyr Ser Ala Ala Arg
        195                 200                 205

Pro Trp Arg Pro Ile Ser Ile Val Ile Glu Gly Asp Ser Arg Thr Gly
    210                 215                 220

Lys Thr Met Trp Ala Arg Ser Leu Gly Pro His Asn Tyr Leu Cys Gly
225                 230                 235                 240

His Leu Asp Leu Ser Pro Lys Val Tyr Ser Asn Asp Ala Trp Tyr Asn
                245                 250                 255

Val Ile Asp Asp Val Asp Pro His Tyr Leu Lys His Phe Lys Glu Phe
            260                 265                 270

Met Gly Ala Gln Arg Asp Trp Gln Ser Asn Thr Lys Tyr Gly Lys Pro
        275                 280                 285

Ile Gln Ile Lys Gly Gly Ile Pro Thr Ile Phe Leu Cys Asn Pro Gly
    290                 295                 300

Pro Thr Ser Ser Tyr Arg Glu Tyr Leu Asp Glu Glu Lys Asn Ile Ser
305                 310                 315                 320

Leu Lys Asn Trp Ala Leu Lys Asn Ala Thr Phe Val Thr Leu Tyr Glu
                325                 330                 335

Pro Leu Phe Ala Ser Ile Asn Gln Gly Pro Thr Gln Asp Ser Gln Glu
            340                 345                 350

Glu Thr Asn Lys Ala
        355
```

<210> SEQ ID NO 8
<211> LENGTH: 98
<212> TYPE: PRT
<213> ORGANISM: Tomato yellow leaf curl virus

<400> SEQUENCE: 8

```
Arg Met Gly Asn His Ile Ser Met Cys Leu Ser Asn Ser Lys Ala Asn
1               5                   10                  15

Thr Asn Val Arg Thr Asn Gly Ser Ser Thr Trp Tyr Pro Gln Thr Gly
            20                  25                  30

Gln His Ile Ser Ile Arg Thr Phe Arg Gln Leu Arg Ala Gln Gln Met
        35                  40                  45

Ser Arg Pro Thr Trp Arg Lys Thr Glu Thr Ser Leu Ile Leu Glu Phe
    50                  55                  60

Pro Lys Ser Met Ala Asp Gln Leu Glu Glu Val Ser Asn Leu Pro Thr
65                  70                  75                  80

Thr His Met Pro Lys His Ser Ile Gln Ala Val Asn Pro Arg Pro Ser
                85                  90                  95

Ile Tyr
```

<210> SEQ ID NO 9
<211> LENGTH: 7500
<212> TYPE: DNA
<213> ORGANISM: Artificial sequence
<220> FEATURE:
<223> OTHER INFORMATION: IL-60-BS-GUS
<220> FEATURE:
<221> NAME/KEY: misc_feature
<222> LOCATION: (1377)..(1377)
<223> OTHER INFORMATION: n is a, c, g, or t -continued
<220> FEATURE:
<221> NAME/KEY: misc_feature
<222> LOCATION: (1404)..(1404)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1480)..(1480)
<223> OTHER INFORMATION: n is a, c, g, or t
<220> FEATURE:
<221> NAME/KEY: misc_feature
<222> LOCATION: (1495)..(1495)
<223> OTHER INFORMATION: n is a, c, g, or t
<220> FEATURE:
<221> NAME/KEY: misc_feature
<222> LOCATION: (1566)..(1566)
<223> OTHER INFORMATION: n is a, c, g, or t
<220> FEATURE:
<221> NAME/KEY: misc_feature
<222> LOCATION: (1573)..(1573)
<223> OTHER INFORMATION: n is a, c, g, or t
<220> FEATURE:
<221> NAME/KEY: misc_feature
<222> LOCATION: (1580)..(1580)
<223> OTHER INFORMATION: n is a, c, g, or t
<220> FEATURE:
<221> NAME/KEY: misc_feature
<222> LOCATION: (1607)..(1607)
<223> OTHER INFORMATION: n is a, c, g, or t
<220> FEATURE:
<221> NAME/KEY: misc_feature
<222> LOCATION: (1632)..(1632)
<223> OTHER INFORMATION: n is a, c, g, or t
<220> FEATURE:
<221> NAME/KEY: misc_feature
<222> LOCATION: (1643)..(1644)
<223> OTHER INFORMATION: n is a, c, g, or t
<220> FEATURE:
<221> NAME/KEY: misc_feature
<222> LOCATION: (2490)..(2490)
<223> OTHER INFORMATION: n is a, c, g, or t

<400> SEQUENCE: 9
ctgacgcgcc ctgtagcggc gcattaagcg cggcgggtgt ggtggttacg cgcagcgtga 60
ccgctacact tgccagcgcc ctagcgcccg ctcctttcgc tttcttccct tcctttctcg 120
ccacgttcgc cggctttccc cgtcaagctc taaatcgggg gctcccttta gggttccgat 180
ttagtgcttt acggcacctc gaccccaaaa aacttgatta gggtgatggt tcacgtagtg 240
ggccatcgcc ctgatagacg gtttttcgcc ctttgacgtt ggagtccacg ttctttaata 300
gtggactctt gttccaaact ggaacaacac tcaaccctat ctcggtctat tcttttgatt 360
tataagggat tttgccgatt tcggcctatt ggttaaaaaa tgagctgatt taacaaaaat 420
ttaacgcgaa ttttaacaaa atattaacgc ttacaatttc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgcgtaata cgactcacta tagggcgaat tggagctctt 660
agctgcctga atgttcggat ggaaatgtgc tgacctgttt ggtgatacca ggtcgaagaa 720
ccgttggttc ttacattggt atttgccttc gaattggata agcacatgga gatgtggttc 780
cccattctcg tggagttctc tgcaaacttt gatgtatttt ttatttgttg gggtttctag 840 gtttttttaat tgggaaagtg cttcctcttt agagagagaa caattgggat atgttaggaa 900
ataatttttg gcatatattt taaataaacg aggcatgttg aaatgaatcg gtgtctctca 960

```
aagctctatg gcaatcggtg tatcggtgtc ttacttatac ctggacacct aatggctatt   1020
tggtaatttc ataaatgttc attgcaattc aaaattcaaa attcaaaaat caaatcttta   1080
aagcggccat ccgtataata ttaccggatg gccgcgcctt ttgtttttat gtggtcccca   1140
cgagggttac acagacgtca ctgtcaacca atcaaattgc attctcaaac gttagataag   1200
tgttcatttg tctttatata cttggtcccc aagtttttg tcttgcaata tgtgggaccc   1260
acttcttaat gaatttcctg aatctgttca cggatttcgt tgtatgttag ctattaaata   1320
tttgcagtcc gttgaggaaa cttacgagcc caatacattg ggccacgatt taattangga   1380
tcttatatct gttgtaaggg cccngtgact atgtcgaanc gaccaggcga tataatcatt   1440
tccacgcccg tctcgaaggt tcgccgaagg ctgaacttcn acggcccata caggnccatg   1500
taccgaaagc ccagaaatac agaatgtatc gaagccctga tgttccccgt ggatgtgaag   1560
gccccnttaa agnccagtcn tatgagcaac gggatgatat taagcancct ggtattgttc   1620
ggttgtgtta gngatgttac tcnnggatct ggaattactc acagagtggg taagaggttc   1680
tgtgttaaat cgatatattt tttaggtaaa gtctggatgg atgaaaatat caagaagcag   1740
aatcacacta atcaggtcat gttcttcttg gtccgtgata gaaggcccta tggaaacagc   1800
ccaatggatt ttggacaggt ttttaatatg ttcgataatg agcccagtac cgcaaccgtg   1860
aagaatgatt tgcgtgatag gtttcaagtg atgaggaaat ttcatgctac agttattggt   1920
gggccctctg gaatgaagga acaggcatta gttaagagat tttttaaaat taacagtcat   1980
gtaacttata atcatcagga ggcagcaaag tacgagaacc atactgaaaa cgccttgtta   2040
ttgtatatgg catgtacgca tgcctctaat ccagtgtatg caactatgaa aatacgcatc   2100
tatttctatg attcaatatc aaattaataa aatttatatt ttatatcatg agtttctgtt   2160
acatttattg tgttttcaag tacatcatac aatacatgat caactgctct gattacattg   2220
ttaatggaaa ttacaccaag actatctaaa tacttaagaa cttcatatct aaatactctt   2280
aagaaatgac cagtctgagg ctgtaatgtc gtccaaattc ggaagttgag aaaacatttg   2340
tgaatcccca ttaccttcct gatgttgtgg ttgaatctta tctgaatgga aatgatgtcg   2400
tggttcatta gaaatggcct ctggctgtgt tctgttatct tgaaatagag ggggattgtt   2460
atctcccaga taaaaacgcc attctctgcn tgaggagcag tgatgagttc ccctgtgcgt   2520
gaatccatga ttattgcagt tgaggtggag gtagtatgag cagccacagt ctaggtctac   2580
acgcttacgc cttattggtt tcttcttggc tatcttgtgt tggaccttga ttgatacttg   2640
cgaacagtgg ctcgtagagg gtgacgaagg ttgcattctt gagagcccaa tttttcaagg   2700
atatgttttt ttcttcgtct agatattccc tatatgatga ggtaggtcct ggattgcaga   2760
ggaagatagt gggaattccc cctttaattt gaatgggctt cccgtacttt gtgttgcttt   2820
gccagtccct ctgggccccc atgaattcct tgaagtgctt taaataatgc gggtctacgt   2880
catcaatgac gttgtaccac gcatcattac tgtacacctt tgggcttagg tctagatgtc   2940
cacataaata attatgtggg cctagagacc tggcccacat tgttttgcct gttctgctat   3000
caccctcaat gacaatactt atgggtctcc atggccgcgc agcggaatac acgacgttct   3060
cggcgaccca ctcttcaagt tcatctggaa cttgattaaa agaagaagaa agaaatggag   3120
aaacataaac ttctaaagga ggactaaaaa tcctatctaa atttgaactt aaattatgaa   3180
attgtaaaat atagtccttt ggggccttct cttttaatat attgagggcc tcggatttac   3240
tgcctgaatt gagtgcttcg gcatatgcgt cgttggcaga ttgctgacct cctctagctg   3300
atctgccatc gatttggaaa actccaaaat caatgaagtc tccgtctttc tccacgtagg   3360
```

-continued

```
tcttgacatc tgttgagctc caccgcggtg gcggccgctc tagaactagt ggatccccg   3420
ggctgcagga attcgatgag ctcatgttac gtcctgtaga aaccccaacc cgtgaaatca   3480
aaaaactcga cggcctgtgg gcattcagtc tggatcgcga aaactgtgga attgatcagc   3540
gttggtggga aagcgcgtta caagaaagcc gggcaattgc tgtgccaggc agttttaacg   3600
atcagttcgc cgatgcagat attcgtaatt atgcgggcaa cgtctggtat cagcgcgaag   3660
tctttatacc gaaaggttgg gcaggccagc gtatcgtgct gcgtttcgat gcggtcactc   3720
attacggcaa agtgtgggtc aataatcagg aagtgatgga gcatcagggc ggctatacgc   3780
catttgaagc cgatgtcacg ccgtatgtta ttgccgggaa aagtgtacgt atcaccgttt   3840
gtgtgaacaa cgaactgaac tggcagacta tcccgccggg aatggtgatt accgacgaaa   3900
acggcaagaa aaagcagtct tacttccatg atttctttaa ctatgccggg atccatcgca   3960
gcgtaatgct ctacaccacg ccgaacacct gggtggacga tatcaccgtg gtgacgcatg   4020
tcgcgcaaga ctgtaaccac gcgtctgttg actggcaggt ggtggccaat ggtgatgtca   4080
gcgttgaact gcgtgatgcg gatcaacagg tggttgcaac tggacaaggc actagcggga   4140
ctttgcaagt ggtgaatccg cacctctggc aaccgggtga aggttatctc tatgaactgt   4200
gcgtcacagc caaaagccag acagagtgtg atatctaccc gcttcgcgtc ggcatccggt   4260
cagtggcagt gaagggcgaa cagttcctga ttaaccacaa accgttctac tttactggct   4320
ttggtcgtca tgaagatgcg gacttacgtg gcaaaggatt cgataacgtg ctgatggtgc   4380
acgaccacgc attaatggac tggattgggg ccaactccta ccgtacctcg cattaccctt   4440
acgctgaaga gatgctcgac tggcagatg aacatggcat cgtggtgatt gatgaaactg   4500
ctgctgtcgg ctttaacctc tctttaggca ttggtttcga agcgggcaac aagccgaaag   4560
aactgtacag cgaagaggca gtcaacgggg aaactcagca agcgcactta caggcgatta   4620
aagagctgat agcgcgtgac aaaaaccacc caagcgtggt gatgtggagt attgccaacg   4680
aaccggatac ccgtccgcaa gtgcacggga atatttcgcc actggcggaa gcaacgcgta   4740
aactcgaccc gacgcgtccg atcacctgcg tcaatgtaat gttctgcgac gctcacaccg   4800
ataccatcag cgatctcttt gatgtgctgt gcctgaaccg ttattacgga tggtatgtcc   4860
aaagcggcga tttggaaacg gcagagaagg tactggaaaa agaacttctg gcctggcagg   4920
agaaactgca tcagccgatt atcatcaccg aatacggcgt ggatacgtta gccgggctgc   4980
actcaatgta caccgacatg tggagtgaag agtatcagtg tgcatggctg gatatgtatc   5040
accgcgtctt tgatcgcgtc agcgccgtcg tcggtgaaca ggtatggaat ttcgccgatt   5100
ttgcgacctc gcaaggcata ttgcgcgttg gcggtaacaa gaaagggatc ttcactcgcg   5160
accgcaaacc gaagtcggcg gcttttctgc tgcaaaaacg ctggactggc atgaacttcg   5220
gtgaaaaacc gcagcaggga ggcaaacagt cgacatcaag cttatcgata ccgtcgacct   5280
cgaggggggg cccggtaccc agcttttgtt ccctttagtg agggttaatt gcgcgcttgg   5340
cgtaatcatg gtcatagctg tttcctgtgt gaaattgtta tccgctcaca attccacaca   5400
acatacgagc cggaagcata aagtgtaaag cctggggtgc ctaatgagtg agctaactca   5460
cattaattgc gttgcgctca ctgcccgctt tccagtcggg aaacctgtcg tgccagctgc   5520
attaatgaat cggccaacgc gcggggagag gcggtttgcg tattgggcgc tcttccgctt   5580
cctcgctcac tgactcgctg cgctcggtcg ttcggctgcg gcgagcggta tcagctcact   5640
caaaggcggt aatacggtta tccacagaat caggggataa cgcaggaaag aacatgtgag   5700
```

-continued caaaaggcca gcaaaaggcc aggaaccgta aaaaggccgc gttgctggcg tttttccata 5760
ggctccgccc ccctgacgag catcacaaaa atcgacgctc aagtcagagg tggcgaaacc 5820
cgacaggact ataaagatac caggcgtttc cccctggaag ctccctcgtg cgctctcctg 5880
ttccgaccct gccgcttacc ggatacctgt ccgcctttct cccttcggga agcgtggcgc 5940
tttctcatag ctcacgctgt aggtatctca gttcggtgta ggtcgttcgc tccaagctgg 6000
gctgtgtgca cgaacccccc gttcagcccg accgctgcgc cttatccggt aactatcgtc 6060
ttgagtccaa cccggtaaga cacgacttat cgccactggc agcagccact ggtaacagga 6120
ttagcagagc gaggtatgta ggcggtgcta cagagttctt gaagtggtgg cctaactacg 6180
gctacactag aaggacagta tttggtatct gcgctctgct gaagccagtt accttcggaa 6240
aaagagttgg tagctcttga tccggcaaac aaaccaccgc tggtagcggt ggtttttttg 6300
tttgcaagca gcagattacg cgcagaaaaa aaggatctca agaagatcct ttgatctttt 6360
ctacggggtc tgacgctcag tggaacgaaa actcacgtta agggattttg gtcatgagat 6420
tatcaaaaag gatcttcacc tagatccttt taaattaaaa atgaagtttt aaatcaatct 6480
aaagtatata tgagtaaact tggtctgaca gttaccaatg cttaatcagt gaggcaccta 6540
tctcagcgat ctgtctattt cgttcatcca tagttgcctg actccccgtc gtgtagataa 6600
ctacgatacg ggagggctta ccatctggcc ccagtgctgc aatgataccg cgagacccac 6660
gctcaccggc tccagattta tcagcaataa accagccagc cggaagggcc gagcgcagaa 6720
gtggtcctgc aactttatcc gcctccatcc agtctattaa ttgttgccgg gaagctagag 6780
taagtagttc gccagttaat agtttgcgca acgttgttgc cattgctaca ggcatcgtgg 6840
tgtcacgctc gtcgtttggt atggcttcat tcagctccgg ttcccaacga tcaaggcgag 6900
ttacatgatc ccccatgttg tgcaaaaaag cggttagctc cttcggtcct ccgatcgttg 6960
tcagaagtaa gttggccgca gtgttatcac tcatggttat ggcagcactg cataattctc 7020
ttactgtcat gccatccgta agatgctttt ctgtgactgg tgagtactca accaagtcat 7080
tctgagaata gtgtatgcgg cgaccgagtt gctcttgccc ggcgtcaata cgggataata 7140
ccgcgccaca tagcagaact ttaaaagtgc tcatcattgg aaaacgttct tcggggcgaa 7200
aactctcaag gatcttaccg ctgttgagat ccagttcgat gtaacccact cgtgcaccca 7260
actgatcttc agcatctttt actttcacca gcgtttctgg gtgagcaaaa acaggaaggc 7320
aaaatgccgc aaaaaaggga ataagggcga cacggaaatg ttgaatactc atactcttcc 7380
tttttcaata ttattgaagc atttatcagg gttattgtct catgagcgga tacatatttg 7440
aatgtattta gaaaaataaa caaatagggg ttccgcgcac atttccccga aaagtgccac 7500

<210> SEQ ID NO 10
<211> LENGTH: 6500
<212> TYPE: DNA
<213> ORGANISM: Artificial sequence
<220> FEATURE:
<223> OTHER INFORMATION: IL-60-BS-GFP
<220> FEATURE:
<221> NAME/KEY: misc_feature
<222> LOCATION: (1377)..(1377)
<223> OTHER INFORMATION: n is a, c, g, or t
<220> FEATURE:
<221> NAME/KEY: misc_feature
<222> LOCATION: (1404)..(1404)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1480)..(1480)
<223> OTHER INFORMATION: n is a, c, g, or t
<220> FEATURE:
<221> NAME/KEY: misc_feature
<222> LOCATION: (1495)..(1495)
<223> OTHER INFORMATION: n is a, c, g, or t
<220> FEATURE:
<221> NAME/KEY: misc_feature
<222> LOCATION: (1566)..(1566)
<223> OTHER INFORMATION: n is a, c, g, or t
<220> FEATURE:
<221> NAME/KEY: misc_feature
<222> LOCATION: (1573)..(1573)
<223> OTHER INFORMATION: n is a, c, g, or t
<220> FEATURE:
<221> NAME/KEY: misc_feature
<222> LOCATION: (1580)..(1580)
<223> OTHER INFORMATION: n is a, c, g, or t
<220> FEATURE:
<221> NAME/KEY: misc_feature
<222> LOCATION: (1607)..(1607)
<223> OTHER INFORMATION: n is a, c, g, or t
<220> FEATURE:
<221> NAME/KEY: misc_feature
<222> LOCATION: (1632)..(1632)
<223> OTHER INFORMATION: n is a, c, g, or t
<220> FEATURE:
<221> NAME/KEY: misc_feature
<222> LOCATION: (1643)..(1644)
<223> OTHER INFORMATION: n is a, c, g, or t
<220> FEATURE:
<221> NAME/KEY: misc_feature
<222> LOCATION: (2490)..(2490)
<223> OTHER INFORMATION: n is a, c, g, or t

<400> SEQUENCE: 10
ctgacgcgcc ctgtagcggc gcattaagcg cggcgggtgt ggtggttacg cgcagcgtga 60
ccgctacact tgccagcgcc ctagcgcccg ctcctttcgc tttcttccct tcctttctcg 120
ccacgttcgc cggctttccc cgtcaagctc taaatcgggg gctcccttta gggttccgat 180
ttagtgcttt acggcacctc gaccccaaaa aacttgatta gggtgatggt tcacgtagtg 240
ggccatcgcc ctgatagacg gtttttcgcc ctttgacgtt ggagtccacg ttctttaata 300
gtggactctt gttccaaact ggaacaacac tcaaccctat ctcggtctat tcttttgatt 360
tataagggat tttgccgatt tcggcctatt ggttaaaaaa tgagctgatt taacaaaaat 420
ttaacgcgaa ttttaacaaa atattaacgc ttacaatttc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgcgtaata cgactcacta tagggcgaat tggagctctt 660
agctgcctga atgttcggat ggaaatgtgc tgacctgttt ggtgatacca ggtcgaagaa 720
ccgttggttc ttacattggt atttgccttc gaattggata agcacatgga gatgtggttc 780
cccattctcg tggagttctc tgcaaacttt gatgtatttt ttatttgttg gggtttctag 840
gttttttaat tgggaaagtg cttcctcttt agagagagaa caattgggat atgttaggaa 900
ataatttttg gcatatattt taaataaacg aggcatgttg aaatgaatcg gtgtctctca 960
aagctctatg gcaatcggtg tatcggtgtc ttacttatac ctggacacct aatggctatt 1020
tggtaatttc ataaatgttc attgcaattc aaaattcaaa attcaaaaat caaatcttta 1080
aagcggccat ccgtataata ttaccggatg gccgcgcctt ttgtttttat gtggtcccca 1140
cgagggttac acagacgtca ctgtcaacca atcaaattgc attctcaaac gttagataag 1200

-continued

```
tgttcatttg tctttatata cttggtcccc aagttttttg tcttgcaata tgtgggaccc   1260
acttcttaat gaatttcctg aatctgttca cggatttcgt tgtatgttag ctattaaata   1320
tttgcagtcc gttgaggaaa cttacgagcc caatacattg ggccacgatt taattangga   1380
tcttatatct gttgtaaggg cccngtgact atgtcgaanc gaccaggcga tataatcatt   1440
tccacgcccg tctcgaaggt tcgccgaagg ctgaacttcn acggcccata caggnccatg   1500
taccgaaagc ccagaaatac agaatgtatc gaagccctga tgttccccgt ggatgtgaag   1560
gccccnttaa agnccagtcn tatgagcaac gggatgatat taagcancct ggtattgttc   1620
ggttgtgtta gngatgttac tcnnggatct ggaattactc acagagtggg taagaggttc   1680
tgtgttaaat cgatatattt tttaggtaaa gtctggatgg atgaaaatat caagaagcag   1740
aatcacacta atcaggtcat gttcttcttg gtccgtgata gaaggcccta tggaaacagc   1800
ccaatggatt ttggacaggt ttttaatatg ttcgataatg agcccagtac cgcaaccgtg   1860
aagaatgatt tgcgtgatag gtttcaagtg atgaggaaat ttcatgctac agttattggt   1920
gggccctctg gaatgaagga acaggcatta gttaagagat tttttaaaat taacagtcat   1980
gtaacttata atcatcagga ggcagcaaag tacgagaacc atactgaaaa cgccttgtta   2040
ttgtatatgg catgtacgca tgcctctaat ccagtgtatg caactatgaa aatacgcatc   2100
tatttctatg attcaatatc aaattaataa aatttatatt ttatatcatg agtttctgtt   2160
acatttattg tgttttcaag tacatcatac aatacatgat caactgctct gattacattg   2220
ttaatggaaa ttacaccaag actatctaaa tacttaagaa cttcatatct aaatactctt   2280
aagaaatgac cagtctgagg ctgtaatgtc gtccaaattc ggaagttgag aaaacatttg   2340
tgaatcccca ttaccttcct gatgttgtgg ttgaatctta tctgaatgga aatgatgtcg   2400
tggttcatta gaaatggcct ctggctgtgt tctgttatct tgaaatagag ggggattgtt   2460
atctcccaga taaaaacgcc attctctgcn tgaggagcag tgatgagttc ccctgtgcgt   2520
gaatccatga ttattgcagt tgaggtggag gtagtatgag cagccacagt ctaggtctac   2580
acgcttacgc cttattggtt tcttcttggc tatcttgtgt tggaccttga ttgatacttg   2640
cgaacagtgg ctcgtagagg gtgacgaagg ttgcattctt gagagcccaa tttttcaagg   2700
atatgttttt ttcttcgtct agatattccc tatatgatga ggtaggtcct ggattgcaga   2760
ggaagatagt gggaattccc cctttaattt gaatgggctt cccgtacttt gtgttgcttt   2820
gccagtccct ctgggccccc atgaattcct tgaagtgctt taaataatgc gggtctacgt   2880
catcaatgac gttgtaccac gcatcattac tgtacacctt tgggcttagg tctagatgtc   2940
cacataaata attatgtggg cctagagacc tggcccacat tgttttgcct gttctgctat   3000
caccctcaat gacaatactt atgggtctcc atggccgcgc agcggaatac acgacgttct   3060
cggcgaccca ctcttcaagt tcatctggaa cttgattaaa agaagaagaa agaaatggag   3120
aaacataaac ttctaaagga ggactaaaaa tcctatctaa atttgaactt aaattatgaa   3180
attgtaaaat atagtccttt ggggccttct cttttaatat attgagggcc tcggatttac   3240
tgcctgaatt gagtgcttcg gcatatgcgt cgttggcaga ttgctgacct cctctagctg   3300
atctgccatc gatttggaaa actccaaaat caatgaagtc tccgtctttc tccacgtagg   3360
tcttgacatc tgttgagctc caccgcggtg gcggccgctc tagaactagt ggatcccccg   3420
ggctgcagga attcgatgga tccaaggaga tataacaatg aagactaatc tttttctctt   3480
tctcatcttt tcacttctcc tatcattatc ctcggccgaa ttcagtaaag gagaagaact   3540
tttcactgga gttgtcccaa ttcttgttga attagatggt gatgttaatg ggcacaaatt   3600
```

-continued

```
ttctgtcagt ggagagggtg aaggtgatgc aacatacgga aaacttaccc ttaaatttat   3660
ttgcactact ggaaaactac ctgttccatg gccaacactt gtcactactt tctcttatgg   3720
tgttcaatgc ttttcaagat acccagatca tatgaagcgg cacgacttct tcaagagcgc   3780
catgcctgag ggatacgtgc aggagaggac catcttcttc aaggacgacg ggaactacaa   3840
gacacgtgct gaagtcaagt ttgagggaga caccctcgtc aacaggatcg agcttaaggg   3900
aatcgatttc aaggaggacg gaaacatcct cggccacaag ttggaataca actacaactc   3960
ccacaacgta tacatcatgg ccgacaagca aaagaacggc atcaaagcca acttcaagac   4020
ccgccacaac atcgaagacg gcggcgtgca actcgctgat cattatcaac aaaatactcc   4080
aattggcgat ggccctgtcc ttttaccaga caaccattac ctgtccacac aatctgccct   4140
ttcgaaagat cccaacgaaa agagagacca catggtcctt cttgagtttg taacagctgc   4200
tgggattaca catggcatgg atgaactata caaacatgat gagctttaag agctcatcaa   4260
gcttatcgat accgtcgacc tcgagggggg gcccggtacc cagcttttgt tccctttagt   4320
gagggttaat tgcgcgcttg gcgtaatcat ggtcatagct gtttcctgtg tgaaattgtt   4380
atccgctcac aattccacac aacatacgag ccggaagcat aaagtgtaaa gcctggggtg   4440
cctaatgagt gagctaactc acattaattg cgttgcgctc actgcccgct ttccagtcgg   4500
gaaacctgtc gtgccagctg cattaatgaa tcggccaacg cgcggggaga ggcggtttgc   4560
gtattgggcg ctcttccgct tcctcgctca ctgactcgct gcgctcggtc gttcggctgc   4620
ggcgagcggt atcagctcac tcaaaggcgg taatacggtt atccacagaa tcaggggata   4680
acgcaggaaa gaacatgtga gcaaaaggcc agcaaaaggc caggaaccgt aaaaaggccg   4740
cgttgctggc gtttttccat aggctccgcc cccctgacga gcatcacaaa aatcgacgct   4800
caagtcagag gtggcgaaac ccgacaggac tataaagata ccaggcgttt ccccctggaa   4860
gctccctcgt gcgctctcct gttccgaccc tgccgcttac cggatacctg tccgcctttc   4920
tcccttcggg aagcgtggcg ctttctcata gctcacgctg taggtatctc agttcggtgt   4980
aggtcgttcg ctccaagctg ggctgtgtgc acgaaccccc cgttcagccc gaccgctgcg   5040
ccttatccgg taactatcgt cttgagtcca acccggtaag acacgactta tcgccactgg   5100
cagcagccac tggtaacagg attagcagag cgaggtatgt aggcggtgct acagagttct   5160
tgaagtggtg gcctaactac ggctacacta gaaggacagt atttggtatc tgcgctctgc   5220
tgaagccagt taccttcgga aaaagagttg gtagctcttg atccggcaaa caaaccaccg   5280
ctggtagcgg tggttttttt gtttgcaagc agcagattac gcgcagaaaa aaaggatctc   5340
aagaagatcc tttgatcttt tctacggggt ctgacgctca gtggaacgaa aactcacgtt   5400
aagggatttt ggtcatgaga ttatcaaaaa ggatcttcac ctagatcctt ttaaattaaa   5460
aatgaagttt taaatcaatc taaagtatat atgagtaaac ttggtctgac agttaccaat   5520
gcttaatcag tgaggcacct atctcagcga tctgtctatt tcgttcatcc atagttgcct   5580
gactccccgt cgtgtagata actacgatac gggagggctt accatctggc cccagtgctg   5640
caatgatacc gcgagaccca cgctcaccgg ctccagattt atcagcaata aaccagccag   5700
ccggaagggc cgagcgcaga agtggtcctg caactttatc cgcctccatc cagtctatta   5760
attgttgccg ggaagctaga gtaagtagtt cgccagttaa tagtttgcgc aacgttgttg   5820
ccattgctac aggcatcgtg gtgtcacgct cgtcgtttgg tatggcttca ttcagctccg   5880
gttcccaacg atcaaggcga gttacatgat cccccatgtt gtgcaaaaaa gcggttagct   5940
```

ccttcggtcc tccgatcgtt gtcagaagta agttggccgc agtgttatca ctcatggtta 6000
tggcagcact gcataattct cttactgtca tgccatccgt aagatgcttt tctgtgactg 6060
gtgagtactc aaccaagtca ttctgagaat agtgtatgcg gcgaccgagt tgctcttgcc 6120
cggcgtcaat acgggataat accgcgccac atagcagaac tttaaaagtg ctcatcattg 6180
gaaaacgttc ttcggggcga aaactctcaa ggatcttacc gctgttgaga tccagttcga 6240
tgtaacccac tcgtgcaccc aactgatctt cagcatcttt tactttcacc agcgtttctg 6300
ggtgagcaaa aacaggaagg caaaatgccg caaaaaaggg aataagggcga cacggaaatg 6360 ttgaatactc atactcttcc tttttcaata ttattgaagc atttatcagg gttattgtct 6420
catgagcgga tacatatttg aatgtattta gaaaaataaa caaatagggg ttccgcgcac 6480
atttccccga aaagtgccac 6500

<210> SEQ ID NO 11
<211> LENGTH: 4675
<212> TYPE: DNA
<213> ORGANISM: Artificial sequence
<220> FEATURE:
<223> OTHER INFORMATION: IL-60-BS-amp
<220> FEATURE:
<221> NAME/KEY: misc_feature
<222> LOCATION: (1377)..(1377)
<223> OTHER INFORMATION: n is a, c, g, or t
<220> FEATURE:
<221> NAME/KEY: misc_feature
<222> LOCATION: (1404)..(1404)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1480)..(1480)
<223> OTHER INFORMATION: n is a, c, g, or t
<220> FEATURE:
<221> NAME/KEY: misc_feature
<222> LOCATION: (1495)..(1495)
<223> OTHER INFORMATION: n is a, c, g, or t
<220> FEATURE:
<221> NAME/KEY: misc_feature
<222> LOCATION: (1566)..(1566)
<223> OTHER INFORMATION: n is a, c, g, or t
<220> FEATURE:
<221> NAME/KEY: misc_feature
<222> LOCATION: (1573)..(1573)
<223> OTHER INFORMATION: n is a, c, g, or t
<220> FEATURE:
<221> NAME/KEY: misc_feature
<222> LOCATION: (1580)..(1580)
<223> OTHER INFORMATION: n is a, c, g, or t
<220> FEATURE:
<221> NAME/KEY: misc_feature
<222> LOCATION: (1607)..(1607)
<223> OTHER INFORMATION: n is a, c, g, or t
<220> FEATURE:
<221> NAME/KEY: misc_feature
<222> LOCATION: (1632)..(1632)
<223> OTHER INFORMATION: n is a, c, g, or t
<220> FEATURE:
<221> NAME/KEY: misc_feature
<222> LOCATION: (1643)..(1644)
<223> OTHER INFORMATION: n is a, c, g, or t
<220> FEATURE:
<221> NAME/KEY: misc_feature
<222> LOCATION: (2490)..(2490)
<223> OTHER INFORMATION: n is a, c, g, or t

<400> SEQUENCE: 11
ctgacgcgcc ctgtagcggc gcattaagcg cggcgggtgt ggtggttacg cgcagcgtga 60

-continued

```
ccgctacact tgccagcgcc ctagcgcccg ctcctttcgc tttcttccct tcctttctcg    120
ccacgttcgc cggctttccc cgtcaagctc taaatcgggg gctcccttta gggttccgat    180
ttagtgcttt acggcacctc gaccccaaaa aacttgatta gggtgatggt tcacgtagtg    240
ggccatcgcc ctgatagacg gtttttcgcc ctttgacgtt ggagtccacg ttctttaata    300
gtggactctt gttccaaact ggaacaacac tcaaccctat ctcggtctat tcttttgatt    360
tataagggat tttgccgatt tcggcctatt ggttaaaaaa tgagctgatt taacaaaaat    420
ttaacgcgaa ttttaacaaa atattaacgc ttacaatttc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctctt    660
agctgcctga atgttcggat ggaaatgtgc tgacctgttt ggtgatacca ggtcgaagaa    720
ccgttggttc ttacattggt atttgccttc gaattggata agcacatgga gatgtggttc    780
cccattctcg tggagttctc tgcaaacttt gatgtatttt ttatttgttg gggtttctag    840
gtttttttaat tgggaaagtg cttcctcttt agagagagaa caattgggat atgttaggaa    900
ataatttttg gcatatattt taaataaacg aggcatgttg aaatgaatcg gtgtctctca    960
aagctctatg gcaatcggtg tatcggtgtc ttacttatac ctggacacct aatggctatt   1020
tggtaatttc ataaatgttc attgcaattc aaaattcaaa attcaaaaat caaatcttta   1080
aagcggccat ccgtataata ttaccggatg gccgcgcctt ttgtttttat gtggtcccca   1140
cgagggttac acagacgtca ctgtcaacca atcaaattgc attctcaaac gttagataag   1200
tgttcatttg tctttatata cttggtcccc aagttttttg tcttgcaata tgtgggaccc   1260
acttcttaat gaatttcctg aatctgttca cggatttcgt tgtatgttag ctattaaata   1320
tttgcagtcc gttgaggaaa cttacgagcc caatacattg ggccacgatt taattangga   1380
tcttatatct gttgtaaggg cccngtgact atgtcgaanc gaccaggcga tataatcatt   1440
tccacgcccg tctcgaaggt tcgccgaagg ctgaacttcn acggcccata caggnccatg   1500
taccgaaagc ccagaaatac agaatgtatc gaagccctga tgttccccgt ggatgtgaag   1560
gccccnttaa agnccagtcn tatgagcaac gggatgatat taagcancct ggtattgttc   1620
ggttgtgtta gngatgttac tcnnggatct ggaattactc acagagtggg taagaggttc   1680
tgtgttaaat cgatatattt tttaggtaaa gtctggatgg atgaaaatat caagaagcag   1740
aatcacacta atcaggtcat gttcttcttg gtccgtgata gaaggcccta tggaaacagc   1800
ccaatggatt ttggacaggt ttttaatatg ttcgataatg agcccagtac cgcaaccgtg   1860
aagaatgatt tgcgtgatag gtttcaagtg atgaggaaat ttcatgctac agttattggt   1920
gggccctctg gaatgaagga acaggcatta gttaagagat tttttaaaat taacagtcat   1980
gtaacttata atcatcagga ggcagcaaag tacgagaacc atactgaaaa cgccttgtta   2040
ttgtatatgg catgtacgca tgcctctaat ccagtgtatg caactatgaa aatacgcatc   2100
tatttctatg attcaatatc aaattaataa aatttatatt ttatatcatg agtttctgtt   2160
acatttattg tgttttcaag tacatcatac aatacatgat caactgctct gattacattg   2220
ttaatggaaa ttacaccaag actatctaaa tacttaagaa cttcatatct aaatactctt   2280
aagaaatgac cagtctgagg ctgtaatgtc gtccaaattc ggaagttgag aaaacatttg   2340
tgaatcccca ttaccttcct gatgttgtgg ttgaatctta tctgaatgga aatgatgtcg   2400
```

-continued

```
tggttcatta gaaatggcct ctggctgtgt tctgttatct tgaaatagag ggggattgtt   2460
atctcccaga taaaaacgcc attctctgcn tgaggagcag tgatgagttc ccctgtgcgt   2520
gaatccatga ttattgcagt tgaggtggag gtagtatgag cagccacagt ctaggtctac   2580
acgcttacgc cttattggtt tcttcttggc tatcttgtgt tggaccttga ttgatacttg   2640
cgaacagtgg ctcgtagagg gtgacgaagg ttgcattctt gagagcccaa tttttcaagg   2700
atatgttttt ttcttcgtct agatattccc tatatgatga ggtaggtcct ggattgcaga   2760
ggaagatagt gggaattccc cctttaattt gaatgggctt cccgtacttt gtgttgcttt   2820
gccagtccct ctgggccccc atgaattcct tgaagtgctt taaataatgc gggtctacgt   2880
catcaatgac gttgtaccac gcatcattac tgtacacctt tgggcttagg tctagatgtc   2940
cacataaata attatgtggg cctagagacc tggcccacat tgttttgcct gttctgctat   3000
caccctcaat gacaatactt atgggtctcc atggccgcgc agcggaatac acgacgttct   3060
cggcgaccca ctcttcaagt tcatctggaa cttgattaaa agaagaagaa agaaatggag   3120
aaacataaac ttctaaagga ggactaaaaa tcctatctaa atttgaactt aaattatgaa   3180
attgtaaaat atagtccttt ggggccttct cttttaatat attgagggcc tcggatttac   3240
tgcctgaatt gagtgcttcg gcatatgcgt cgttggcaga ttgctgacct cctctagctg   3300
atctgccatc gatttggaaa actccaaaat caatgaagtc tccgtctttc tccacgtagg   3360
tcttgacatc tgttgagctc caccgcggtg gcggccgctc tagaactagt ggatcccccg   3420
ggctgcagga attcgatatc aagcttatcg ataccgtcga cctcgagggg gggcccggta   3480
cccagctttt gttcccttta gtgagggtta attgcgcgct tggcgtaatc atggtcatag   3540
ctgtttcctg tgtgaaattg ttatccgctc acaattccac acaacatacg agccggaagc   3600
ataaagtgta aagcctgggg tgcctaatga gtgagctaac tcacattaat tgcgttgcgc   3660
tcactgcccg ctttccagtc gggaaacctg tcgtgccagc tgcattaatg aatcggccaa   3720
cgcgcgggga gaggcggttt gcgtattggg cgctcttccg cttcctcgct cactgactcg   3780
ctgcgctcgg tcgttcggct gcggcgagcg gtatcagctc actcaaaggc ggtaatacgg   3840
ttatccacag aatcagggga taacgcagga aagaacatgt gagcaaaagg ccagcaaaag   3900
gccaggaacc gtaaaaaggc cgcgttgctg gcgtttttcc ataggctccg cccccctgac   3960
gagcatcaca aaaatcgacg ctcaagtcag aggtggcgaa acccgacagg actataaaga   4020
taccaggcgt ttccccctgg aagctccctc gtgcgctctc ctgttccgac cctgccgctt   4080
accggatacc tgtccgcctt tctcccttcg ggaagcgtgg cgctttctca tagctcacgc   4140
tgtaggtatc tcagttcggt gtaggtcgtt cgctccaagc tgggctgtgt gcacgaaccc   4200
cccgttcagc ccgaccgctg cgccttatcc ggtaactatc gtcttgagtc caacccggta   4260
agacacgact tatcgccact ggcagcagcc actggtaaca ggattagcag agcgaggtat   4320
gtaggcggtg ctacagagtt cttgaagtgg tggcctaact acggctacac tagaaggaca   4380
gtatttggta tctgcgctct gctgaagcca gttaccttcg gaaaaagagt tggtagctct   4440
tgatccggca aacaaaccac cgctggtagc ggtggttttt ttgtttgcaa gcagcagatt   4500
acgcgcagaa aaaaaggatc tcaagaagat cctttgatct tttctacggg gtctgacgct   4560
cagtggaacg aaaactcacg ttaagggatt ttggtcatga gcggatacat atttgaatgt   4620
atttagaaaa ataaacaaat aggggttccg cgcacatttc cccgaaaagt gccac        4675
```

<210> SEQ ID NO 12
<211> LENGTH: 6500

<212> TYPE: DNA
<213> ORGANISM: Artificial sequence
<220> FEATURE:
<223> OTHER INFORMATION: IL-60-BS-GUS-amp
<220> FEATURE:
<221> NAME/KEY: misc_feature
<222> LOCATION: (1377)..(1377)
<223> OTHER INFORMATION: n is a, c, g, or t
<220> FEATURE:
<221> NAME/KEY: misc_feature
<222> LOCATION: (1404)..(1404)
<223> OTHER INFORMATION: n is a, c, g, or t
<220> FEATURE:
<221> NAME/KEY: misc_feature
<222> LOCATION: (1419)..(1419)
<223> OTHER INFORMATION: n is a, c, g, or t
<220> FEATURE:
<221> NAME/KEY: misc_feature
<222> LOCATION: (1480)..(1480)
<223> OTHER INFORMATION: n is a, c, g, or t
<220> FEATURE:
<221> NAME/KEY: misc_feature
<222> LOCATION: (1495)..(1495)
<223> OTHER INFORMATION: n is a, c, g, or t
<220> FEATURE:
<221> NAME/KEY: misc_feature
<222> LOCATION: (1566)..(1566)
<223> OTHER INFORMATION: n is a, c, g, or t
<220> FEATURE:
<221> NAME/KEY: misc_feature
<222> LOCATION: (1573)..(1573)
<223> OTHER INFORMATION: n is a, c, g, or t
<220> FEATURE:
<221> NAME/KEY: misc_feature
<222> LOCATION: (1580)..(1580)
<223> OTHER INFORMATION: n is a, c, g, or t
<220> FEATURE:
<221> NAME/KEY: misc_feature
<222> LOCATION: (1607)..(1607)
<223> OTHER INFORMATION: n is a, c, g, or t
<220> FEATURE:
<221> NAME/KEY: misc_feature
<222> LOCATION: (1632)..(1632)
<223> OTHER INFORMATION: n is a, c, g, or t
<220> FEATURE:
<221> NAME/KEY: misc_feature
<222> LOCATION: (1643)..(1644)
<223> OTHER INFORMATION: n is a, c, g, or t
<220> FEATURE:
<221> NAME/KEY: misc_feature
<222> LOCATION: (2490)..(2490)
<223> OTHER INFORMATION: n is a, c, g, or t

<400> SEQUENCE: 12
ctgacgcgcc ctgtagcggc gcattaagcg cggcgggtgt ggtggttacg cgcagcgtga 60
ccgctacact tgccagcgcc ctagcgcccg ctcctttcgc tttcttccct tcctttctcg 120
ccacgttcgc cggctttccc cgtcaagctc taaatcgggg gctcccttta gggttccgat 180
ttagtgcttt acggcacctc gaccccaaaa aacttgatta gggtgatggt tcacgtagtg 240
ggccatcgcc ctgatagacg gtttttcgcc ctttgacgtt ggagtccacg ttctttaata 300
gtggactctt gttccaaact ggaacaacac tcaaccctat ctcggtctat tcttttgatt 360
tataagggat tttgccgatt tcggcctatt ggttaaaaaa tgagctgatt taacaaaaat 420
ttaacgcgaa ttttaacaaa atattaacgc ttacaatttc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgcgtaata cgactcacta tagggcgaat tggagctctt 660
agctgcctga atgttcggat ggaaatgtgc tgacctgttt ggtgatacca ggtcgaagaa 720

-continued

```
ccgttggttc ttacattggt atttgccttc gaattggata agcacatgga gatgtggttc    780
cccattctcg tggagttctc tgcaaacttt gatgtatttt ttatttgttg gggtttctag    840
gtttttttaat tgggaaagtg cttcctcttt agagagagaa caattgggat atgttaggaa   900
ataatttttg gcatatattt taaataaacg aggcatgttg aaatgaatcg gtgtctctca    960
aagctctatg gcaatcggtg tatcggtgtc ttacttatac ctggacacct aatggctatt   1020
tggtaatttc ataaatgttc attgcaattc aaaattcaaa attcaaaaat caaatcttta   1080
aagcggccat ccgtataata ttaccggatg gccgcgcctt ttgtttttat gtggtcccca   1140
cgagggttac acagacgtca ctgtcaacca atcaaattgc attctcaaac gttagataag   1200
tgttcatttg tctttatata cttggtcccc aagttttttg tcttgcaata tgtgggaccc   1260
acttcttaat gaatttcctg aatctgttca cggatttcgt tgtatgttag ctattaaata   1320
tttgcagtcc gttgaggaaa cttacgagcc caatacattg ggccacgatt taattangga   1380
tcttatatct gttgtaaggg cccngtgact atgtcgaanc gaccaggcga tataatcatt   1440
tccacgcccg tctcgaaggt tcgccgaagg ctgaacttcn acggcccata caggnccatg   1500
taccgaaagc ccagaaatac agaatgtatc gaagccctga tgttccccgt ggatgtgaag   1560
gccccnttaa agnccagtcn tatgagcaac gggatgatat taagcancct ggtattgttc   1620
ggttgtgtta gngatgttac tcnnggatct ggaattactc acagagtggg taagaggttc   1680
tgtgttaaat cgatatattt tttaggtaaa gtctggatgg atgaaaatat caagaagcag   1740
aatcacacta atcaggtcat gttcttcttg gtccgtgata gaaggcccta tggaaacagc   1800
ccaatggatt ttggacaggt ttttaatatg ttcgataatg agcccagtac cgcaaccgtg   1860
aagaatgatt tgcgtgatag gtttcaagtg atgaggaaat ttcatgctac agttattggt   1920
gggccctctg gaatgaagga acaggcatta gttaagagat tttttaaaat taacagtcat   1980
gtaacttata atcatcagga ggcagcaaag tacgagaacc atactgaaaa cgccttgtta   2040
ttgtatatgg catgtacgca tgcctctaat ccagtgtatg caactatgaa aatacgcatc   2100
tatttctatg attcaatatc aaattaataa aatttatatt ttatatcatg agtttctgtt   2160
acatttattg tgttttcaag tacatcatac aatacatgat caactgctct gattacattg   2220
ttaatggaaa ttacaccaag actatctaaa tacttaagaa cttcatatct aaatactctt   2280
aagaaatgac cagtctgagg ctgtaatgtc gtccaaattc ggaagttgag aaaacatttg   2340
tgaatcccca ttaccttcct gatgttgtgg ttgaatctta tctgaatgga aatgatgtcg   2400
tggttcatta gaaatggcct ctggctgtgt tctgttatct tgaaatagag ggggattgtt   2460
atctcccaga taaaaacgcc attctctgcn tgaggagcag tgatgagttc ccctgtgcgt   2520
gaatccatga ttattgcagt tgaggtggag gtagtatgag cagccacagt ctaggtctac   2580
acgcttacgc cttattggtt tcttcttggc tatcttgtgt tggaccttga ttgatacttg   2640
cgaacagtgg ctcgtagagg gtgacgaagg ttgcattctt gagagcccaa tttttcaagg   2700
atatgttttt ttcttcgtct agatattccc tatatgatga ggtaggtcct ggattgcaga   2760
ggaagatagt gggaattccc cctttaattt gaatgggctt cccgtacttt gtgttgcttt   2820
gccagtccct ctgggccccc atgaattcct tgaagtgctt taaataatgc gggtctacgt   2880
catcaatgac gttgtaccac gcatcattac tgtacacctt tgggcttagg tctagatgtc   2940
cacataaata attatgtggg cctagagacc tggcccacat tgttttgcct gttctgctat   3000
caccctcaat gacaatactt atgggtctcc atggccgcgc agcggaatac acgacgttct   3060
cggcgaccca ctcttcaagt tcatctggaa cttgattaaa agaagaagaa agaaatggag   3120
```

-continued

```
aaacataaac ttctaaagga ggactaaaaa tcctatctaa atttgaactt aaattatgaa   3180

attgtaaaat atagtccttt ggggccttct cttttaatat attgagggcc tcggatttac   3240

tgcctgaatt gagtgcttcg gcatatgcgt cgttggcaga ttgctgacct cctctagctg   3300

atctgccatc gatttggaaa actccaaaat caatgaagtc tccgtctttc tccacgtagg   3360

tcttgacatc tgttgagctc caccgcggtg gcggccgctc tagaactagt ggatcccccg   3420

ggctgcagga attcgatgag ctcatgttac gtcctgtaga aaccccaacc cgtgaaatca   3480

aaaaactcga cggcctgtgg gcattcagtc tggatcgcga aaactgtgga attgatcagc   3540

gttggtggga aagcgcgtta caagaaagcc gggcaattgc tgtgccaggc agttttaacg   3600

atcagttcgc cgatgcagat attcgtaatt atgcgggcaa cgtctggtat cagcgcgaag   3660

tctttatacc gaaaggttgg gcaggccagc gtatcgtgct gcgtttcgat gcggtcactc   3720

attacggcaa agtgtgggtc aataatcagg aagtgatgga gcatcagggc ggctatacgc   3780

catttgaagc cgatgtcacg ccgtatgtta ttgccgggaa aagtgtacgt atcaccgttt   3840

gtgtgaacaa cgaactgaac tggcagacta tcccgccggg aatggtgatt accgacgaaa   3900

acggcaagaa aaagcagtct tacttccatg atttctttaa ctatgccggg atccatcgca   3960

gcgtaatgct ctacaccacg ccgaacacct gggtggacga tatcaccgtg gtgacgcatg   4020

tcgcgcaaga ctgtaaccac gcgtctgttg actggcaggt ggtggccaat ggtgatgtca   4080

gcgttgaact gcgtgatgcg gatcaacagg tggttgcaac tggacaaggc actagcggga   4140

ctttgcaagt ggtgaatccg cacctctggc aaccgggtga aggttatctc tatgaactgt   4200

gcgtcacagc caaaagccag acagagtgtg atatctaccc gcttcgcgtc ggcatccggt   4260

cagtggcagt gaagggcgaa cagttcctga ttaaccacaa accgttctac tttactggct   4320

ttggtcgtca tgaagatgcg gacttacgtg gcaaaggatt cgataacgtg ctgatggtgc   4380

acgaccacgc attaatggac tggattgggg ccaactccta ccgtacctcg cattaccctt   4440

acgctgaaga gatgctcgac tgggcagatg aacatggcat cgtggtgatt gatgaaactg   4500

ctgctgtcgg ctttaacctc tctttaggca ttggtttcga agcgggcaac aagccgaaag   4560

aactgtacag cgaagaggca gtcaacgggg aaactcagca agcgcactta caggcgatta   4620

aagagctgat agcgcgtgac aaaaaccacc caagcgtggt gatgtggagt attgccaacg   4680

aaccggatac ccgtccgcaa gtgcacggga atatttcgcc actggcggaa gcaacgcgta   4740

aactcgaccc gacgcgtccg atcacctgcg tcaatgtaat gttctgcgac gctcacaccg   4800

ataccatcag cgatctcttt gatgtgctgt gcctgaaccg ttattacgga tggtatgtcc   4860

aaagcggcga tttggaaacg gcagagaagg tactggaaaa agaacttctg gcctggcagg   4920

agaaactgca tcagccgatt atcatcaccg aatacggcgt ggatacgtta gccgggctgc   4980

actcaatgta caccgacatg tggagtgaag agtatcagtg tgcatggctg gatatgtatc   5040

accgcgtctt tgatcgcgtc agcgccgtcg tcggtgaaca ggtatggaat ttcgccgatt   5100

ttgcgacctc gcaaggcata ttgcgcgttg gcggtaacaa gaaagggatc ttcactcgcg   5160

accgcaaacc gaagtcggcg gcttttctgc tgcaaaaacg ctggactggc atgaacttcg   5220

gtgaaaaacc gcagcaggga ggcaaacagt cgacatcaag cttatcaagc ttatcgatac   5280

cgtcgacctc gagggggggc ccggtaccca gcttttgttc cctttagtga gggttaattg   5340

cgcgcttggc gtaatcatgg tcatagctgt ttcctgtgtg aaattgttat ccgctcacaa   5400

ttccacacaa catacgagcc ggaagcataa agtgtaaagc ctggggtgcc taatgagtga   5460
```

```
gctaactcac attaattgcg ttgcgctcac tgcccgcttt ccagtcggga aacctgtcgt   5520

gccagctgca ttaatgaatc ggccaacgcg cggggagagg cggtttgcgt attgggcgct   5580

cttccgcttc ctcgctcact gactcgctgc gctcggtcgt tcggctgcgg cgagcggtat   5640

cagctcactc aaaggcggta atacggttat ccacagaatc aggggataac gcaggaaaga   5700

acatgtgagc aaaaggccag caaaaggcca ggaaccgtaa aaaggccgcg ttgctggcgt   5760

ttttccatag gctccgcccc cctgacgagc atcacaaaaa tcgacgctca agtcagaggt   5820

ggcgaaaccc gacaggacta taaagatacc aggcgtttcc ccctggaagc tccctcgtgc   5880

gctctcctgt tccgaccctg ccgcttaccg gatacctgtc cgcctttctc ccttcgggaa   5940

gcgtggcgct ttctcatagc tcacgctgta ggtatctcag ttcggtgtag gtcgttcgct   6000

ccaagctggg ctgtgtgcac gaaccccccg ttcagcccga ccgctgcgcc ttatccggta   6060

actatcgtct tgagtccaac ccggtaagac acgacttatc gccactggca gcagccactg   6120

gtaacaggat tagcagagcg aggtatgtag gcggtgctac agagttcttg aagtggtggc   6180

ctaactacgg ctacactaga aggacagtat ttggtatctg cgctctgctg aagccagtta   6240

ccttcggaaa aagagttggt agctcttgat ccggcaaaca aaccaccgct ggtagcggtg   6300

gtttttttgt ttgcaagcag cagattacgc gcagaaaaaa aggatctcaa gaagatcctt   6360

tgatcttttc tacggggtct gacgctcagt ggaacgaaaa ctcacgttaa gggattttgg   6420

tcatgagcgg atacatattt gaatgtattt agaaaaataa acaaataggg gttccgcgca   6480

catttccccg aaaagtgcca                                                6500


<210> SEQ ID NO 13
<211> LENGTH: 6035
<212> TYPE: DNA
<213> ORGANISM: Artificial sequence
<220> FEATURE:
<223> OTHER INFORMATION: IR-GUS-pD
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t

<400> SEQUENCE: 13

gcgcccaata cgcaaaccgc ctctccccgc gcgttggccg attcattaat gcagctggca     60

cgacaggttt cccgactgga aagcgggcag tgagcgcaac gcaattaatg tgagttagct    120

cactcattag gcaccccagg ctttacactt tatgcttccg gctcgtatgt tgtgtggaat    180

tgtgagcgga taacaatttc acacaggaaa cagctatgac catgattacg ccaagctcta    240

atacgactca ctatagggaa agctcggtac cacgcatgct gcagacgcgt tacgtatcgg    300

atccagaatt cgtgatatct gaattcatac ctggacacct aatggctatt tggtaatttc    360

ataaatgttc attgcaattc aaaattcaaa attcaaaaat caaatcttta aagcggccat    420

ccgtataata ttaccggatg gccgcgcctt ttgtttttat gtggtcccca cgagggttac    480

acagacgtca ctgtcaacca atcaaattgc attctcaaac gttagataag tgttcatttg    540

tctttatata cttggtcccc aagtttttg tcttgcaata tgtgggaccc acttcttaat     600

gaatttcctg aatctgttca cggatttcgt tgtatgttag ctattaaata tttgcagtcc    660

gttgaggaaa cttacgagcc caatacattg ggccacgatt taattangga tcttatatct    720

gttgtaaggg cccngtgacg aattcgtcga catgttacgt cctgtagaaa ccccaacccg    780
```

-continued

```
tgaaatcaaa aaactcgacg gcctgtgggc attcagtctg gatcgcgaaa actgtggaat    840
tgatcagcgt tggtgggaaa gcgcgttaca agaaagccgg gcaattgctg tgccaggcag    900
ttttaacgat cagttcgccg atgcagatat tcgtaattat gcgggcaacg tctggtatca    960
gcgcgaagtc tttataccga aaggttgggc aggccagcgt atcgtgctgc gtttcgatgc   1020
ggtcactcat tacggcaaag tgtgggtcaa taatcaggaa gtgatggagc atcagggcgg   1080
ctatacgcca tttgaagccg atgtcacgcc gtatgttatt gccgggaaaa gtgtacgtat   1140
caccgtttgt gtgaacaacg aactgaactg gcagactatc ccgccgggaa tggtgattac   1200
cgacgaaaac ggcaagaaaa agcagtctta cttccatgat ttctttaact atgccgggat   1260
ccatcgcagc gtaatgctct acaccacgcc gaacacctgg gtggacgata tcaccgtggt   1320
gacgcatgtc gcgcaagact gtaaccacgc gtctgttgac tggcaggtgg tggccaatgg   1380
tgatgtcagc gttgaactgc gtgatgcgga tcaacaggtg gttgcaactg gacaaggcac   1440
tagcgggact ttgcaagtgg tgaatccgca cctctggcaa ccgggtgaag gttatctcta   1500
tgaactgtgc gtcacagcca aaagccagac agagtgtgat atctacccgc ttcgcgtcgg   1560
catccggtca gtggcagtga agggcgaaca gttcctgatt aaccacaaac cgttctactt   1620
tactggcttt ggtcgtcatg aagatgcgga cttacgtggc aaaggattcg ataacgtgct   1680
gatggtgcac gaccacgcat taatggactg gattggggcc aactcctacc gtacctcgca   1740
ttacccttac gctgaagaga tgctcgactg ggcagatgaa catggcatcg tggtgattga   1800
tgaaactgct gctgtcggct ttaacctctc tttaggcatt ggtttcgaag cgggcaacaa   1860
gccgaaagaa ctgtacagcg aagaggcagt caacggggaa actcagcaag cgcacttaca   1920
ggcgattaaa gagctgatag cgcgtgacaa aaaccaccca agcgtggtga tgtggagtat   1980
tgccaacgaa ccggataccc gtccgcaagt gcacgggaat atttcgccac tggcggaagc   2040
aacgcgtaaa ctcgacccga cgcgtccgat cacctgcgtc aatgtaatgt tctgcgacgc   2100
tcacaccgat accatcagcg atctctttga tgtgctgtgc ctgaaccgtt attacggatg   2160
gtatgtccaa agcggcgatt tggaaacggc agagaaggta ctggaaaaag aacttctggc   2220
ctggcaggag aaactgcatc agccgattat catcaccgaa tacggcgtgg atacgttagc   2280
cgggctgcac tcaatgtaca ccgacatgtg gagtgaagag tatcagtgtg catggctgga   2340
tatgtatcac cgcgtctttg atcgcgtcag cgccgtcgtc ggtgaacagg tatggaattt   2400
cgccgatttt gcgacctcgc aaggcatatt gcgcgttggc ggtaacaaga aagggatctt   2460
cactcgcgac cgcaaaccga agtcggcggc ttttctgctg caaaaacgct ggactggcat   2520
gaacttcggt gaaaaaccgc agcagggagg caaacagtcg acatcagctc gcggccgctg   2580
tattctatag tgtcacctaa atggccgcac aattcactgg ccgtcgtttt acaacgtcgt   2640
gactgggaaa accctggcgt tacccaactt aatcgccttg cagcacatcc ccctttcgcc   2700
agctggcgta atagcgaaga ggcccgcacc gatcgccctt cccaacagtt gcgcagcctg   2760
aatggcgaat ggaaattgta agcgttaata ttttgttaaa attcgcgtta aatttttgtt   2820
aaatcagctc attttttaac caataggccg aaatcggcaa aatcccttat aaatcaaaag   2880
aatagaccga gatagggttg agtgttgttc cagtttggaa caagagtcca ctattaaaga   2940
acgtggactc caacgtcaaa gggcgaaaaa ccgtctatca gggcgatggc ccactacgtg   3000
aaccatcacc ctaatcaagt tttttggggt cgaggtgccg taaagcacta aatcggaacc   3060
ctaaagggag cccccgattt agagcttgac ggggaaagcc ggcgaacgtg gcgagaaagg   3120
```

-continued aagggaagaa agcgaaagga gcgggcgcta gggcgctggc aagtgtagcg gtcacgctgc 3180
gcgtaaccac cacacccgcc gcgcttaatg cgccgctaca gggcgcgtca ggtggcactt 3240
ttcggggaaa tgtgcgcgga acccctattt gtttattttt ctaaatacat tcaaatatgt 3300
atccgctcat gagacaataa ccctgataaa tgcttcaata atattgaaaa aggaagagta 3360
tgagtattca acatttccgt gtcgccctta ttcccttttt tgcggcattt tgccttcctg 3420
tttttgctca cccagaaacg ctggtgaaag taaaagatgc tgaagatcag ttgggtgcac 3480
gagtgggtta catcgaactg gatctcaaca gcggtaagat ccttgagagt tttcgccccg 3540
aagaacgttt tccaatgatg agcactttta aagttctgct atgtggcgcg gtattatccc 3600
gtattgacgc cgggcaagag caactcggtc gccgcataca ctattctcag aatgacttgg 3660
ttgagtactc accagtcaca gaaaagcatc ttacggatgg catgacagta agagaattat 3720
gcagtgctgc cataaccatg agtgataaca ctgcggccaa cttacttctg acaacgatcg 3780
gaggaccgaa ggagctaacc gcttttttgc acaacatggg ggatcatgta actcgccttg 3840
atcgttggga accggagctg aatgaagcca taccaaacga cgagcgtgac accacgatgc 3900
ctgtagcaat ggcaacaacg ttgcgcaaac tattaactgg cgaactactt actctagctt 3960
cccggcaaca attaatagac tggatggagg cggataaagt tgcaggacca cttctgcgct 4020
cggcccttcc ggctggctgg tttattgctg ataaatctgg agccggtgag cgtgggtctc 4080
gcggtatcat tgcagcactg gggccagatg gtaagccctc ccgtatcgta gttatctaca 4140
cgacggggag tcaggcaact atggatgaac gaaatagaca gatcgctgag ataggtgcct 4200
cactgattaa gcattggtaa ctgtcagacc aagtttactc atatatactt tagattgatt 4260
taaaacttca tttttaattt aaaaggatct aggtgaagat cctttttgat aatctcatga 4320
acaataaaac tgtctgctta cataaacagt aatacaaggg gtgttatgag ccatattcaa 4380
cgggaaacgt cttgctctag gccgcgatta aattccaaca tggatgctga tttatatggg 4440
tataaatggg ctcgcgataa tgtcgggcaa tcaggtgcga caatctatcg attgtatggg 4500
aagcccgatg cgccagagtt gtttctgaaa catggcaaag gtagcgttgc caatgatgtt 4560
acagatgaga tggtcagact aaactggctg acggaattta tgcctcttcc gaccatcaag 4620
cattttatcc gtactcctga tgatgcatgg ttactcacca ctgcgatccc cgggaaaaca 4680
gcattccagg tattagaaga atatcctgat tcaggtgaaa atattgttga tgcgctggca 4740
gtgttcctgc gccggttgca ttcgattcct gtttgtaatt gtccttttaa cagcgatcgc 4800
gtatttcgtc tcgctcaggc gcaatcacga atgaataacg gtttggttga tgcgagtgat 4860
tttgatgacg agcgtaatgg ctggcctgtt gaacaagtct ggaaagaaat gcataaactt 4920
ttgccattct caccggattc agtcgtcact catggtgatt tctcacttga taaccttatt 4980
tttgacgagg ggaaattaat aggttgtatt gatgttggac gagtcggaat cgcagaccga 5040
taccaggatc ttgccatcct atggaactgc ctcggtgagt tttctccttc attacagaaa 5100
cggctttttc aaaaatatgg tattgataat cctgatatga ataaattgca gtttcatttg 5160
atgctcgatg agtttttcta agaattaatt catgaccaaa atcccttaac gtgagttttc 5220
gttccactga gcgtcagacc ccgtagaaaa gatcaaagga tcttcttgag atcctttttt 5280
tctgcgcgta atctgctgct tgcaaacaaa aaaaccaccg ctaccagcgg tggtttgttt 5340
gccggatcaa gagctaccaa ctctttttcc gaaggtaact ggcttcagca gagcgcagat 5400
accaaatact gtccttctag tgtagccgta gttaggccac cacttcaaga actctgtagc 5460
accgcctaca tacctcgctc tgctaatcct gttaccagtg gctgctgcca gtggcgataa 5520

```
gtcgtgtctt accgggttgg actcaagacg atagttaccg gataaggcgc agcggtcggg   5580

ctgaacgggg ggttcgtgca cacagcccag cttggagcga acgacctaca ccgaactgag   5640

atacctacag cgtgagctat gagaaagcgc cacgcttccc gaagggagaa aggcggacag   5700

gtatccggta agcggcaggg tcggaacagg agagcgcacg agggagcttc caggggggaaa  5760

cgcctggtat ctttatagtc ctgtcgggtt tcgccacctc tgacttgagc gtcgattttt   5820

gtgatgctcg tcaggggggc ggagcctatg gaaaaacgcc agcaacgcgg cctttttacg   5880

gttcctggcc ttttgctggc cttttgctca catgttcttt cctgcgttat cccctgattc   5940

tgtggataac cgtattaccg cctttgagtg agctgatacc gctcgccgca gccgaacgac   6000

cgagcgcagc gagtcagtga gcgaggaagc ggaag                              6035


<210> SEQ ID NO 14
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 14

acaggcccat agaccgaaag ccca                                            24


<210> SEQ ID NO 15
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 15

tgggctgtcg aagttcagcc t                                               21


<210> SEQ ID NO 16
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 16

gaaggctgaa cttcgacag                                                  19


<210> SEQ ID NO 17
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 17

attgggctgt ttccataggg c                                               21


<210> SEQ ID NO 18
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 18

agagacaccg attcatttca ac                                              22
```

<210> SEQ ID NO 19
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 19
gcggataaca atttcacaca g 21

<210> SEQ ID NO 20
<211> LENGTH: 39
<212> TYPE: DNA
<213> ORGANISM: Artificial sequence
<220> FEATURE:
<223> OTHER INFORMATION: Single strand DNA oligonucleotide

<400> SEQUENCE: 20
ggctgaactt cgacagccca tacagcagcc gtgctgctg 39

<210> SEQ ID NO 21
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 21
gcggtactgg gctcattata tcgaacatat t 31

<210> SEQ ID NO 22
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 22
ggcttcgata cattctgtat ttctg 25

<210> SEQ ID NO 23
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 23
ctgatgttcc ccgtggatgt gaaggcccat 30

<210> SEQ ID NO 24
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 24
ccacgagtaa catcactaac aaccaacaat ac 32

<210> SEQ ID NO 25
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 25
ccacgagtaa catcactaac aaccaacaat ac 32

<210> SEQ ID NO 26
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 26
cagcgtaagg gtaatgcgag 20

<210> SEQ ID NO 27
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 27
ggccgaattc agtaaaggag aag 23

<210> SEQ ID NO 28
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 28
tgtgtggaca ggtaatgg 18

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29
atacttggac acctaatggc 20

<210> SEQ ID NO 30
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 30
agtcacgggc ccttacaa 18

<210> SEQ ID NO 31
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 31
gtcgccgcat acactattc 19

<210> SEQ ID NO 32

<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 32
actttatccg cctccatcc 19

<210> SEQ ID NO 33
<211> LENGTH: 4264
<212> TYPE: DNA
<213> ORGANISM: Artificial sequence
<220> FEATURE:
<223> OTHER INFORMATION: IR-pD
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t

<400> SEQUENCE: 33
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagctcta 240
atacgactca ctatagggaa agctcggtac cacgcatgct gcagacgcgt tacgtatcgg 300
atccagaatt cgtgatatct gaattcatac ctggacacct aatggctatt tggtaatttc 360
ataaatgttc attgcaattc aaaattcaaa attcaaaaat caaatcttta aagcggccat 420
ccgtataata ttaccggatg gccgcgcctt ttgtttttat gtggtcccca cgagggttac 480
acagacgtca ctgtcaacca atcaaattgc attctcaaac gttagataag tgttcatttg 540
tctttatata cttggtcccc aagtttttttg tcttgcaata tgtgggaccc acttcttaat 600
gaatttcctg aatctgttca cggatttcgt tgtatgttag ctattaaata tttgcagtcc 660
gttgaggaaa cttacgagcc caatacattg ggccacgatt taattangga tcttatatct 720
gttgtaaggg cccngtgacg tcgacaagct tctcgagcct aggctagctc tagaccacac 780
gtgtgggggc ccgagctcgc ggccgctgta ttctatagtg tcacctaaat ggccgcacaa 840
ttcactggcc gtcgttttac aacgtcgtga ctgggaaaac cctggcgtta cccaacttaa 900
tcgccttgca gcacatcccc ctttcgccag ctggcgtaat agcgaagagg cccgcaccga 960
tcgcccttcc caacagttgc gcagcctgaa tggcgaatgg aaattgtaag cgttaatatt 1020
ttgttaaaat tcgcgttaaa tttttgttaa atcagctcat tttttaacca ataggccgaa 1080
atcggcaaaa tcccttataa atcaaaagaa tagaccgaga tagggttgag tgttgttcca 1140
gtttggaaca agagtccact attaaagaac gtggactcca acgtcaaagg gcgaaaaacc 1200
gtctatcagg gcgatggccc actacgtgaa ccatcaccct aatcaagttt tttggggtcg 1260
aggtgccgta aagcactaaa tcggaaccct aaagggagcc cccgatttag agcttgacgg 1320
ggaaagccgg cgaacgtggc gagaaaggaa gggaagaaag cgaaaggagc gggcgctagg 1380
gcgctggcaa gtgtagcggt cacgctgcgc gtaaccacca cacccgccgc gcttaatgcg 1440
ccgctacagg gcgcgtcagg tggcactttt cggggaaatg tgcgcggaac ccctatttgt 1500
ttatttttct aaatacattc aaatatgtat ccgctcatga gacaataacc ctgataaatg 1560
cttcaataat attgaaaaag gaagagtatg agtattcaac atttccgtgt cgcccttatt 1620
ccctttttg cggcattttg ccttcctgtt tttgctcacc cagaaacgct ggtgaaagta 1680
aaagatgctg aagatcagtt gggtgcacga gtgggttaca tcgaactgga tctcaacagc 1740
ggtaagatcc ttgagagttt tcgccccgaa gaacgttttc caatgatgag cacttttaaa 1800
gttctgctat gtggcgcggt attatcccgt attgacgccg ggcaagagca actcggtcgc 1860
cgcatacact attctcagaa tgacttggtt gagtactcac cagtcacaga aaagcatctt 1920
acggatggca tgacagtaag agaattatgc agtgctgcca taaccatgag tgataacact 1980
gcggccaact tacttctgac aacgatcgga ggaccgaagg agctaaccgc ttttttgcac 2040
aacatggggg atcatgtaac tcgccttgat cgttgggaac cggagctgaa tgaagccata 2100
ccaaacgacg agcgtgacac cacgatgcct gtagcaatgg caacaacgtt gcgcaaacta 2160
ttaactggcg aactacttac tctagcttcc cggcaacaat taatagactg gatggaggcg 2220
gataaagttg caggaccact tctgcgctcg gcccttccgg ctggctggtt tattgctgat 2280
aaatctggag ccggtgagcg tgggtctcgc ggtatcattg cagcactggg gccagatggt 2340
aagccctccc gtatcgtagt tatctacacg acggggagtc aggcaactat ggatgaacga 2400
aatagacaga tcgctgagat aggtgcctca ctgattaagc attggtaact gtcagaccaa 2460
gtttactcat atatacttta gattgattta aaacttcatt tttaatttaa aaggatctag 2520
gtgaagatcc tttttgataa tctcatgaac aataaaactg tctgcttaca taaacagtaa 2580
tacaaggggt gttatgagcc atattcaacg ggaaacgtct tgctctaggc cgcgattaaa 2640
ttccaacatg gatgctgatt tatatgggta taaatgggct cgcgataatg tcgggcaatc 2700
aggtgcgaca atctatcgat tgtatgggaa gcccgatgcg ccagagttgt ttctgaaaca 2760
tggcaaaggt agcgttgcca atgatgttac agatgagatg gtcagactaa actggctgac 2820
ggaatttatg cctcttccga ccatcaagca ttttatccgt actcctgatg atgcatggtt 2880
actcaccact gcgatccccg ggaaaacagc attccaggta ttagaagaat atcctgattc 2940
aggtgaaaat attgttgatg cgctggcagt gttcctgcgc cggttgcatt cgattcctgt 3000
ttgtaattgt ccttttaaca gcgatcgcgt atttcgtctc gctcaggcgc aatcacgaat 3060
gaataacggt ttggttgatg cgagtgattt tgatgacgag cgtaatggct ggcctgttga 3120
acaagtctgg aaagaaatgc ataaactttt gccattctca ccggattcag tcgtcactca 3180
tggtgatttc tcacttgata accttatttt tgacgagggg aaattaatag gttgtattga 3240
tgttggacga gtcggaatcg cagaccgata ccaggatctt gccatcctat ggaactgcct 3300
cggtgagttt tctccttcat tacagaaacg gctttttcaa aaatatggta ttgataatcc 3360
tgatatgaat aaattgcagt ttcatttgat gctcgatgag tttttctaag aattaattca 3420
tgaccaaaat cccttaacgt gagttttcgt tccactgagc gtcagacccc gtagaaaaga 3480
tcaaaggatc ttcttgagat cctttttttc tgcgcgtaat ctgctgcttg caaacaaaaa 3540
aaccaccgct accagcggtg gtttgtttgc cggatcaaga gctaccaact ctttttccga 3600
aggtaactgg cttcagcaga gcgcagatac caaatactgt ccttctagtg tagccgtagt 3660
taggccacca cttcaagaac tctgtagcac cgcctacata cctcgctctg ctaatcctgt 3720
taccagtggc tgctgccagt ggcgataagt cgtgtcttac cgggttggac tcaagacgat 3780
agttaccgga taaggcgcag cggtcgggct gaacgggggg ttcgtgcaca cagcccagct 3840
tggagcgaac gacctacacc gaactgagat acctacagcg tgagctatga gaaagcgcca 3900

-continued

```
cgcttcccga agggagaaag gcggacaggt atccggtaag cggcagggtc ggaacaggag   3960

agcgcacgag ggagcttcca gggggaaacg cctggtatct ttatagtcct gtcgggtttc   4020

gccacctctg acttgagcgt cgatttttgt gatgctcgtc aggggggcgg agcctatgga   4080

aaaacgccag caacgcggcc tttttacggt tcctggcctt ttgctggcct tttgctcaca   4140

tgttctttcc tgcgttatcc cctgattctg tggataaccg tattaccgcc tttgagtgag   4200

ctgataccgc tcgccgcagc cgaacgaccg agcgcagcga gtcagtgagc gaggaagcgg   4260

aaga                                                                4264
```

<210> SEQ ID NO 34
<211> LENGTH: 199
<212> TYPE: DNA
<213> ORGANISM: Lycopersicon esculentum

<400> SEQUENCE: 34

```
cagccgcttt gatttctccg aagctttacc cgctccttta aatggaattt tagccatctt     60

aaagaataac gaaatgctta catggccaga gaaagtcaaa tttgcaattg gactcttgcc    120

agcaatgctt ggagggcaat cttatgttga agctcaagat gggataagtg ttaaggactg    180

gatgagaaag caaggtgtg                                                 199
```

<210> SEQ ID NO 35
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 35

```
cagccgcttt gatttctcc                                                  19
```

<210> SEQ ID NO 36
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 36

```
cacaccttgc tttctcatcc                                                 20
```

<210> SEQ ID NO 37
<211> LENGTH: 1809
<212> TYPE: DNA
<213> ORGANISM: Escherichia coli

<400> SEQUENCE: 37

```
atgttacgtc ctgtagaaac cccaacccgt gaaatcaaaa aactcgacgg cctgtgggca     60

ttcagtctgg atcgcgaaaa ctgtggaatt gatcagcgtt ggtgggaaag cgcgttacaa    120

gaaagccggg caattgctgt gccaggcagt tttaacgatc agttcgccga tgcagatatt    180

cgtaattatg cgggcaacgt ctggtatcag cgcgaagtct ttataccgaa aggttgggca    240

ggccagcgta tcgtgctgcg tttcgatgcg gtcactcatt acggcaaagt gtgggtcaat    300

aatcaggaag tgatggagca tcagggcggc tatacgccat ttgaagccga tgtcacgccg    360

tatgttattg ccgggaaaag tgtacgtatc accgtttgtg tgaacaacga actgaactgg    420

cagactatcc cgccgggaat ggtgattacc gacgaaaacg gcaagaaaaa gcagtcttac    480

ttccatgatt tctttaacta tgccgggatc catcgcagcg taatgctcta caccacgccg    540
```

aacacctggg tggacgatat caccgtggtg acgcatgtcg cgcaagactg taaccacgcg 600
tctgttgact ggcaggtggt ggccaatggt gatgtcagcg ttgaactgcg tgatgcggat 660
caacaggtgg ttgcaactgg acaaggcact agcgggactt tgcaagtggt gaatccgcac 720
ctctggcaac cgggtgaagg ttatctctat gaactgtgcg tcacagccaa aagccagaca 780
gagtgtgata tctacccgct tcgcgtcggc atccggtcag tggcagtgaa gggcgaacag 840
ttcctgatta accacaaacc gttctacttt actggctttg gtcgtcatga agatgcggac 900
ttacgtggca aaggattcga taacgtgctg atggtgcacg accacgcatt aatggactgg 960
attggggcca actcctaccg tacctcgcat tacccttacg ctgaagagat gctcgactgg 1020
gcagatgaac atggcatcgt ggtgattgat gaaactgctg ctgtcggctt taacctctct 1080
ttaggcattg gtttcgaagc gggcaacaag ccgaaagaac tgtacagcga agaggcagtc 1140
aacggggaaa ctcagcaagc gcacttacag gcgattaaag agctgatagc gcgtgacaaa 1200
aaccacccaa gcgtggtgat gtggagtatt gccaacgaac cggatacccg tccgcaagtg 1260
cacgggaata tttcgccact ggcggaagca acgcgtaaac tcgacccgac gcgtccgatc 1320
acctgcgtca atgtaatgtt ctgcgacgct cacaccgata ccatcagcga tctctttgat 1380
gtgctgtgcc tgaaccgtta ttacggatgg tatgtccaaa gcggcgattt ggaaacggca 1440
gagaaggtac tggaaaaaga acttctggcc tggcaggaga aactgcatca gccgattatc 1500
atcaccgaat acggcgtgga tacgttagcc gggctgcact caatgtacac cgacatgtgg 1560
agtgaagagt atcagtgtgc atggctggat atgtatcacc gcgtctttga tcgcgtcagc 1620
gccgtcgtcg gtgaacaggt atggaatttc gccgattttg cgacctcgca aggcatattg 1680
cgcgttggcg gtaacaagaa agggatcttc actcgcgacc gcaaaccgaa gtcggcggct 1740
tttctgctgc aaaaacgctg gactggcatg aacttcggtg aaaaaccgca gcagggaggc 1800
aaacaatga 1809

<210> SEQ ID NO 38
<211> LENGTH: 797
<212> TYPE: DNA
<213> ORGANISM: Artificial sequence
<220> FEATURE:
<223> OTHER INFORMATION: GFP synthetic construct

<400> SEQUENCE: 38
ggatccaagg agatataaca atgaagacta atctttttct ctttctcatc ttttcacttc 60
tcctatcatt atcctcggcc gaattcagta aaggagaaga acttttcact ggagttgtcc 120
caattcttgt tgaattagat ggtgatgtta atgggcacaa attttctgtc agtggagagg 180
gtgaaggtga tgcaacatac ggaaaactta cccttaaatt tatttgcact actggaaaac 240
tacctgttcc atggccaaca cttgtcacta ctttctctta tggtgttcaa tgcttttcaa 300
gatacccaga tcatatgaag cggcacgact tcttcaagag cgccatgcct gagggatacg 360
tgcaggagag gaccatcttc ttcaaggacg acgggaacta caagacacgt gctgaagtca 420
agtttgaggg agacaccctc gtcaacagga tcgagcttaa gggaatcgat ttcaaggagg 480
acggaaacat cctcggccac aagttggaat acaactacaa ctcccacaac gtatacatca 540
tggccgacaa gcaaaagaac ggcatcaaag ccaacttcaa gacccgccac aacatcgaag 600
acggcggcgt gcaactcgct gatcattatc aacaaaatac tccaattggc gatggccctg 660
tccttttacc agacaaccat tacctgtcca cacaatctgc cctttcgaaa gatcccaacg 720
aaaagagaga ccacatggtc cttcttgagt ttgtaacagc tgctgggatt acacatggca 780
tggatgaact atacaaa 797

<210> SEQ ID NO 39
<211> LENGTH: 4675
<212> TYPE: DNA
<213> ORGANISM: Artificial sequence
<220> FEATURE:
<223> OTHER INFORMATION: IR-PDSinvert-pD
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (734)..(734)
<223> OTHER INFORMATION: n is a, c, g, or t

<400> SEQUENCE: 39
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagctcta 240
atacgactca ctatagggaa agctcggtac cacgcatgct gcagacgcgt tacgtatcgg 300
atccagaatt cgtgatatct gaattcatac ctggacacct aatggctatt tggtaatttc 360
ataaatgttc attgcaattc aaaattcaaa attcaaaaat caaatcttta aagcggccat 420
ccgtataata ttaccggatg gccgcgcctt ttgtttttat gtggtcccca cgagggttac 480
acagacgtca ctgtcaacca atcaaattgc attctcaaac gttagataag tgttcatttg 540
tctttatata cttggtcccc aagtttttg tcttgcaata tgtgggaccc acttcttaat 600
gaatttcctg aatctgttca cggatttcgt tgtatgttag ctattaaata tttgcagtcc 660
gttgaggaaa cttacgagcc caatacattg ggccacgatt taattangga tcttatatct 720
gttgtaaggg cccngtgacg tcgacaagct tctcgagcct aggctagctc tagatcagcc 780
gctttgattt ctccgaagct ttacccgctc ctttaaatgg aattttagcc atcttaaaga 840
ataacgaaat gcttacatgg ccagagaaag tcaaatttgc aattggactc ttgccagcaa 900
tgcttggagg gcaatcttat gttgaagctc aagatgggat aagtgttaag gactggatga 960
gaaagcaagg tgtgggatcc cacaccttgc tttctcatcc agtccttaac acttatccca 1020
tcttgagctt caacataaga ttgccctcca agcattgctg gcaagagtcc aattgcaaat 1080
ttgactttct ctggccatgt aagcatttcg ttattcttta agatggctaa aattccattt 1140
aaaggagcgg gtaaagcttc ggagaaatca aagcggctga tctagaccac cgtgtggggg 1200
cccgagctcg cggccgctgt attctatagt gtcacctaaa tggccgcaca attcactggc 1260
cgtcgtttta caacgtcgtg actgggaaaa ccctggcgtt acccaactta atcgccttgc 1320
agcacatccc cctttcgcca gctggcgtaa tagcgaagag gcccgcaccg atcgcccttc 1380
ccaacagttg cgcagcctga atggcgaatg gaaattgtaa gcgttaatat tttgttaaaa 1440
ttcgcgttaa atttttgtta aatcagctca ttttttaacc aataggccga aatcggcaaa 1500
atcccttata aatcaaaaga atagaccgag atagggttga gtgttgttcc agtttggaac 1560
aagagtccac tattaaagaa cgtggactcc aacgtcaaag ggcgaaaaac cgtctatcag 1620
ggcgatggcc cactacgtga accatcaccc taatcaagtt ttttggggtc gaggtgccgt 1680
aaagcactaa atcggaaccc taaagggagc ccccgattta gagcttgacg gggaaagccg 1740

-continued

```
gcgaacgtgg cgagaaagga agggaagaaa gcgaaaggag cgggcgctag ggcgctggca   1800
agtgtagcgg tcacgctgcg cgtaaccacc acacccgccg cgcttaatgc gccgctacag   1860
ggcgcgtcag gtggcacttt tcggggaaat gtgcgcggaa cccctatttg tttatttttc   1920
taaatacatt caaatatgta tccgctcatg agacaataac cctgataaat gcttcaataa   1980
tattgaaaaa ggaagagtat gagtattcaa catttccgtg tcgcccttat tccctttttt   2040
gcggcatttt gccttcctgt ttttgctcac ccagaaacgc tggtgaaagt aaaagatgct   2100
gaagatcagt tgggtgcacg agtgggttac atcgaactgg atctcaacag cggtaagatc   2160
cttgagagtt ttcgccccga agaacgtttt ccaatgatga gcacttttaa agttctgcta   2220
tgtggcgcgg tattatcccg tattgacgcc gggcaagagc aactcggtcg ccgcatacac   2280
tattctcaga atgacttggt tgagtactca ccagtcacag aaaagcatct tacggatggc   2340
atgacagtaa gagaattatg cagtgctgcc ataaccatga gtgataacac tgcggccaac   2400
ttacttctga caacgatcgg aggaccgaag gagctaaccg cttttttgca caacatgggg   2460
gatcatgtaa ctcgccttga tcgttgggaa ccggagctga atgaagccat accaaacgac   2520
gagcgtgaca ccacgatgcc tgtagcaatg gcaacaacgt tgcgcaaact attaactggc   2580
gaactactta ctctagcttc ccggcaacaa ttaatagact ggatggaggc ggataaagtt   2640
gcaggaccac ttctgcgctc ggcccttccg gctggctggt ttattgctga taaatctgga   2700
gccggtgagc gtgggtctcg cggtatcatt gcagcactgg ggccagatgg taagccctcc   2760
cgtatcgtag ttatctacac gacggggagt caggcaacta tggatgaacg aaatagacag   2820
atcgctgaga taggtgcctc actgattaag cattggtaac tgtcagacca agtttactca   2880
tatatacttt agattgattt aaaacttcat ttttaattta aaaggatcta ggtgaagatc   2940
ctttttgata atctcatgaa caataaaact gtctgcttac ataaacagta atacaagggg   3000
tgttatgagc catattcaac gggaaacgtc ttgctctagg ccgcgattaa attccaacat   3060
ggatgctgat ttatatgggt ataaatgggc tcgcgataat gtcgggcaat caggtgcgac   3120
aatctatcga ttgtatggga agcccgatgc gccagagttg tttctgaaac atggcaaagg   3180
tagcgttgcc aatgatgtta cagatgagat ggtcagacta aactggctga cggaatttat   3240
gcctcttccg accatcaagc attttatccg tactcctgat gatgcatggt tactcaccac   3300
tgcgatcccc gggaaaacag cattccaggt attagaagaa tatcctgatt caggtgaaaa   3360
tattgttgat gcgctggcag tgttcctgcg ccggttgcat tcgattcctg tttgtaattg   3420
tccttttaac agcgatcgcg tatttcgtct cgctcaggcg caatcacgaa tgaataacgg   3480
tttggttgat gcgagtgatt ttgatgacga gcgtaatggc tggcctgttg aacaagtctg   3540
gaaagaaatg cataaacttt tgccattctc accggattca gtcgtcactc atggtgattt   3600
ctcacttgat aaccttattt ttgacgaggg gaaattaata ggttgtattg atgttggacg   3660
agtcggaatc gcagaccgat accaggatct tgccatccta tggaactgcc tcggtgagtt   3720
ttctccttca ttacagaaac ggctttttca aaaatatggt attgataatc ctgatatgaa   3780
taaattgcag tttcatttga tgctcgatga gtttttctaa gaattaattc atgaccaaaa   3840
tcccttaacg tgagttttcg ttccactgag cgtcagaccc cgtagaaaag atcaaaggat   3900
cttcttgaga tccttttttt ctgcgcgtaa tctgctgctt gcaaacaaaa aaaccaccgc   3960
taccagcggt ggtttgtttg ccggatcaag agctaccaac tctttttccg aaggtaactg   4020
gcttcagcag agcgcagata ccaaatactg tccttctagt gtagccgtag ttaggccacc   4080
```

-continued acttcaagaa ctctgtagca ccgcctacat acctcgctct gctaatcctg ttaccagtgg 4140
ctgctgccag tggcgataag tcgtgtctta ccgggttgga ctcaagacga tagttaccgg 4200
ataaggcgca gcggtcgggc tgaacggggg gttcgtgcac acagcccagc ttggagcgaa 4260
cgacctacac cgaactgaga tacctacagc gtgagctatg agaaagcgcc acgcttcccg 4320
aagggagaaa ggcggacagg tatccggtaa gcggcagggt cggaacagga gagcgcacga 4380
gggagcttcc agggggaaac gcctggtatc tttatagtcc tgtcgggttt cgccacctct 4440
gacttgagcg tcgatttttg tgatgctcgt caggggggcg gagcctatgg aaaaacgcca 4500
gcaacgcggc ctttttacgg ttcctggcct tttgctggcc ttttgctcac atgttctttc 4560
ctgcgttatc ccctgattct gtggataacc gtattaccgc ctttgagtga gctgataccg 4620
ctcgccgcag ccgaacgacc gagcgcagcg agtcagtgag cgaggaagcg gaaga 4675

<210> SEQ ID NO 40
<211> LENGTH: 379
<212> TYPE: DNA
<213> ORGANISM: Artificial sequence
<220> FEATURE:
<223> OTHER INFORMATION: TYLCV-CP hybridization probe

<400> SEQUENCE: 40
gaaggctgaa cttcgacggc ccatacaggc ccatgtaccg aaagcccaga aatacagaat 60
gtatcgaagc cctgatgttc cccgtggatg tgaaggcccc tttaaagtcc agtcttatga 120
gcaacgggat gatattaagc atcctggtat tgttcggttg tgttagtgat gttactcgtg 180
gatctggaat tactcacaga gtgggtaaga ggttctgtgt taaatcgata tattttttag 240
gtaaagtctg gatggatgaa aatatcaaga agcagaatca cactaatcag gtcatgttct 300
tcttggtccg tgatagaagg ccctatggaa acagcccaat ggattttgga caggttttta 360
atatgttcga taatgagcc 379

<210> SEQ ID NO 41
<211> LENGTH: 573
<212> TYPE: DNA
<213> ORGANISM: Artificial sequence
<220> FEATURE:
<223> OTHER INFORMATION: GUS hybridization probe

<400> SEQUENCE: 41
cgccgggaat ggtgattacc gacgaaaacg gcaagaaaaa gcagtcttac ttccatgatt 60
tctttaacta tgccgggatc catcgcagcg taatgctcta caccacgccg aacacctggg 120
tggacgatat caccgtggtg acgcatgtcg cgcaagactg taaccacgcg tctgttgact 180
ggcaggtggt ggccaatggt gatgtcagcg ttgaactgcg tgatgcggat caacaggtgg 240
ttgcaactgg acaaggcact agcgggactt tgcaagtggt gaatccgcac ctctggcaac 300
cgggtgaagg ttatctctat gaactgtgcg tcacagccaa aagccagaca gagtgtgata 360
tctacccgct tcgcgtcggc atccggtcag tggcagtgaa gggcgaacag ttcctgatta 420
accacaaacc gttctacttt actggctttg gtcgtcatga agatgcggac ttacgtggca 480
aaggattcga taacgtgctg atggtgcacg accacgcatt aatggactgg attggggcca 540
actcctaccg tacctcgcat tacccttacg ctg 573

<210> SEQ ID NO 42
<211> LENGTH: 20
<212> TYPE: DNA
<213> ORGANISM: Artificial sequence

```
<220> FEATURE:
<223> OTHER INFORMATION: Single strand DNA oligonucleotide

<400> SEQUENCE: 42

aggaattgac ggaagggcac                                                20


<210> SEQ ID NO 43
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 43

gtgcggccca gaacatctaa g                                              21


<210> SEQ ID NO 44
<211> LENGTH: 24
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 5' phosphorylated oligonucleotide

<400> SEQUENCE: 44

ggtctgacgc tcagtggaac gaaa                                           24


<210> SEQ ID NO 45
<211> LENGTH: 26
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 5' phosphorylated oligonucleotide

<400> SEQUENCE: 45

gtgagctgat accgctcgcc gcagcc                                         26


<210> SEQ ID NO 46
<211> LENGTH: 10
<212> TYPE: PRT
<213> ORGANISM: Artificial sequence
<220> FEATURE:
<223> OTHER INFORMATION: A viral zinc finger motif

<400> SEQUENCE: 46

Gly Cys Glu Gly Pro Cys Lys Val Gln Ser
1               5                   10


<210> SEQ ID NO 47
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 47

gcgaacgaac acgatagcaa                                                20


<210> SEQ ID NO 48
<211> LENGTH: 19
<212> TYPE: DNA
<213> ORGANISM: Artificial sequence
```

<220> FEATURE:
<223> OTHER INFORMATION: Single strand DNA oligonucleotide

<400> SEQUENCE: 48

```
cgtcaatgag ggcgtgaat                                                  19
```

<210> SEQ ID NO 49
<211> LENGTH: 5742
<212> TYPE: DNA
<213> ORGANISM: Pseudomonas fluorescens

<400> SEQUENCE: 49

```
atgaacaagc caatcaagaa tatcgtcatc gtgggcggcg gcaccgcggg ctggatggcc      60
gcttcgtacc tcgtccgggc gctccaacag caggtaaaca tcacgctcat cgagtctgcg     120
gcgatccccc ggatcggcgt gggcgaggcg accatcccga gtttgcagaa ggtgttcttc     180
gacttcctcg ggataccgga gcgggagtgg atgccccaag tgaacggcgc cttcaaggcc     240
gcgatcaagt tcgtgaactg gagaaaatct cccgacccat cgcgcgaaga ttacttctac     300
catttgttcg gcagcgtgcc gaactgcgac ggcgtgccgc ttacccacta ctggctgcgc     360
aagcgcgaac agggcttcca gcagccgatg gcgtacgcgt gctatccgca gcccggggcc     420
ctcgacggca agctggcacc ctgcctggcc gacggcaccc gccagatgtc ccacgcgtgg     480
cacttcgacg cgcacctggt ggccgacttc ttgaagcgct gggccgtcga gcgcggggtg     540
aatcgcgtgg tcgacgaggt cgtggaggtt caactgaacg accgcggcta catctccacc     600
ctgttaacca aggaagggcg gacgctggag gcggacctgt tcatcgactg ctccggcatg     660
cgagggctcc tgatcaatca ggccctgaag gaacccttca tcgacatgtc cgactacctg     720
ctgtgcgaca gcgcggtcgc cagcgccgtg cccaacgacg acgcgcgcga gggggtcgag     780
ccttacacct ccgcgattgc catgaactcg ggatggacct ggaagattcc gatgctgggc     840
cggttcggca gcggctacgt cttctcgagc aagttcacct cgcgcgacca ggccaccgcc     900
gacttcctca aactctgggg cctctcggac aatcagcagc tcaaccagat caagttccgg     960
gtcgggcgca acaagcgggc gtgggtcaac aactgcgtct cgatcgggct gtcgtcgtgc    1020
tttctggagc ccctggaatc gacgggaatc tacttcatct acgcggcgct ttaccaactc    1080
gtgaagcact tccccgacac ctcgttcgac ccgcggttgc gcgacgcatt caacgccgag    1140
atcgtctaca tgttcgacga ctgccgagac ttcgtccagg cgcactattt cactacgtcg    1200
cgcgaagaca cgccgttctg gctcgcgaac cggcacgaac tgcggctctc ggacgccatc    1260
caggagaagg ttgagcgcta caaggccggg ctgccactga ccaccacctc gttcgacgat    1320
tccacgtact acgagacctt cgactacgaa ttcaagaact tctggttgaa cggcaactac    1380
tactgcatct ttgccggcct gggcatgctg cccgaccggt cgctgccgct cctgcagcac    1440
cgaccggagt cgatccagaa ggccgaagcg atgttcgcca gcatccggcg cgaagccgag    1500
cgcctgcgca cgagcctgcc gacgaactac gactacctgc ggtcactgcg tgacggcgcg    1560
cagctgtcgc gcaaccagca cgggccgacg ctcgcggctc aggaacgcca gtagtggaac    1620
gcaccttgaa ccgggtatcc gcattcgcgg ccacacacgc tgccgtggcg gcctgcgatc    1680
cgctacaggc acgcgcgctg gttctgcagc tgccggccct gaaccgtgac aaggacgtgc    1740
ccggcatcgt cggcctgctg cgcgatttcc tcccggtgag cggcgtgccc tccagctggg    1800
gcttcgtcga agccgccgcc gcgatgcggg acatcggttt cttcctgggg tcgctcaagc    1860
ggcacggaca tgagcccgtg gacctggtgc ccgggcttga acgggtgctg ctcgacctgg    1920
```

-continued

```
cacgggtgac cgacttgccg ccgcgcgaga cactcctgca tgtgacggtc tggaacccgg   1980
cggcggccga tgcgcagcgg agctacaccg ggctgcccga cgaagcgcac ctgctcgaga   2040
gcgtgcgcat ctcgatggcg gccctcgagg cggccatcgc gttgaccgtc gagctgtccg   2100
atgtatccct gcgctcgccc gcgttcgcgc aagggtgcga tgagctggaa gcctacctgc   2160
agaaaatggt cgaatcgatc gtctacgcgt accgcttcat ctcgccccag gtcttctacg   2220
atgagctgcg cccc ttctac gaaccgattc gagtcgggg ccagagctac ctcggccccg   2280
gcgccgtaga aatgcccctc ttcgtgctgg agcacgtcct gtggggctcg caatcggacg   2340
acccagctta tcgagaattc aaagagacat acctgcccta cgtgcttccc gcgtacaggg   2400
cggtctacgc tcggttcgcc acaaagccgg cgctcatcga ccgtgcgctc gacgaggcgc   2460
gagcggtggg tacgcagggc gagcacgtcc gggctgggct gacggccctc gagcgggtct   2520
tcaaggtcct gctgcgcttc cgggcgcctc acctcaaatt ggcggagcgg gcatacgaag   2580
ccgggcgcag cggccccaca accggcagcg gggctacgc gcccagcatg ctcggcgatc   2640
tactcacgct cacctgtgcc gcgcggtccc gcatccgtgc cgcgctcgat gaatcctgat   2700
gcgcgcgacc cagtgttatc tcacaaggag agtttgcccc catgactcag aagagccccg   2760
cgaacggaca cgatagcaac cacttcgacg taatcatcct cggttcgggc atgtccggta   2820
cccagatggg ggccatcctg gccaaacaac agtttcgcgt gctgatcatc gagcagtcgt   2880
cgcacccgcg gttcacgatc ggcgaatcgt cgatccccga aacgtctctc atgaaccgca   2940
tcatcgctga tcgctacgac attccggagc tcggccacat cacctcgttc tactcgacgc   3000
agcgttacgt ttcgtcgagc acgggcatca agcgcaactt cggcttcgtg ttccacaaac   3060
ctggccagga gcacgacccg aaggagttca cccagtgcgt cattcccgag ctgccgtggg   3120
ggccggagag ccattattac cggcaggacg tcgacgccta tctgttgcaa gcggccatca   3180
aatatggctg cacggtccgc cagaagacga gcgtgaccga atatcacgcg gacaaggacg   3240
gcgtcgcggt gaccaccgcc gagggcgagc ggttcaccgg ccggtacatg atcgactgcg   3300
gaggacccgg cgcgccgctg gcgaccaagt tcgggctccg cgaagagccg tgtcgcttca   3360
agacgcactc gcgcagcctc tacacgcaca tgctcggggt caagccgttc gacgacatct   3420
tcaaggtcaa ggggcagcgc tggcgctggc acgaaggaac cctgcaccac atgttcaccg   3480
gcggctggct ctgggtgatt ccgttcaaca accacccgcg ctcgaccaat aacctggtga   3540
gcgtcggcct gcagctcgac ccgcgtgtct acccgaaaac cgacattccc gcgcagcagg   3600
aattcgacga gttcctcgcg cggttcccga gcatcggcgc tcagttccgg gacgccgtgc   3660
cagtgcgcga ctgggtcaag accgaccgcc tgcagttctc gtcgaacgcc tgcgtcggcg   3720
accgctactg cctgatgctg cacgcgaacg ggttcatcga cccgctcttc tcccgggggc   3780
tcgagaacac cgcggtgacc atccacgcgc tcgcggcgcg cctcatcaag gcgctacgcg   3840
acgacgactt ctcccccgag cgcttcgagt acatcgagcg cctgcagcaa aagcttttgg   3900
accacaacga cgacttcgtc agctgctgct acacggcgtt ctcggacttc cgcctatggg   3960
acgcgttcca ccggctgtgg gcggtcggca ctatcctcgg gcagttccgg ctggtgcaag   4020
cccacgcgag gtttcgcgcg tcgcgcgacg agggcgacct cgatcacctc gacaacgacc   4080
cgccgtacct cgggtacctg tgcgcggaca tggagcagta ctaccagttg ttcaacgacg   4140
ccaaagccga ggtcgaggct gtgagcgccg ggcacaagtc ggccgaggag gccgcgttgc   4200
ggattcacgc cctcatcgac gaacgagact tcgccaagcc gatgttcggc ttcgggtact   4260
gcatcaccgg ggacaagccg cagctcaaca actcgaagta cagcctgata ccggcgatga   4320
```

-continued agctgatgta ctggacgcaa acccgcgcgc cggcagaggt gaagaagtac ttcgactaca 4380
acccgatgtt cgcgctgctc aaggcgtaca tcaccacccg catcggcttg gctctgaaga 4440
agtagtcggc caaggacggc acacacgcga tgaacaacat tcaattggat caagcgaacg 4500
tcaagaagca tcccccgggg gcgtacgacg cgaccacacg cgtggccgcg agctggtacg 4560
tcgcgatgcg ctcgaacggc ctcagggaca agccgaagga gttgacgctc tttggccgtc 4620
cgtacgtggc gtggcgcgca gcgacggggc aggccgtggt gatggaccgc cactgctcgc 4680
acctgggcgc gaacctggct gacgggcgga tcaaggacgg gtgcatccag tgcccgtttc 4740
accactggcg ctacgacgag caaggcaagt gcgttcacat ccccggccac agcgaggtgg 4800
tgcgccagct ggagccggtg ccacgcgcgg cgcgccagcc gacgttggtc accaccgagc 4860
gatacggcta cgtgtgggtc tggtacggct ccccgcagcc gctgcacccg ctgcccgaaa 4920
tcaccgcagc cgacgtcgac aacggcgact tcatgcacct gcacttcgcg ttcgagacga 4980
cgacggcggt cttgcggatc gtcgagaact tctacgacgc acagcacgca acccccgtgc 5040
acgcgctccc gatctcggcc ttcgaactca agctcttcga cgactggagc cggtggccgg 5100
aggttgagtc gctggcccgg gcgggcgcgt ggttcggtgc cgggatcgac ttccacgtga 5160
accgctactt cggccccctc ggcatgctgt cgcgcgcgct cggcctgaac atgtcgcaga 5220
tgaacctgca cttcgatggc taccccggcg ggtgcgtcat gaccgttgcc ctggacgcag 5280
acgtcaaata caaactgctc cagtgtgtga caccggtgag cgacggcaag aacatcatgc 5340
acatgctcat ctcgatcaag aaggtgggcg gcgtcctgcg ccgtgcgacc gacttcgtgc 5400
tgttcgggct gcagaccaga caggcagcgg ggtacgacgt caaaatctgg aacgggatga 5460
agcccgacgg cggcggcgct tacagcaagt acgacaagct cgtgctcaag taccgtgcgt 5520
tctaccgcgg ctgggtcgac cgtgtcgcga gtgagcagta atgcgtgagg ccgagccggt 5580
agcggtcgcg tcgcgctgcc cggcgcttgc gaacctttcg agctgcgtca cggagatcac 5640
ggcgtacggc gcggcgggcc cgcttgggct cgcggccacc cgcttggtgt cggtgtcgct 5700
ctttgcgagg tattgatgac catctggctg ttgcaactcg tg 5742

<210> SEQ ID NO 50
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 50
gcgaacgaac acgatagcaa 20

<210> SEQ ID NO 51
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 51
cgtcaatgag ggcgtgaat 19

<210> SEQ ID NO 52
<211> LENGTH: 10
<212> TYPE: PRT
<213> ORGANISM: Tomato yellow leaf curl virus
<220> FEATURE:

-continued

```
<221> NAME/KEY: misc_feature
<223> OTHER INFORMATION: Partial sequence of the TYLCV coat protein

<400> SEQUENCE: 52

Gly Cys Glu Gly Pro Cys Lys Val Gln Ser
1               5                   10
```

PLANT EXPRESSION CONSTRUCTS AND METHODS OF UTILIZING SAME

RELATED APPLICATIONS

This application is a National Phase Application of PCT Application No. PCT/IL2007/000688 having International Filing Date of Jun. 7, 2007, which claims the benefit of US Provisional Patent Application No. 60/811,406, filed on Jun. 7, 2006, and US Provisional Patent Application No. 60/876,999, filed on Dec. 26, 2006. The contents of the above Applications are all incorporated herein by reference.

FIELD AND BACKGROUND OF THE INVENTION

The present invention relates to Gemini-virus based constructs capable of symptom less, systemic spread in plant host.

Genetic engineering is slowly replacing classical genetic techniques in generation of plants which are resistant to disease, drought, pests or are simply commercially improved.

Genes that provide resistance against biotic as well as abiotic stresses have been successfully introduced into crop plants [see for example, saline soil resistant tomatoes in Zhang, H-X. and Blumwald, E. Nature Biotechnology 19(8): 765-768. (2001); potato virus X (PVX) resistant potatoes expressing the viral coat protein in U.S. Pat. No. 5,773,701; fungal resistance in U.S. Pat. No. 6,288,303; insect resistance in plants expressing the *Bacillus thuringiensis* toxin in Moellenbeck, D. J., et al., Nature Biotechnology 19:668-672 (2001); herbicide resistance in corn in U.S. Pat. No. 7,002,064 7002056 and cabbage]. In another example, the nutritional quality of an important crop such as rice was improved by introducing transgenes that enabled plants to manufacture beta-carotene (a vitamin A precursor) in their endosperm, thus solving vitamin A deficiency in rice eating populations [Ye, X., Science 287:303-305 (2000)]. Indeed, more than 50 genetically modified plants have already been approved by the FDA [Bren, L., FDA Consumer Magazine online issue 37 (2003)].

The latest trend in genetic engineering of crop plants is pharma-crops that produce proteins or chemicals for pharmaceutical and industrial uses. Plants have many advantages as a productive economical source of biomass. Plants lack contamination with animal pathogens, their genetic manipulation is relatively easy, they possess eukaryotic protein modification machinery and therefore are a better industrial protein source than prokaryote or cell line systems. Plants have been used, for example, for the production of human serum albumin [Sijmons, P C, et al., Biotechnology (NY) 8(3):217-21 (1990)], of protein antigens to be used as vaccines [Haq, T A et al., Science.; 268(5211):714-6 (1995)] and for the production of humanized antibodies [Tavladoraki, P., et al., Nature 366, 469-472 (1993)].

Present techniques for DNA delivery into plants include direct as well as indirect methods. However, each of these delivery methods is not without limitations. The direct DNA delivery systems [particle bombardment: Klein, T M et al., Nature, 327, 70-73 (1987); silicon carbide whisker technology (SIC-Kaepplar, H. F., et al., Plant Cell Reports 8: 415-418 (1990); electroporation (D'Halluin et al., 1992)] tend to result in integration of multiple copies of transgenes and are considered to be limited, unpredictable and transient. Indirect approaches [e.g. *Agrobacterium*: Travella S, Plant Cell Rep. 23(12): 780-9 (2005)] oftentimes result in integration of multiple copies of the foreign DNA into the plant genome along with unwanted sequences from the vector 'backbone' [Lange M, et al., Plant Cell Rep. (2006)].

Integration of foreign DNA into the plant genome to become a heritable trait raises many risks. Traits beneficial to crops may, through horizontal gene transfer or hybridization through breeding with wild relatives, provide wild plants with unwanted competitive advantages [(Ellstrand, N. C., et al., Annual Review of Ecology and Systematics 30: 539-63 (1999)]. Also, Transformation with *Agrobacterium* is a complex process which requires elimination of false positives arising from the growth of *Agrobacterium* in host tissues, and selection of transformed plants. The use of antibiotic resistance as a marker in the development of transgenic crops has also raised concerns regarding the increase of antibiotic resistance in the environment through horizontal transfer of antibiotic resistance genes to soil micro-organisms. Scientists now have the means to remove marker genes before a crop plant is developed for commercial use [e.g., Iamtham, S., and A. Day, Nature Biotechnology 18:1172-1176 (2000)], but these means involve further costs and tedious procedures. In addition, several species or varieties of plants are still difficult to transform.

Infection of plants with modified viruses is simpler and quicker than the regeneration of stably transformed plants, since plant viruses are small and easy to manipulate, have the inherent ability to enter the plant cell, and will multiply to produce a high copy number of the gene of interest. Viral vectors have been engineered for delivery of genetic material and expression of recombinant proteins in plants [e.g., Pogue, G. P., Annu. Rev. Phytopathol. 40: 45-74 (2002); Gleba, Y., et al., Curr. Opin. Plant Biol. 7: 182-188 (2004); U.S. Pat. Nos. 5,316,931 and 5,811,653 for RNA virus vectors]. Viral expression systems are considered transient expression systems since the viral vectors are not integrated into the genome of the host. However, viral vectors still hold many limitations. Plant viral vectors have the potential to cause disease in their plant hosts, they posses the ability to naturally spread between plants in the field, and in some cases, can be spread through pollen or seed to the next generation. Viral vectors are also limited in their systemic spread in the plant, in host ranges, expression stability, and in the size of insert which can be tolerated [Shepherd, R. J., The Biochemistry of Plants. Ed. A. Marcus, 15, 536-616. Academic Press, New York (1989); Dawson, W. O. et al., Virology 172:285-292 (1989); Covey, S. N. & Hull, R. in Genetic Engineering with Plant Viruses, pp. 217-249, CRC Press (1992); Viaplana et al., 82, 59-65 Journal of General Virology (2001)]. Finally, like transgenic plants, modified viruses are classified as a Genetically Modified Organism (GMO) and thus are subject to regulatory and moral constraints.

Geminiviruses are viruses that possess either one or two single-stranded DNA molecules, encapsidated in twinned "geminate" icosahedral particles. The Geminivirus replicative cycle relies entirely on DNA intermediates and occurs within the nucleus of the infected cell through two basic stages: conversion of ssDNA to dsDNA intermediates and rolling-circle replication, leading to the production of, progeny virus. In Geminiviruses, expression of viral proteins occurs from the transcriptionally active circular dsDNA forms [Gutierrez, C., et al., Veterinary Microbiology 98: 111-119 (2004)].

An example of a Geminivirus is TYLCV, which is a monopartite begomovirus [Stanely, J. et al., Advances in virus research 30, 139-177, (1985)] with a known genome organization [Hanley-Bowdoin, L., et al., Critical Reviews in Biochemistry and Molecular Biology 35, 105-140 (2000)]. TYLCV infection of tomato presents a serious agricultural-economical problem. TYLCV can not be mechanically inoculated and is transmitted by *Bemisia tabaci*, but agroinoculation of Geminivirus DNA as an entity longer-than-one-genome-length causes systemic infection [Czosnek, H., et al., Plant Mol. Biol. 22, 995-1005 (1993)].

Until recently insertions into the DNA genome of Geminiviruses for gene expression was successful only if the modified vector is of a size comparable to that of the wild type viral DNA. In monopartite geminiviruses, removal of any viral gene in order to maintain such a size abolished the viral vector's ability to spread systemically [Stanley, J., Curr. Opin. Genet. Dev. 3, 91-96 (1993)]. Introduction of bacterial compatible origin of replication and a multiple cloning site enabled plant expression from a Gemini vector, but the insertion abolished systemic spread, and thus the use of such monopartite Gemini-based expression vectors was confined to cell cultures and endosperm [Ugaki, M. et al., Nucleic Acids Research 19, 371-377 (1991); Tamilselvi. D., et al., Plant Cell Reports 23, 81-90 (2004)], where systemic infection was not required.

Pyrrolnitrin (PRN) is an antifungal and antibacterial compound produced by certain strains of the bacteria *Pseudomonas fluorescence* and other bacteria such as *Burkholderia cepacia* (for example, Chernin et al. (1996) *Current Microbiology* 32:208-212 and El-Banna and Winkelmann (1998) *J. Applied Microbiology* 85:69-78). The metabolic pathway of PRN production and the functional dissection of its component have been elucidated (for example, Kirner et al. (1998) *J. Bacteriol.* 180:1939-1943). PRN-producing microorganisms are potential agents for biological control of plants diseases by colonizing the soil with PRN-producing bacteria (for example, Hwang et al. (2002) *Biological Control* 25:56-63 and Haas and Keel (2003) *Annual review of Phytopatology* 41:117-153). PRN spraying in field tests reduced disease incidence caused reduction in infectivity of several fungi up to 8-fold. In addition, bacterial genes involved in the PRN pathway were introduced into plants (each was introduced separately), and the resultant transgenic plants carrying 3 transgenes (out of the 4 genes in the operon) were field-tested, reducing disease incident caused by several fungi 3-5-fold. Data on field tests (spraying and transgenic) are documented in U.S. Pat. No. 5,698,425).

There is thus a widely recognized need for, and it would be highly advantageous to have, a transient expression vector devoid of the above limitations.

SUMMARY OF THE INVENTION

According to one aspect of the present invention there is provided a Geminivirus based expression construct comprising a heterologous polynucleotide sequence being flanked by a non-contiguous nucleic acid sequence encoding a Geminivirus replicase or replicase associated protein.

According to further features in preferred embodiments of the invention described below, the heterologous polynucleotide is larger than 1 kb.

Optionally, the heterologous polynucleotide is larger than 5 kb.

Optionally, the heterologous polynucleotide comprises an operon.

Optionally, the heterologous polynucleotide is adapted for gene silencing.

Optionally, the expression construct includes a bacterial polynucleotide sequence.

Optionally, the expression construct includes a polynucleotide sequence encoding a modified Geminivirus coat protein (CP).

Optionally, the expression construct includes a dysfunctional bacterial origin of replication According to still further features in the described preferred embodiments the expression construct further comprises a bacterial polynucleotide sequence.

According to still further features in the described preferred embodiments the expression construct further comprises a polynucleotide sequence encoding a modified Geminivirus coat protein (CP).

According to still further features in the described preferred embodiments the modified Geminivirus coat protein comprises a mutation or deletion in nucleotides encoding an N-terminal 100 amino acids.

According to still further features in the described preferred embodiments the expression construct further comprises a polynucleotide sequence encoding a modified Geminivirus V2 protein.

According to still further features in the described preferred embodiments the expression construct further comprises a polynucleotide sequence encoding a modified Geminivirus C4 protein.

According to still further features in the described preferred embodiments the modified Gemini-virus C4 protein includes a mutation or deletion.

According to another aspect of the present invention there is provided a Geminivirus based expression construct being capable of systemic symptomeless spread in a plant host.

According to still further features in the described preferred embodiments the expression construct encodes at least of one molecule selected from the group consisting of a reporter molecule, an antiviral molecule, a viral moiety, an antifungal molecule, an antibacterial molecule, an insect resistance molecule, a herbicide resistance molecule, a biotic or abiotic stress tolerance molecule, a pharmaceutical molecule, a growth inducing molecule, and a growth inhibiting molecule.

According to still further features in the described preferred embodiments the construct further includes a heterologous polynucleotide larger than 1 kb.

According to still further features in the described preferred embodiments the expression construct further comprises a bacterial polynucleotide sequence. According to still further features in the described preferred embodiments the expression construct further comprises a polynucleotide sequence encoding a modified Geminivirus coat protein (CP).

According to still further features in the described preferred embodiments the modified Geminivirus CP comprises a mutation or deletion in nucleotides encoding an N-terminal 100 amino acids.

According to still further features in the described preferred embodiments the expression construct further comprising a polynucleotide sequence encoding a modified Geminivirus V2 protein.

According to still further features in the described preferred embodiments the expression construct further comprises a polynucleotide sequence encoding a modified Geminivirus C4 protein.

According to still further features in the described preferred embodiments the Geminivirus is a begomovirus.

According to still further features in the described preferred embodiments the Geminivirus is a Tomato yellow leaf curl virus (TYLCV).

According to still further features in the described preferred embodiments the expression construct is expressible in a plant host selected from the group consisting of the dicotyledonous Solanaceae, Cucurbitaceae, Umbelliferae, Rosacea, Vitacea, and Cruciferae and of the Monocotyledonous Liliacae, Gramineae (Poaceae), Musaceae.

According to still further features in the described preferred embodiments the modified Geminivirus V2 protein is further characterized by the disruption of protein recognition motifs selected from the group consisting of SH2, SH3, PDZ and SUMO.

According to still further features in the described preferred embodiments the expression construct further comprises a polynucleotide sequence encoding a modified Geminivirus replicase.

According to still further features in the described preferred embodiments the modified Geminivirus replicase is characterized by reduced capability of rolling circle, single stranded DNA replication.

According to yet another aspect of the present invention there is provided a method of expressing a molecule of interest in a plant cell comprising introducing into the plant tissue a nucleic acid construct including the molecule of interest being flanked by a non-contiguous nucleic acid sequence encoding a Geminivirus replicase.

According to still further features in the described preferred embodiments the method further comprises inoculating the plant with a Geminivirus.

According to still further features in the described preferred embodiments the nucleic acid construct further includes a polynucleotide sequence derived from a Geminivirus V2 protein.

According to still further features in the described preferred embodiments the nucleic acid construct further includes a bacterial polynucleotide sequence.

According to still further features in the described preferred embodiments the Geminivirus is a wild type Geminivirus.

According to still further features in the described preferred embodiments the Geminivirus is a modified Geminivirus.

According to still further features in the described preferred embodiments they molecule of interest is selected from the group consisting of a reporter molecule, an antiviral molecule, a viral moiety, an antifungal molecule, an antibacterial molecule, an insect resistance molecule, a herbicide resistance molecule, a biotic or abiotic stress tolerance molecule, a pharmaceutical molecule, a growth inducing molecule and a growth inhibiting molecule.

According to still further features in the described preferred embodiments the plant is selected from the group consisting of the dicotyledonous Solanaceae, Cucurbitaceae, Umbelliferae, Rosaceae, Vitacea, and Cruciferae and of the Monocotyledonous Liliacae, Gramineae (Poaceae), Musaceae.

According to yet another aspect of the present invention there is provided a method of generating a plant resistant to Geminivirus infection comprising introducing into the plant a nucleic acid construct including a polynucleotide encoding anti-viral molecule being flanked by a non-contiguous nucleic acid sequence encoding a Geminivirus replicase.

According to still further features in the described preferred embodiments expression of the anti-viral molecule is initiated by Geminivirus infection.

According to yet another aspect of the present invention there is provided a modified Geminivirus genome comprising a mutation or deletion of a polynucleotide sequence encoding a Geminivirus replicase gene and/or a coat protein gene, the mutation or deletion resulting in systemic symptomeless spread of the Geminivirus genome in plant tissue.

Optionally, the modified Geminivirus genome includes a mutation or deletion which renders the genome intransmissible by an insect vector.

According to yet another aspect of the present invention there is provided a nucleic acid construct comprising polynucleotide sequences being flanked by heterologous sequences derived from a Geminivirus intergenic region.

According to yet another aspect of the present invention there is provided a Geminivirus based vector being capable of replication in a prokaryotic cell and systemic symptomeless spread in a plant host.

Optionally, the Geminivirus based vector is incapable of plant to plant transmission by an insect vector.

The present invention successfully addresses the shortcomings of the presently known configurations by providing a universal viral based expression vector which can spread systemically in all plants and yet is symptomeless and capable of carrying expressible inserts which are substantially larger than those carried by known viral expression vectors. Another advantage of the present vector is that it does not integrate into the host genome and thus it is not inherited by progeny plants.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1*c* is an alignment of the coat protein sequence of TYLCV (upper lines-(SEQ ID NO: 5) and the coat protein sequence translated from IL-60 (SEQ ID NO: 3);

FIG. 1*d* is an alignment of the DNA sequence of IL-60 (upper lines in upper case letters; SEQ ID No.: 2) and TYLCV (lower case letters; SEQ ID No.: 4) done with GAP analysis; deleted nucleotide T and the inserted nucleotide G are highlighted in yellow;

FIGS. 5*a* to 5*e* are photomicrographs depicting expression of foreign genes carried on IL-60-BS; FIGS. 5*a-b* show expression of beta-glucuronidase (GUS) 1 month (FIG. 5*a*) and 12 months (FIG. 5*b*) post injection of plants with IL-60-BS-GUS (SEQ ID NO: 9); FIG. 5*c* shows GUS expression in the root (12 months post injection to the plant stem); FIGS. 5*d-e* are fluorescent microscope images taken with (FIG. 5*d*) or without a filter (FIG. 5*e*), showing GFP immunofluorescence in plants 3 months post injection with IL-60-BS-GFP; FIG. 5*d* is a magnified image of the vein branch point shown in FIG. 5*e*.

FIG. 6 depicts an ethidium bromide stained gel of PCR products illustrating that IL-60-BS-GUS is not heritable; IL-60-BS-GUS (SEQ ID NO: 9) was introduced into parental plants 12 months before analysis; PCR analysis using primers for a GUS sequence (SEQ ID NO: 25 and NO: 26) show that GUS was not amplified in the progeny (F1) tomato plants although the parent plant still expressed the IL-60-BS-GUS vector, as indicated by PCR, (see FIG. 2; lane 15) and GUS staining (see FIG. 5*b*); Lane 1 is a size marker; in lanes 2-10, template DNA was extracted from various progeny plants of the GUS-expressing parent; In lane 2, a weak amplification of GUS is probably due to “mechanical” vector contamination of the seed cortex and not genetic heritability (as explained in Example 6);

FIG. 9*a*), tobacco (*Nicotiana tabacum*; FIG. 9*b*), onion (*Allium cepa*; FIG. 9*c*), cabbage (*Brassica oleracea*; FIG. 9*d*), lettuce (*Lactuca sativa*; FIG. 9*e*), summer squash (*Cucurbita pepo*; FIG. 9*f*), wheat (*Triticum durum*; FIG. 9*g*), dill (*Antheum graveolens*; FIG. 9*h*) and parsley (*Petroselinum crispum*; FIG. 9*i*).

FIGS. 11 *a* and 11*c* illustrate leaves of plants 4 weeks (11*a*) and 5 weeks (11*c*) post treatment while FIGS. 11 *b* and 11*d* illustrate leaves of similar age and position in untreated control plants;

FIG. 14*a*: GUS expression 1 month post-injection (p.i.); FIG. 14*b*: GUS expression 12 months p.i.; FIG. 14*c*: GUS expression in root 12 months p.i.;

FIG. 14*d*: expression of GFP, driven by the 35S promoter, in transgenic tobacco (for comparison). FIG. 14*e*: expression of GFP from IL-60-BS, 3 weeks p.i. in tobacco (images in 14*d* and 14*e* were photographed through a fluorescence binocular); FIGS. 14*f* and 14*g*: IL-60-BS-driven GFP fluorescence in *N. benthamiana* leaf tissue as seen in a dark-field inverted microscope. Image in 14*g* was programmed to show GFP fluorescence in green;

FIGS. 15*a*, 15*b* and 15*c* exemplify engendering of resistance/tolerance and; FIGS. 14*a* and 14*b* depict plants injected with IR-C4-IR 7 days prior to inoculation with TYLCV virus; the plant in FIG. 14*c* is a TYLCV-infected, untreated control; Pictures were taken 30 days post-TYLCV infection.

FIGS. 15*d*, 15*e* and 15*f* depict recovery according to an exemplary embodiment of the invention. FIG. 14*d* depicts a plant injected with IR-C4-IR three months after inoculation with TYLCV virus; new growth of the heavily infected plant was symptomless and the plant overcame stunting and produced flowers and normal-looking fruit; FIG. 15*e* shows the symptom-laden leaves of the lower part of the plant; FIG. 15*f* shows the recovered leaves of the upper part of the plant;

FIG. 15*g* shows PCR products with DNA of the plant of FIG. 15*a* (upper left gel) and the plant of FIG. 15*c* (upper right gel), following 18 to 34 PCR cycles (lanes 1-9); lower gels in FIG. 15*g* show results obtained with the same DNA employed in the upper gels amplified with primers for the constitutive gene PDS as a loading control; FIG. 15*h* shows the results of quantitative PCR obtained from DNA extracted from the recovered upper leaves (upper left frame) and symptom-laden lower leaves of plant D. In each of FIGS. 15 *g* and 15 *h*, the lower PDS panels indicate that PCR products from PDS specific primers is accumulate at the same PCR cycle for each sample confirming that the same amount of RNA template was present in each reaction; the upper panels demonstrate that the TYLCV-CP profile is different from plant to plant; in FIG. 15*g* TYLV-CP first appeared in cycle 27 (lane 7; RNA from a TYLCV-resistant plant and in cycle 9 (lane 1; RNA from a susceptible plant); a shift from cycle 9 to cycle 27 is equivalent to a reduction in titer of $2^{18}$ which is approximately 262000-fold less than the control (In other experiment reductions as great as 16,000,000 fold were observed; data not shown); in FIG. 15*h* leaves which have been infected before injection are compared to leaves emerging after injection; results indicate a reduction of approximately 100,000-fold in the virus titer;

DESCRIPTION OF THE PREFERRED EMBODIMENTS

Figure 1A:
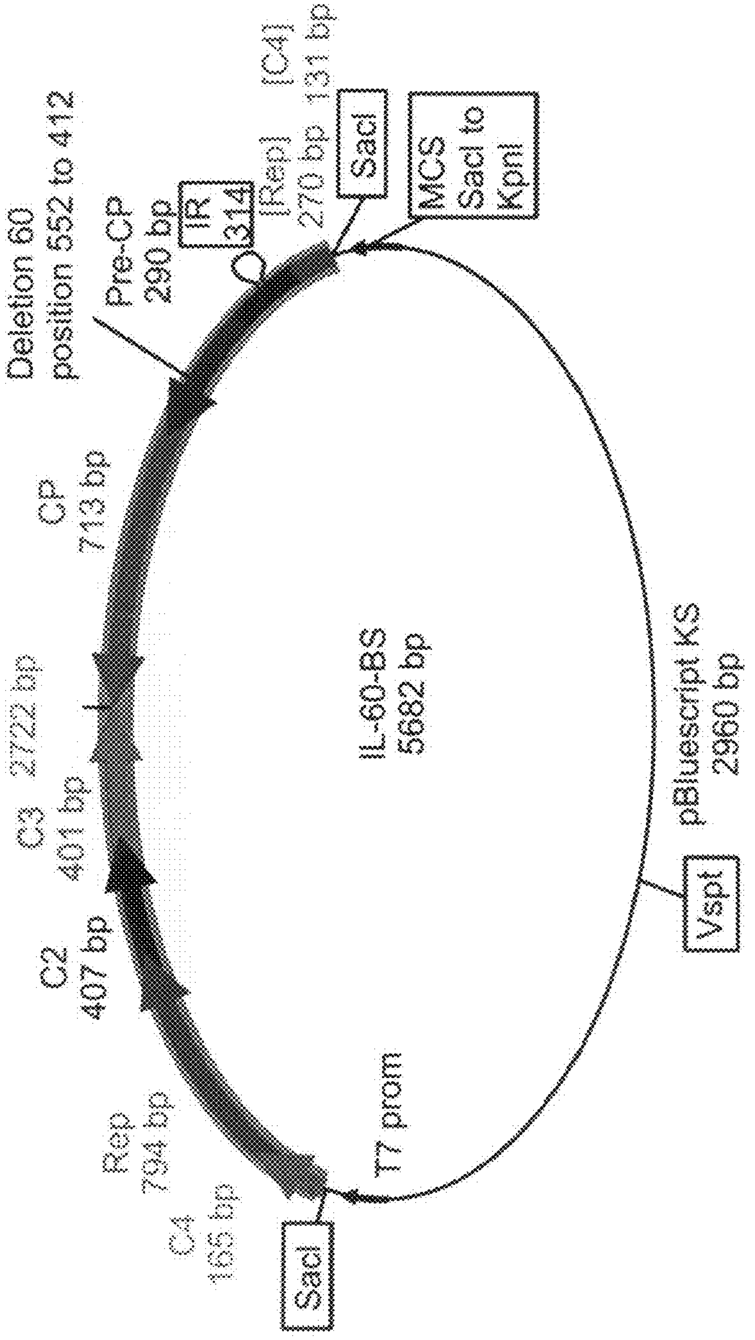
FIG. 1*a* is a map of nucleic acid construct IL-60-BS (SEQ ID NO: 1); colored arrows represent ORFs of TYLCV; thin arc represents pBlueScript plasmid; IR: intergenic region; Prom: promoter; a 60-bp deletion is marked by an arrow.

The present invention is of viral expression vectors and methods which can be used for plant expression and for generating pathogen resistant plants.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Geminivirus-plasmid vectors which are capable of expressing foreign genes are known in the art [Ugaki, M. et al., Nucleic Acids Research 19, 371-377 (1991)]. Such monopartite geminivirus expression vectors possess limited utility since gene insertion abolishes systemic spread of these vectors, thus confining their use to restricted tissues or cell cultures alone.

While reducing the present invention to practice, the present inventors have constructed a geminivirus based nucleic acid construct (also referred to herein as an expression vector) which is capable of systemic symptomeless spread in a host plant and yet is also capable of carrying heterologous polynucleotide inserts which are substantially larger than those carried by prior art geminivirus expression vectors.

As is illustrated in the Examples section hereinbelow, the expression vectors constructed in accordance with the teachings of the present invention are the first reported geminivirus-based vectors that can spread systemically, and express large foreign genes in tissues of non host plants as well as host plants. The application of such vectors in plant expression is easy, and expression is rapid and durable for an entire lifespan of a plant.

In addition, due to their tolerance for large inserts, the present expression vectors can also be configured as a shuttle vector and therefore the propagation and manipulation thereof can be performed rapidly and easily in *E. coli* cells.

Thus, according to one aspect of the present invention there is provided a geminivirus-based nucleic acid construct which is capable of systemic symptomeless spread in a host plant.

As used herein, the phrase "systemic symptomeless spread" refers to the ability of the plant virus-based vector of the present invention to spread, for example, into leaves not serving as the site of infection without inducing the characteristic geminivirus symptoms such as leaf yellowing, leaf curling, stunting of plant growth, or development of flowers or fruit.

Examples of susceptible host species include *Cynanchum acutum, Datura stramonium, Hyoscyamus desertorum, Lens culinaris, Lycopersicon esculentum, Lycopersicon pimpinellifolium, Malva nicaensis, Malva parviflora, Nicotiana benthamiana, Nicotiana glutinosa, Nicotiana tabacum, Phaseolus vulgaris* and *Sonchus oleraceus*, as well as insusceptible host species such as *Abelmoschus esculentus, Althaea rosea, Amaranthus retroflexus, Arachis hypogaea, Atriplex, Beta vulgaris, Calotropis aegyptia, Capparis aegyptia, Chenopodium amaranticolor, Cucumis sativus, Gomphrena globosa, Gossypium hirsutum, Hibiscus rosa-sinensis, Lavatera cretica, Lonicera, Lycium, Medicago sativa, Momordica balsamina, Nerium oleander, Nicotiana rustica, Ochradenus baccatus, Physalis floridana, Pisum sativum, Plumbago capensis, Polygonum equisetiforme, Portulaca oleracea, Prosopis farcta, Ricinus communis, Solanum incanum, Solanum villosum, Tamarix, Tribulus, Vicia faba, Withania somnifera, Xanthium strumarium* and *Zinnia elegans.*

Additional susceptible and insusceptible hosts are listed in http://pheneDOTcpmcDOTcolumbiaDOTedu/ICTVdB/29030000.htm Any geminivirus genome can be used to construct the nucleic acid construct of the present invention. The present invention preferably utilizes a dsDNA construct. Replication of the geminivirus depends solely on host machinery, and only the transition from dsDNA to progeny ssDNA requires a viral protein (the replicase—C1, or replicase associated protein—AC1). Additional viral genes are involved in movement, pathogenicity (e.g. BV1, BC1), enhancement of transcription, suppression of silencing (e.g. AC2) and indirect enhancement of DNA replication via interaction with host DNA replication machinery (e.g. C3, AC3, REn). Therefore, manipulation of the "replicase" of any geminivirus and of the pathogenicity-related genes (V2 or genes on DNA B of dipartite viruses) will provide similar vector characteristics.

Preferred Geminiviruses which can be used with the present invention include the tomato yellow leaf curl virus (TYLCV) as well as other Begomoviruses (see, pheneDOTcpmcDOTcolumbia.edu/ICTVdB/29030000.htm). It will be appreciated that although some of the terminology utilized herein refers to the genes encoded by TYLCV, one of ordinary skill in the art would be more than capable of identifying and utilizing the genetic orthologues of other geminivirus species and strains.

The nucleic acid constructs of the present invention can include one or more modifications (mutations, deletions and/or insertions) which provide the desired functionality, i.e. systemic symptomeless spread.

Preferably, the nucleic acid construct of the present invention includes modifications in a replicase or replicase adjacent region such as the intergenic region (IR). One example of an IR region which can be targeted for modification is the replication-associated protein binding domain (Akbar Behjatnia et al. Nucleic Acids Research, 1998, Vol. 26, No. 4, 925-931).

The rep-protein binding domain of the viral ORI is described hereinbelow. A GGTGTC motif [bases 49-54 and (inverted) 73-68 of GenBank accession # X15656] has been identified as essential for rep-binding. Slight modification of this motif may be used to supplement or replace the rep-disruption approach described in the Examples section (used to construct IL-60-BS).

The Examples section describes replicase modifications which can be used to produce the nucleic acid construct of the present invention. It will be appreciated that additional sites of modification can be identified by the ordinary skilled artisan by simply inducing such modifications and testing for systemic symptomeless spread as outlined in the Examples section which follows.

It should be noted however, that such modifications should be effected with considerations to the functionality of the nucleic acid construct of the present invention (systemic symptomeless spread) and its use (further described hereinbelow).

Additional or alternative modifications include, for example, the C2, C3 and C4 genes which carry auxiliary roles only.

As is further detailed in the Examples section which follows, the above described modifications can be carried out using molecular techniques such as PCR which are well known to the ordinary skilled artisan.

Preferably, the nucleic acid construct of the present invention carries one or more polynucleotide insertions at the preferred sites described above. Such an insert can serve to both produce the desired modification and to provide additional features to the nucleic acid construct of the present invention. Such an insertion can be several nucleotides, to several thousand nucleotides long. The insert can include a complete eukaryotic or prokaryotic expression vector (see example 1), a polylinker insert or a molecule having a biological activity. In any case, it should be noted that the nucleic acid construct of the present invention can carry inserts which increase the final geminivirus by 20-100% and as much as 200% beyond that of a wild type genome and yet, as is illustrated in the Examples section which follows, the nucleic acid construct of the present invention is capable of efficiently spreading throughout the host plant.

The insert can encode alternative or additional functions including for example, bacterial replication, antibiotic resistance, affinity purification tags and the like.

As is further described in the Examples section which follows, the present inventors have also utilized portions of the geminivirus genome in construction of a transactivatable expression vector. One example of such a vector is provided in Example 5 which illustrates that an IR fragment derived from a geminivirus can induce systemic expression of a linked polynucleotide sequence in a host plant when such a plant is infected with a geminivirus providing helper functions (e.g. the TYLCV derived vector of the present invention).

According to various exemplary embodiments of the invention, the native TYLCV genome is modified in order to achieve a desired functional alteration. For example, the CP of geminiviruses plays no role in viral DNA replication but is involved in viral movement and systemic spread in the plant (Wartig et al. (1997) *Virology* 228, 132-140 (1997); Liu et al. (1998) *J. Gen. Virol.* 79, 2265-2274 and Unseld et al. (2004) *Virology* 318, 90-101). These characteristics have been mapped to the C-terminal part of the CP (Noris. et. al. (1998) *J. Virol.* 72, 10050-10057).

Since one of goal in constructing some exemplary vectors was retention of spreading capacity, the N-terminal part of the CP was altered in some cases. In an exemplary embodiment of the invention, 60 nucleotides (corresponding to positions 552-612) of the TYLCV were deleted, causing the removal of 20 amino acids (positions 27 to 46) from the native viral CP. The resultant CP still carried a bipartite nuclear-localization signal (NLS; amino acids 1-20), although a third part (KRR at position 41-43) of what may have been a tripartite NLS was removed.

Alternatively, or additionally, point mutations were introduced by single-base deletion at position 640 of the native TYLCV-DNA, causing a frameshift which was corrected for by adding a G to position 744 of the native viral DNA. Due to the resultant frameshift, a stretch of amino acids residing between positions 56 and 91 of the native CP became different, with no apparent similarity to the corresponding stretch (positions 36 to 71) of IL-60-CP. Beyond that point, however, the CP sequences of TYLCV and IL-60 were almost identical. Due to the changes in amino acids 56 to 91, the conserved sequence GCEGPCKVQS (SEQ ID no.: 52), carried by all geminoviruses tested to date (Kirthi et al. (2003) *Arch. Virol.* 148, 2369-2380), is missing from IL-60. In many viruses (but not TYLCV), this sequence is part of a zinc-finger motif required for attachment to single-stranded (ss) DNA (apparently for encapsidation), a property that is redundant for a vector. Deletion at the N terminus of CP also resulted in a deletion of 45 amino acids at the C terminus of the overlapping ORF V2 ("pre-coat"). Motif searches available at PROSITE (such as ELM and MotifScan) indicated that the deleted sequence includes a number of protein:protein recognition motifs such as SH2, SH3, PDZ and a motif recognized by SUMO (a ubiquitin-like protein) for modification. Apparently, TYLCV "pre-coat" functions within higher-order protein complexes, and the removal of these motifs interferes with the scaffolding of the aforementioned putative complexes. The rep gene product of geminiviruses is involved in rolling-circle replication (Saunders et al. (1991) *Nucleic Acids Res.* 19, 2325-2330), i.e. the conversion of the gene-expressing dsDNA replicative form to ssDNA progeny. Recognition of, and binding to, the origin of replication, as well as initiation of rolling-circle replication by nicking at the origin, are all attributed to the N terminus of rep (Campos-Olivas et al. (2002)*Proc. Natl. Acad. Sci.* USA 99, 10310-10315). For use as a biotechnological tool, only the replication of, and expression from dsDNA (which rely solely on host factors) are required and the conversion of ssDNA to dsDNA, as well as the synthesis of single-stranded progeny, are immaterial. Therefore, the plasmid component of the vector was cloned within the N-terminal part of rep. IL-60-BS was constructed such that the plasmid, inserted at position 279 of TYLCV, interrupted the rep protein at position 93. The catalytic domain of rep is composed of three motifs. Motif III carries an α helix (positions 99-106), including the catalytic tyrosine (Y103; Y101 in the reported isolate of TYLCV) which is required for nicking[37]. The insertion of the plasmid at this position also interrupted ORF C4 which is involved in symptom expression Rigden et al. (1994) *Virology* 204, 847-850; Krake et al. (1998) *Mol. Plant. Mirob. Interact.* 11, 413-417 and Selth et al. (2004) *Mol. Plant. Microb. Interact.* 17, 27-33 (2004), thus contributing to the disarming of the virus. The aforedescribed alterations are all consistent with a disarmed dsDNA construct which is capable of replicating (dsDNA to dsDNA) by attracting the host machinery to its origin of replication and retaining its mobility, but with no ability to produce progeny viral ssDNA. In fact, a plant episome has been engineered which, along with the bacterial plasmid component, can shuttle between bacteria and plants.

In an exemplary embodiment of the invention, a nucleic acid construct includes at a least a portion of an IR region of a geminivirus covalently linked to a polynucleotide sequence of interest.

The IR derived sequence can include for example, a nucleotide region defined by coordinates 1-314 or 62-314 of TYLCV (GenBank Accession number X15656).

As further described herein the transactivation, can be effected by co-administering the transactivatable expression vector and its helper component or by stepwise introduction of the helper and transactivatable expression vector.

Any geminivirus or geminivirus derived vector can be used to provide the helper functions described herein. Preferably, this helper component is attenuated in disease causing capabilities, one example of such a component is the geminivirus derived plasmid of the present invention which includes a BlueScript insert (see Example 1). Additional examples include other variants of TYLCV (for example: the Sardinian strain, the Australian strain, New Delhi strain, Chinese strain etc.) and other mono- or bi-partite begomoviruses such as Beet dwarf mosaic virus, and cassava mosaic virus (see, Fauquet, C. M. et al., Archives of Virology 148:405-421, 2003).

One preferred use for the nucleic acid constructs of the present invention is plant expression of a polynucleotide or a polypeptide.

One of ordinary skill in the art is familiar with nucleic acids or proteins whose expression, controlled by the expression vector of the present invention, is advantageous. Furthermore, the skilled artisan is familiar with genes whose repression or deletion, by means of expression of, for example, a suitable double-stranded RNA, or an antisense RNA, would lead to a desired effect.

Nucleic acid sequences whose expression under the control of the expression vector of the present invention has advantageous effects are exemplified below.

The expressed polynucleotide sequence can encode a molecule which would protect the plant from abiotic stress factors such as drought, heat or chill. Examples include antifreeze polypeptides from *Myoxocephalus Scorpius* (WO 00/00512), *Myoxocephalus octodecemspinosus*, the *Arabidopsis thaliana* transcription activator CBF1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechn Genet Eng Rev 15:1-32), DREB1A factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

The expressed polynucleotide sequence could be a metabolic enzyme for use in the food-and-feed sector. Examples include, phytases (GenBank Acc. No.: A19451) and cellulases.

The expressed polynucleotide sequence can confer resistance to viruses, fungi, insects, nematodes and diseases, by directly attacking the pathogen, turning on the host defenses or by leading to an accumulation of certain metabolites or proteins. Examples of include glucosinolates (defense against herbivores), chitinases or glucanases and other enzymes which destroy the cell wall of parasites, ribosome-inactivating proteins (RIPS) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, α-amylase inhibitor or protease inhibitors (cowpea trypsin inhibitor), lectins such as wheatgerm agglutinin, siRNA, antisense RNA, RNAses or ribozymes. Further examples are nucleic acids which encode the *Trichoderma harzianum* chit42 endochitinase (GenBank Acc. No.: S78423) or the N-hydroxylating, multi-functional cytochrome P-450 (CYP79) protein from *Sorghum bicolor* (GenBank Acc. No.: U32624), or functional equivalents thereof.

Accumulation of glucosinolates as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328: 33-37) or the protection against attack by fungi, by expression of chitinases, for example from beans (Broglie et al. (1991) Science 254:1194-1197), is advantageous. Resistance to pests such as, for example, the rice pest *Nilaparvata lugens* in rice plants can be achieved by expressing the snowdrop (*Galanthus nivalis*) lectin agglutinin (Rao et al. (1998) Plant J 15(4):469-77).

The expression of synthetic cryIA(b) and cryIA(c) genes, which encode lepidoptera-specific *Bacillus thuringiensis* delta-endotoxins can bring about a resistance to insect pests in various plants (Goyal R K et al. (2000) Crop Protection 19(5):307-312).

Additional genes which are suitable for pathogen defense comprise "polygalacturonase-inhibiting protein" (PGIP), thaumatine, invertase and antimicrobial peptides such as lactoferrin (Lee T J et al. (2002) J Amer Soc Horticult Sci 127(2):158-164).

The expressed polynucleotide sequence can bring about an accumulation of chemicals such as of tocopherols, tocotrienols or carotenoids. One example of such a polynucleotide is phytoene desaturase. Preferred are nucleic acids which encode the *Narcissus pseudonarcissus* photoene desaturase (GenBank Acc. No.: X78815) or functional equivalents thereof.

The expressed polynucleotide sequence can be used for production of nutraceuticals such as, for example, polyunsaturated fatty acids (arachidonic acid, eicosapentaenoic acid or docosahexaenoic acid) examples include, fatty acid elongases and/or desaturases, or for production of proteins with improved nutritional value such as, for example, with a high content of essential amino acids (for example the high-methionine 2S albumin gene of the brazil nut). Preferred are polynucleotide sequence which encode the *Bertholletia excelsa* high-methionine 2S albumin (GenBank Acc. No.: AB044391), the *Physcomitrella patens* delta6-acyl-lipid desaturase (GenBank Acc. No.: AJ222980; Girke et al. (1998) Plant 15:39-48), the *Mortierella alpina* delta6-desaturase (Sakuradani et al. 1999 Gene 238:445-453), the *Caenorhabditis elegans* delta5-desaturase (Michaelson et al. 1998, FEBS Letters 439:215-218), the *Caenorhabditis elegans* A5-fatty acid desaturase (des-5) (GenBank Acc. No.: AF078796), the *Mortierella alpina* delta5-desaturase (Michaelson et al. JBC 273:19055-19059), the *Caenorhabditis elegans* delta6-elongase (Beaudoin et al. 2000, PNAS 97:6421-6426), the *Physcomitrella patens* delta6-elongase (Zank et al. 2000, Biochemical Society Transactions 28:654-657), or functional equivalents of these.

The expressed polynucleotide sequence can be used for production of high-quality proteins and enzymes for industrial purposes (for example enzymes, such as lipases) or as pharmaceuticals (such as, for example, antibodies, blood clotting factors, interferons, lymphokins, colony stimulation factor, plasminogen activators, hormones or vaccines, as described by Hood E E, Jilka J M (1999) Curr Opin Biotechnol 10(4):382-6; Ma J K, Vine N D (1999) Curr Top Microbiol Immunol 236:275-92). For example, it has been possible to produce recombinant avidin from chicken albumen and bacterial P-glucuronidase (GUS) on a large scale in transgenic maize plants (Hood et al. (1999) Adv Exp Med Biol 464:127-47. Review).

The expressed polynucleotide sequence can be used for obtaining an increased storability in cells which normally comprise fewer storage proteins or storage lipids, with the purpose of increasing the yield of these substances. Examples include, acetyl-CoA carboxylase. Preferred polynucleotide sequence are those which encode the *Medicago sativa* acetyl-CoA carboxylase (accase) (GenBank Acc. No.: L25042), or functional equivalents thereof.

Additional examples of expressible polynucleotides include Hepatitis B surface antigen [Kumar G B S et al., PLANTA 222 (3): 484-493, 2005], herbicide resistance [Duke, S O, *Pest Management Science* 61:211-218, 2005], interferon [Edelbaum, O. et al., *J. Interferon Res.* 12: 449-453, 1992], T7-RNA polymerase [Zeitoune et al., *Plant Science* 141:59-65, 1997].

Further examples of polynucleotide sequence which can be expressed by the expression vector of the present invention are mentioned for example in Dunwell J M, Transgenic approaches to crop improvement, J Exp Bot. 2000; 51 pages 487-96.

The expression vector of the present invention can also be employed for the reduction (suppression) of transcription and/or translation of target genes. Thus, the expression vector of the present invention can express nucleic acids which bring about PTGS (post transcriptional gene silencing) or TGS (transcriptional silencing) effects and thus a reduction of the expression of endogenous genes. Such reduction can be achieved for example by expression of an antisense RNA (EP-A1 0 458 367; EP-A1 0 140 308; van der Krol A R et al. (1988) BioTechniques 6(10):658-676; de Lange P et al. (1995) Curr Top Microbiol Immunol 197:57-75, inter alia) or of a double-stranded RNA, each of which has homology with the endogenous target gene to be suppressed. Also, the expression of a suitable sense RNA can bring about a reduction of the expression of endogenous genes, by means of what is known as co-suppression (EP-A1 0 465 572). Especially preferred is the expression of a double-stranded small interfering RNA (siRNA) for reducing the gene expression of a target gene via RNA interference (RNAi). WO 99/32619 and WO 99/53050 describe methods for inhibiting individual target genes using an RNA with double-stranded structure, where the target gene and the region of the RNA duplex have at least partial identity (see also: Montgomery M K et al. (1998) Proc Natl Acad Sci USA 95:15502-15507; Sharp P A (1999) Genes & Development 13(2):139-141; Fire A et al. (1998) Nature 391:806-11).

The following exemplifies applications where reduction of gene expression can be employed using the expression vector of the present invention.

Delayed fruit maturation or a modified maturation phenotype (prolonged maturation, later senescence) can be achieved for example by reducing the gene expression of genes selected from the group consisting of polygalacturonases, pectin esterases, beta.-(1,4)glucanases (cellulases), beta.-galactanases (.beta.-galactosidases), or genes of ethylene biosynthesis, such as 1-aminocyclopropane-1-carboxylate synthase, adenosylmethionine hydrolase (SAMase), aminocyclopropane-1-carb-oxylate deaminase, aminocyclopropane-1-carboxylate oxidase, genes of carotenoid biosynthesis such as, for example, genes of pre-phytoene biosynthesis or phytoene biosynthesis, for example phytoene desaturases, and O-methyltransferases, acyl carrier protein (ACP), elongation factor, auxin-induced gene, cysteine(thiol) proteinases, starch phosphorylases, pyruvate decarboxylases, chalcone reductases, protein kinases, auxin-related gene, sucrose transporters, meristem pattern gene. Further advantageous genes are described for example in WO 91/16440, WO 91/05865, WO 91/16426, WO 92/17596. WO 93/07275 or WO 92/04456. Especially preferred is the reduction of the expression of polygalacturonase for the prevention of cell degradation and mushiness of plants and fruits, for example tomatoes. Nucleic acid sequences such as that of the tomato polygalacturonase gene (GenBank Acc. No.: x14074) or its homologs are preferably used for this purpose.

Improved protection against abiotic stress factors (heat, chill, drought, elevated moisture, pollutants, UV radiation). It is preferred to reduce the expression of genes which are implicated in stress reactions.

The reduction of the gene expression of genes encoding storage proteins (hereinbelow SPs) has numerous advantages, such as, for example, the reduction of the allergenic potential or modification regarding composition or quantity of other metabolites, such as, for example, oil or starch content.

Resistance to plant pathogens such as arachnids, fungi, insects, nematodes, protozoans, viruses, bacteria and diseases can be achieved by reducing the gene expression of genes which are essential for the growth, survival, certain developmental stages (for example pupation) or the multiplication of a specific pathogen. Such a reduction can bring about a complete inhibition of the abovementioned steps, or else a delay of same. They can take the form of plant genes which for example make possible the penetration of the pathogen, but may also be homologous pathogen genes. The transgenically expressed nucleic acid sequence (for example the double-stranded RNA) is preferably directed against genes of the pathogen. The antipathogenic agent which acts may be, in this context, the transgenically expressed nucleic acid sequence itself (for example the double-stranded RNA), but also the transgenic expression cassettes or transgenic organisms. The plants themselves, in the form of a transgenic organism, may contain the agents and pass them on to the pathogens, for example in the form of a stomach poison. Various essential genes of a variety of pathogens are known to the skilled artisan (for example for nematode resistance WO 93/10251, WO 94/17194).

Virus resistance can be achieved for example by reducing the expression of a viral coat protein, a viral replicase, a viral protease and the like. A large number of plant viruses and suitable target genes are known to the skilled artisan.

Reduction of undesired, allergenic or toxic plant constituents such as, for example, glucosinolates or patatin. Suitable target genes are described (in WO 97/16559, inter alia). The target genes which are preferred for reduction of allergenic proteins are described for example by Tada Y et al. (1996) FEBS Lett 391(3):341-345 or Nakamura R (1996) Biosci Biotechnol Biochem 60(8):1215-1221.

Delayed signs of senescence. Suitable target genes are, inter alia, cinnamoyl-CoA:NADPH reductases or cinnamoyl-alcohol dehydrogenases. Further target genes are described (in WO 95/07993, inter alia).

Reduction of the susceptibility to bruising of, for example, potatoes by reducing for example polyphenol oxidase (WO 94/03607) and the like.

Increase of the methionine content by reducing threonine biosynthesis, for example by reducing the expression of threonine synthase (Zeh M et al. (2001) Plant Physiol 127(3): 792-802).

It will be appreciated that the nucleic acid construct of the present invention can also express homologues of the above described molecules that exhibit the desired activity (i.e., the biological activity). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, identical to any of the expressed sequences described above as determined using the BestFit software of the Wisconsin sequence analysis package, utilizing the Smith and Waterman algorithm, where gap weight equals 50, length weight equals 3, average match equals 10, and average mismatch equals −9.

The nucleic acid construct of the present invention can be utilized to stably or preferably transiently transform plant cells. In stable transformation, the nucleic acid molecule of the present invention is integrated into the plant genome, and as such it represents a stable and inherited trait. In transient transformation, the nucleic acid molecule is expressed by the cell transformed but not integrated into the genome, and as such represents a transient trait.

There are various methods of introducing foreign genes into both monocotyledonous and dicotyledonous plants (Potrykus, I. (1991). Annu Rev Plant Physiol Plant Mol Biol 42, 205-225; Shimamoto, K. et al. (1989). Fertile transgenic rice plants regenerated from transformed protoplasts. Nature (1989) 338, 274-276).

The principal methods of the stable integration of exogenous DNA into plant genomic DNA include two main approaches:

(i) *Agrobacterium*-mediated gene transfer. See: Klee, H. J. et al. (1987). Annu Rev Plant Physiol 38, 467-486; Klee, H. J. and Rogers, S. G. (1989). Cell Culture and Somatic Cell Genetics of Plants, Vol. 6, Molecular Biology of Plant Nuclear Genes, pp. 2-25, J. Schell and L. K. Vasil, eds., Academic Publishers, San Diego, Cal.; and Gatenby, A. A. (1989). Regulation and Expression of Plant Genes in Microorganisms, pp. 93-112, Plant Biotechnology, S. Kung and C. J. Arntzen, eds., Butterworth Publishers, Boston, Mass.

(ii) Direct DNA uptake. See, e.g.: Paszkowski, J. et al. (1989). Cell Culture and Somatic Cell Genetics of Plants, Vol. 6, Molecular Biology of Plant Nuclear Genes, pp. 52-68, J. Schell and L. K. Vasil, eds., Academic Publishers, San Diego, Cal.; and Toriyama, K. et al. (1988). Bio/Technol 6, 1072-1074 (methods for direct uptake of DNA into protoplasts). See also: Zhang et al. (1988). Plant Cell Rep 7, 379-384; and Fromm, M. E. et al. (1986). Stable transformation of maize after gene transfer by electroporation. Nature 319, 791-793 (DNA uptake induced by brief electric shock of plant cells). See also: Klein et al. (1988). Bio/Technology 6, 559-563; McCabe, D. E. et al. (1988). Stable transformation of soybean (*Glycine max*) by particle acceleration. Bio/Technology 6, 923-926; and Sanford, J. C. (1990). Biolistic plant transformation. Physiol Plant 79, 206-209 (DNA injection into plant cells or tissues by particle bombardment). See also: Neuhaus, J. M. et al. (1987). Theor Appl Genet. 75, 30-36; and Neuhaus, J. M. and Spangenberg, G. C. (1990). Physiol Plant 79, 213-217 (use of micropipette systems). See U.S. Pat. No. 5,464,765 (glass fibers or silicon carbide whisker transformation of cell cultures, embryos or callus tissue). See also: DeWet, J. M. J. et al. (1985). “Exogenous gene transfer in maize (*Zea mays*) using DNA-treated pollen,” Experimental Manipulation of Ovule Tissue, G. P. Chapman et al., eds., Longman, New York-London, pp. 197-209; and Ohta, Y. (1986). High-Efficiency Genetic Transformation of Maize by a Mixture of Pollen and Exogenous DNA. Proc Natl Acad Sci USA 83, 715-719 (direct incubation of DNA with germinating pollen).

The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation (Horsch, R. B. et al. (1988). “Leaf disc transformation.” Plant Molecular Biology Manual A5, 1-9, Kluwer Academic Publishers, Dordrecht). A supplementary approach employs the *Agrobacterium* delivery system in combination with vacuum infiltration. The *Agrobacterium* system is especially useful for in the creation of transgenic dicotyledenous plants.

There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues. Additional direct DNA transfer techniques include glass or silicone carbide whiskers (see, for example, Dunwell, Methods Mol. Biol. 1999; 111:375-82).

Following stable transformation, plant propagation then occurs. The most common method of plant propagation is by seed. The disadvantage of regeneration by seed propagation, however, is the lack of uniformity in the crop due to heterozygosity, since seeds are produced by plants according to the genetic variances governed by Mendelian rules. In other words, each seed is genetically different and each will grow with its own specific traits. Therefore, it is preferred that the regeneration be effected such that the regenerated plant has identical traits and characteristics to those of the parent transgenic plant. The preferred method of regenerating a transformed plant is by micropropagation, which provides a rapid, consistent reproduction of the transformed plants.

Micropropagation is a process of growing second-generation plants from a single tissue sample excised from a selected parent plant or cultivar. This process permits the mass reproduction of plants having the preferred tissue and expressing a fusion protein. The newly generated plants are genetically identical to, and have all of the characteristics of, the original plant. Micropropagation allows for mass production of quality plant material in a short period of time and offers a rapid multiplication of selected cultivars with preservation of the characteristics of the original transgenic or transformed plant. The advantages of this method of plant cloning include the speed of plant multiplication and the quality and uniformity of the plants produced.

Micropropagation is a multi-stage procedure that requires alteration of culture medium or growth conditions between stages. The micropropagation process involves four basic stages: stage one, initial tissue culturing; stage two, tissue culture multiplication; stage three, differentiation and plant formation; and stage four, greenhouse culturing and hardening. During stage one, the tissue culture is established and certified contaminant-free. During stage two, the initial tissue culture is multiplied until a sufficient number of tissue samples are produced to meet production goals. During stage three, the newly grown tissue samples are divided and grown into individual plantlets. At stage four, the transformed plantlets are transferred to a greenhouse for hardening where the plants' tolerance to light is gradually increased so that they can continue to grow in the natural environment.

Transient transformation of, for example, leaf cells, meristematic cells, or the whole plant is also envisaged by the present invention.

Transient transformation can be effected by any of the direct DNA transfer methods described above or by mechanical or vector mediated viral infection using the plant viruses derived plasmid of the present invention.

Thus, the present invention provides a geminivirus based nucleic acid construct which spreads systemically throughout the host plant and yet does not induce symptoms therein.

The nucleic acid construct of the present invention can be utilized for any purpose. Examples of uses include the following:

(i) plant expression of proteins (specific examples provided hereinabove) for various purposes including plant improvement, biopharming etc;

(ii) plant expression of nucleic acid molecules (e.g. siRNA, specific examples provided hereinabove);

(iii) produce indicator plants which detect viral infection—a plant carrying a construct including a reporter molecule (e.g. fluorophore) attached to the IR region would express the reporter in when infected by a geminivirus; and (iv) produce infection-resistant plants—a plant carrying a construct including an anti-viral or anti-plant molecule attached, for example, to the IR region would express such a molecule when infected by a geminivirus; such "immunity" or suicide scheme would only be active when the plant is infected; since the nucleic acid constructs of the present invention are preferably transient and not stably integrated into a genome of the host plant, such a trait would not be inherited by the progeny of the plant nor would it persist in commercial products of the plant.

As used herein the term "about" refers to ±10%.

Safety Considerations

The agricultural use of genomically-modified plants is a matter of public debate, and in many countries is unacceptable by law or regulation. The main considerations voiced against the use of transgenic plants are the fear of inappropriate selection of a transgenic lineage (due to masked deleterious positional effects), possible cross-fertilization with weeds and other crops, further genome alterations due to recombination (especially when copies of endogenous genes are added) and possible transduction of the foreign sequences to plant and soil microorganisms.

Introduction of antibiotic-resistant genes to food and the environment is also a major concern. Biosafety and environmental aspects can only be concluded upon following actual, carefully controlled, field tests over time. Clearance to conduct such experiments depends on evaluation based on hard laboratory data. As discussed in Examples presented hereinbelow, vector systems according to many exemplary embodiments of the invention are potentially biosafe. A-priori, they appear to be environmentally-friendly and ready for biosafety-evaluation field tests. Geminiviruses are not seed-transmissible (Kashina et al. 2003) *Phytoparasitica* 31, 188-199 (2003).

Analysis of the progeny of GUS-expressing plants indicated that the cloned trait is not inherited. The single occasion in which GUS expression was noted in a progeny plant was probably due to vector contamination of the seed cortex, as has been seen with several viruses (e.g. Tomato mosaic virus; Hadas, R. et al. (2004) *Phytoparasitica* 32, 421-424). However, even on this rare occasion, the vector was not inherited by further generations. The presently reported vector forms (IL-60-BS alone and/or with IR-pD) are not insect-transmissible even when the plants are colonized with a large number of insect vectors. In addition, molecular vector constructs for propagation and expression in plants can be made devoid of antibiotic resistance and of the bacterial ORI. A priori, this should prevent the spread of IL-60-derived constructs to the environment, as they would not be able to replicate even if a rare event of transduction to other bacteria occurs.

Being non-inheritable, fear of cross-fertilization is minimized. The IL-60-derived constructs do not integrate into the host's genome, and thus the possibility of deleterious positional effects is irrelevant. Recombination events take place at the meiosis stage of DNA replication (i.e. in gametes) while the vector's replication occurs in somatic cells. In conclusion, we offer a new technology which might ease public and legislative environmental concerns. The IL-60 system is ready for careful environmental studies in order to corroborate the expected non-hazardous properties of the constructs prior to licensing their wide-scale use.

Exemplary Use Scenarios

The IL-60 system provides a basis for several biotechnological uses. The rate of expression of foreign genes in the presently described system is comparable to that of the best known expression levels in transgenic plants. The easy handling of the IL-60-derived expression systems and the postulated circumvention of environmental concerns may contribute to the large-scale "biofarming" of economically-important proteins and pharmaceuticals. The accumulation of the expressed foreign protein in the vacuole, may minimize deleterious effect of its over-accumulation in cells. This system may also be very useful in agriculture, as it allows the easy and non-heritable introduction of a new trait in an environmentally safe manner.

In an exemplary embodiment of the invention, large-scale introduction of an external trait into plants at the nursery becomes feasible and simple. The BIM-LAB instrument (BIO-OZ Biotechnologies Ltd., Yad-Mordechi, Mobile Post Hof-Ashkelon, Israel 79145) can deliver IL-60-BS to several hundreds of tomato plants per day and the BIM-TEN instrument to over 500,000 seedlings per day. The BIM devices should, however, be adjusted for every crop separately. Consequently, a crop carrying a new trait in a non-transgenic manner can be (apparently safely) grown in the field. While plant transformation is, in most cases, laborious and lengthy, the aforedescribed procedures are simple, and the affected plants express the introduced gene's product within 3 days to 2 weeks. Until now, transformation of some important crops, such as wheat, pepper and grapevine, has proven difficult and inefficient. Thus, the system described here may be the method of choice for the safe introduction of new traits in such important crops which, otherwise, can hardly be manipulated.

Overall, the vector technology described herein is applicable to a wide range of traditional crop improvement and/or pharming strategies. Optionally, described exemplary vectors comprise non-transgenic silent agents which are activated only following viral (e.g. TYLCV) infection, bringing about resistance/tolerance to the viral infection. In an exemplary embodiment of the invention, this strategy produces resistance/tolerance in a few days post injection, as compared to conventional breeding which, after many years of development, may be only partially successful.

By itself, transgenic C4 has been shown to produce disease symptoms in plants (Chellappan et al. (2005) *Proc. Natl. Acad. Sci. U.S.A.* 102, 10381-10386 and Latham et al. (1997)

*Plant J.* 11, 1273-1283). This was postulated to result from C4's ability to bind single-stranded forms of siRNA, thus interfering with normal miRNA-directed developmental processes (Latham, Ibid.). Mutations in C4 resulted in lack of systemic spread and reduced levels of virus in tomato plants, and it was therefore considered to be associated with movement (Jupin et al. (1994) *Virology* 204, 82-90).

It seems, more likely, however, that C4 modification or silencing allows the plant's silencing mechanism to degrade at least the antisense-oriented transcript of TYLCV.

In summary, exemplary vectors according to different embodiments of the invention provide a plant-bacterial shuttle expression system engineered to be symptomless, harmless and flexible. It is easily manipulated, delivered to and propagated in a wide range of plants, including monocots. Expression can be detected within three days. Transcription or agroinoculation steps are not necessary. Its easy handling makes it user-friendly, and being non-transgenic, nonheritable, and devoid of selectable genes for antibiotic resistance, it is environmentally friendly as well.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion. Before presenting examples, a list of methods and materials is provided.

Methods and Materials

Agroinoculation—Agroinoculation of TYLCV and IL-60, was carried out as described in Czosnek. H., et al., [Plant Mol. Biol. 22, 995-1005 (1993)].

Cloning of TYLCV—A full 2.8-genome-length clone of the Israeli strain of TYLCV (SEQ ID NO: 4 GenBank accession # X15656) was produced as described in Navot, N., et al [Virology 185, 151-161 (1991)].

The construction of IL-60—The IL-60 vector (SEQ ID NO: 2) of the present invention was constructed by making the following changes to the native TYLCV viral vector (SEQ ID NO: 4):

(i) a deletion of a stretch of 60 nucleotides (nos. 552 to 612 of SEQ ID NO: 1) encoding 20 amino acids near the N-terminus of the coat protein, TYLCV-CP (nos. 27 to 46 of SEQ ID NO: 5). Deletion was carried out by inverse PCR in accordance with Livneh, O. et al. [Euphytica 62:97-102 (1992)] using primers directed outward from the ends of the deleted segment [Inverse forward primer (unphosphorylated): OH-acaggcccatagaccgaaagccca; SEQ ID NO: 14, Inverse reverse (phosphorylated): P-tgggctgtcgaagttcagcct; SEQ ID NO: 15]. The self-ligated PCR product was cleaved with SacI to produced a single (linear) product, confirming that a circular form has been made (non-ligated, linear PCR products would have produced two fragments upon cleaving).

(ii) a PCR derived deletion of T in position 640 (of TYLCV) and addition of G at following position 744 thereby generating a frame shift in the TYLCV sequence (SEQ ID NO: 4) encoding positions 56-91 of native TYLCV-CP protein (SEQ ID NO: 5, see also FIGS. 1*c* and *d*). Frame shift was achieved in 2 steps, first aimed at deleting the T and second at adding the G. The first step aimed at deleting the T at position 640 included two PCR steps, an initial and nested PCR. The initial PCR product was cut with TaqI, and a mutated (missing the T) nested PCR product, which was situated between 2 TaqI restriction sites, was ligated instead of the cut out piece. Initial PCR amplified a 439 bp product flanked with TaqI restriction sites, and possessing two middle TaqI restriction sites. [forward primer: ggctgaacttcgacagcccatacagcagccgtgctgctg (SEQ ID NO: 20), BcefI recognition site is emphasized in bold, TaqI restriction site is underlined; reverse primer: gcggtactgggctcattatatcgaacatatt (SEQ ID NO: 21), BmrI recognition site is emphasized in bold, TaqI restriction sites is underlined]. Nested PCR amplified a product flanked by the same TaqI restriction site at the forward end (using the same forward primer—SEQ ID NO: 20) and another middle TaqI restriction site at the reverse end. The reverse primer also possessed the missing respective T [nested reverse primer: ggcttcgatacattctgtat↑ttctg (SEQ ID NO: 22), TaqI recognition site is emphasized in bold, arrow represents the position of the deleted T]. The initial PCR product was cleaved with TaqI and run on a gel, to obtain 3 bands (from the 2 flanking and 2 middle TaqI restriction sites). The upstream piece, situated between the primers of the nested PCR, was removed. The remaining 2 bands were extracted from the gel and ligated to the mutated PCR product of the nested PCR to obtain the desired sequence (BcfI to TaqI with a missing T). The second step, aimed at adding the G at position 744, involved an initial PCR with primers holding BstDSI (forward) and MaeIII (reverse) restriction sites [forward primer: ctgatgttccccgtggatgtgaaggcccat (SEQ ID NO: 23), BstDSI recognition site is emphasized in bold; reverse primer: ccacgagtaacatcactaacaacCaacaatac (SEQ ID NO: 24), MaeIII recognition site is emphasized in bold, added G (C in the reverse complement) is also emphasized in bold], to obtain a PCR product holding the additional G. The PCR product, and the product of the first step (BcfI to TaqI with a missing T) were cleaved with BstDSI and MaeIII, and the cleavage product was replaced with the PCR product including the added G, by ligation. Finally, IL-60 was cleaved with BceFI and BmrI, a fragment was removed and replaced by the sequence obtained in the steps described above (BcfI to BmrI with a missing T and an added G).

iii) a deletion of 45 amino acids at the C terminus of native TYLCV V2 ("pre-coat"-SEQ ID NO: 6), caused by the deletion of the TYLCV CP described hereinabove.

Construction of IL-60-BS—the IL-60-BS vector (SEQ ID NO: 1) of the present invention was constructed by ligating a linearized (Sac I) Bluescript II-KS+plasmid (Stratagene, La Jolla, Calif., USA) into position 2443 of the IL-60 plasmid (SEQ ID NO: 2), interrupting the rep (rolling circle replication) protein (SEQ ID NO: 7) at position 93, within the N-terminus. The gene coding for C4 (symptom expression) was also interrupted by the BS insertion.

Construction of IL-60-BS-GUS and IL-60-BS-GFP—The IL-60-BS derivatives, IL-60-BS-GUS (SEQ ID NO: 9) and IL-60-BS-GFP (SEQ ID NO: 10) were constructed by insertion of the coding regions of reporter genes β-glucuronidase (GUS), and green fluorescence protein (GFP) into a linearized IL-60-BS vector (SEQ ID NO: 1). The coding region of GUS (bases 1466 to 3274 of GenBank accession # M14641) (SEQ ID NO: 37) was first cleaved out from a GUS-carrying plasmid with SacI and Sal I. The ends of the obtained GUS sequence were made blunt by polishing with T4-DNA-polymerase. The blunt-ended GUS was then inserted into the EcoRV site of IL-60-BS. Similarly, the coding region of GFP (Bases 1 to 797 of GenBank accession # U87974—SEQ ID NO: 38) was cleaved of a GFP-carrying plasmid with SacI and Hind III. Following end-polishing the obtained GFP sequence was inserted into the EcoRV site of IL-60-BS.

Construction and propagation of IL-60-BS$^{amp-}$ and IL-60-BS-GUS$^{amp-}$—the IL-60-BS$^{amp-}$ vector (SEQ ID NO: 11) of the present invention was constructed by cleaving (BspH I) the amp gene [positions 1873 to 2881 of the plasmid pBluescript, including the entire (but 2 bp) ampicillin-coding sequence] out of the pBluescript vector. Following electrophoresis, the 1953-bp-long fragment (the linearized plasmid devoid of amp) was extracted out of the gel, self ligated and inserted into *E. coli* for propagation. The bacteria were then plated on LB-agar. A sample of each blue colony was transferred to a plate with LB-agar and another sample of the same colony to a plate of LB agar with ampicillin (100 microgram per milliter). A blue colony which was ampicillin-susceptible was selected. The plasmid was extracted therefrom and confirmed by PCR and sequencing to be devoid of amp. IL-60 was then inserted into the SacI site of the plasmid, producing IL-60-BS$^{amp-}$. The coding sequences of GUS were later inserted into IL-60-BS$^{amp}$- as aforedescribed for IL-60-BS-GUS, producing IL-60-BS-GUS$^{amp-}$ (SEQ ID NO: 12).

Construction of IR-GUS-pD—The IR-GUS-pD vector (SEQ ID NO: 13) of the present invention was constructed by amplifying the IR region, pre-coat ORF and a part of the 5' UTR of the coat protein ORF-(positions 61 to 473 of TYLCV; accession # X15656) using forward primer 933: atacttggacacctaatggc (SEQ ID NO: 29) and reverse primer 934: agtcacgggcccttacaa (SEQ ID NO: 30). This fragment was termed "IR-region". IR region was T/A cloned into the plasmid pDRIVE, to produce a plasmid called IR-pD (SEQ ID NO: 33). The coding sequence of GUS (bases 1466 to 3274 of GenBank accession # M14641) (SEQ ID NO: 37) was cleaved out of a GUS-carrying plasmid with SacI and SalI and inserted into a SalI/SacI cleaved pDRIVE carrying the aforementioned IR region.

Construction of IR-PDSinvert-Pd (SEQ ID NO: 39) An inverted repeat segment of the tomato gene for phytoene desaturase (SEQ ID NO: 34; nt. 935 to 1133 of PDS, accession no. M88683) was amplified from tomato DNA [using primers—PDS forward: cagccgctttgatttctcc (SEQ ID NO: 35); PDS reverse: cacaccttgctttctcatcc (SEQ ID NO: 36)]. The resultant 198 bp-product was TA-cloned into the plasmid pDrive. The plasmid was then cleaved with BamHI and XbaI and the resultant fragments were self-ligated. Resulting in tandem repeats of various lengths (multiplications of ~200 bp). Following electrophoresis a fragment of ca. 400 by was extracted from the gel. This fragment is a tandem repeat of the PCR product, one repeat in sense orientation and the other in antisense orientation. This fragment was inserted into IR-pD, which had been digested with BamHI or XbaI.

Propagation of the virus-plasmid vectors and their administration to plants—*E. coli* cells were transformed with IL-60 (SEQ ID NO: 2), IL-60-BS (SEQ ID NO: 1), IL-60-BS-GUS and IL-60-BS-GFP and propagated under ampicillin selection; the construct was extracted using standard procedures. IL-60-BS was administered directly into plants, without mediation by *Agrobacterium*. The stem, or leaf petiole, of the recipient plant was punctured by a hypodermic needle. A capillary tube was inserted into the resultant hole, and approximately 2 microgram of DNA (in 100 μl of 5 mM Tris-HCl; pH 8.5) were pipetted into the capillary tube until fully soaked by the plant. For large-scale applications, samples were delivered into plants by the BIM-LAB instrument (Bio-OZ biotechnologies, Yad Mordechai, Israel).

Propagation and administration of the IR-PDSinvert-pD and IL-60-BS was similarly performed.

Co-administration of IR-GUS-pD with IL-60-BS—Co-administration of IR-GUS-pD with IL-60-BS was done by mixing 2 microgram of IL-60-BS and 2 microgram of IR-GUS-pD and administering to the plant as in described in Example 1. In some cases, IL-60-BS (not carrying a reporter gene) was simultaneously injected together with IR-GUS-pD. In other cases. IR-GUS-pD was administered first and IL-60-BS was injected to the plant 14 days later, thereby inducing replication, spread and GUS expression from of the latter. Hitherto, co-administration of IL-60-BS with IR-GUS-pD was performed in 30 tomato plants, 30 tobacco plants and 3 plants belonging to various hosts mention hereinbelow (see results, altogether 93 plants).

Co-administration of IR-PDSinvert-pD with IL-60-BS—Co-administration of IR-PDSinvert-pD (2.5 μg in 30 μl) together with IL-60-BS was done as described in Example 5.

Induced expression from IR-GUS-pD by other helper agents. Fourteen days to after the administration of IR-GUS-pD to tomato plants the plants were inoculated with Tomato yellow leaf curl virus (TYLCV). Infection with native TYLCV was achieved by feeding virus-carrying *Bemisia tabaci* on tomato plants [Cohen S. and Nitzany F. E. Phytopathology 56:1127 1966].

PCR analysis—PCR analysis was carried out according to standard procedures. DNA for PCR analysis was extracted as described in Bernatzky R. and Tanksley, S. D. [Theor. Appl. Genet. 72:314-321 (1986)], from leaves positioned at least 3 leaves above the point of administration. Tomato plants carry Geminivirus sequences in their genome [Ashby, M. K. et al., Plant Mol. Biol. 35, 313-321 (1997)]. Thus, it was also necessary to ascertain that PCR products were obtained from vector templates and not from native viral infection or plant sequences. Therefore, PCR tests were carried out with primers distinguishing IL-60 from TYLCV, or spanning the junction between IL-60 and the plasmid.

(i) primers distinguishing IL-60 from TYLCV; 977 (forward): gaa ggc tga act tcg aca g (SEQ ID NO: 16), 966 (reverse): att ggg ctg ttt cca tag ggc (SEQ ID NO: 17)

(ii) primers which amplify the junction between Bluescript and IL-60; 939 (forward) aga gac acc gat tca ttt caa c (SEQ ID NO: 18); 940 (reverse) gcg gat aac aat ttc aca cag (SEQ ID NO: 19).

In order to detect the presence of plasmids carrying reporter genes, PCR was performed with primers amplifying the reporter gene inserted into IL-60-BS.

iii) GUS specific primers: 408 (forward) gaa caa cga act gaa ctg gca gac (SEQ ID NO: 25); 167 (reverse) cag cgt aag ggt aat gcg ag (SEQ ID NO: 26).

iv) GFP specific primers: 895 (forward) ggc cga att cag taa agg aga ag (SEQ ID NO: 27); 345 (reverse) tgt gtg gac agg taa tgg (SEQ ID NO: 28).

Lack of amplification with primers which amplify the amp sequence (forward primer, 946: gtcgccgcatacactattc, SEQ ID NO: 31; reverse primer, 947: actttatccgcctccatcc SEQ ID NO: 32) indicated the absence of the amp gene.

Plants were tested for the presence of GUS by PCR using GUS sequence specific primers (SEQ ID NO: 25 and NO: 26).

Molecular analysis—Southern analysis was carried out according to standard procedures (e.g as set forth in Sambrook, J. & Russel, D. W. Molecular Cloning, Third Edition. Cold Spring Harbor Laboratory Press, Cold Spring Harbor (2001)). Probes for Southern analysis were labeled by the PCR-DIG procedure (Roche Molecular Biochemicals, Basel, Switzerland). DIG labeled probes (TYLCV-CP—SEQ ID NO: 40) which hybridize with nucleotides 530-908 of the sequence identified by GenBank Accession No. X15656 were prepared according to the manufacturers protocol. Northern and Western analyses were carried out according to standard procedures. Probes for Northern analysis were labeled as described for the Southern blot analysis. Detection of GUS and GFP activities were performed according to published procedures [Jefferson, R. A., EMBO J. 6, 3901-3907 (1987); Blumenthal, A., Plant Science 142, 93-99 (1999)]. Chemiluminescent probes for Western blots were prepared with the SuperSignal West Pico kit (Pierce, Rockford, Ill., USA), using polyclonal antibodies against TYLCV-CP (Bioreba, Reinach, Switzerland) All probes were prepared according to the respective manufacturer's protocol. For the detection of IR-GUS-pD a probe was constructed using GUS specific primers (SEQ ID NO: 25 and NO: 26).

Detection of GUS activity—GUS activity was detected according to published procedures [Jefferson, R. A., EMBO J. 6, 3901-3907 (1987)].

Bioinformatics—TYLCV, IL-60 and IL-60-BS sequences were analyzed for motifs using the motif search utilities ELM and MotifScan, available at PROSITE.

Analysis of IL-60-BS-GUS heritability—plants injected with IL-60-BS-GUS were grown 10 months until fruit production, and their seeds were collected to produce progeny. Expression of GUS in the parental and progeny plants (grown in concomitance), was determined by GUS staining. 20 Two-month-old progeny plants were tested by PCR for the presence of GUS (using primers SEQ ID NO: 25 and NO: 26), of amp (using primers SEQ ID NO: 31 and NO: 32) and of IL-60-BS, by amplifying the junction TYLCV/BS plasmid (using primers SEQ ID NO: 18 and 19).

Assay for Transfer of IL-60-BS by *Bemisia tabaci*—*Bemisia tabaci* were allowed to feed on IL-60-BS-carrying tomato plants (15 insects per plant). Insects were then fed on sucrose and transferred to healthy tomato plants. DNA was extracted from both types of plants and used as a template for PCR using primers which amplify a sequence specific to IL-60 (e.g. SEQ ID NO: 16 and NO: 17) or other relevant primer pairs.

Quantitative PCR was carried out by removing aliquots from an ongoing PCR of a target gene (or cDNA) at different cycles and determining the threshold of band appearance. A similar assay, with the same temples, was carried out with primers for a constitutive gene, and the threshold of its band appearance was determined. Each treatment threshold was given an arbitrary quantitative value according to the formula $\Delta ct=2^{-(ct\ target\ gene\_ct\ constitutive\ gene)}$, Ct being the cycle threshold. The relative quantitative increase/decrease of templates between control and treated plants was estimated from the ratio of their respective Acts.

analysis GFP fluorescence: GFP images were photographed without a filter to detect any native fluorescence derived from leaf damage, and then with a filter (Leica MZ FL III, GFP2). Levels of GFP expression in various treated plants were compared by measuring GFP fluorescence intensity per cell. These determinations were calculated from the microscopic images by the Image Pro 3 program of Media Cybernetics.

Analysis of GUS expression: Levels of GUS expression were determined by MUG assay (Jefferson et al. (1987) *EMBO J.* 6, 3901-3907) and expressed as fluorescence intensity per microgram protein per hour.

PCR primers. Table 1 presents a partial list of PCR primers used in preparation and/or analysis of evetors according to some exemplary embodiments of the invention.

TABLE 1

Details of exemplary PCR primers

| SEQ ID # | Primer desig.* | Sequence 5' → 3' | Description | Use |
|---|---|---|---|---|
| 17 | 966 (rev) | attgggctgtttccatagggc | Bases 928-908 of IL-60 | Distinguish IL-60 from TYLCV |
| 16 | 977 (forw) | gaaggctgaacttcgacag | Bases 530-548 of IL-60 | |
| 18 | 939 (for) | agagacaccgattcatttcaac | Bases 1-21 of IL-60-BS | Bluescript IL-60 junction |
| 19 | 940 (rev) | gcggataacaatttcacacag | Bases 826-845 of BS | |
| 26 | 167 (rev) | cagcgtaagggtaatgcgag | Bases 2468-2449 of GenBank acc. M14641 | GUS-specific |
| 25 | 408 (for) | gaacaacgaactgaactggcagac | Bases 1867-1890 of GenBank acc. M14641 | |
| 28 | 345 (rev) | tgtgtggacaggtaatgg | Bases 694-669 of GenBank acc. U87974 | GFP-specific |
| 27 | 895 (for) | ggccgaattcagtaaaggagaag | Bases 77-99 of GenBank acc. U87974 | |
| 35 | PDS (for) | cagccgctttgatttctcc | Bases 934-953 of GenBank acc. M88683 | Prepare tandem PDS repeats |

TABLE 1-continued

| Details of exemplary PCR primers | | | | |
|---|---|---|---|---|
| SEQ ID # | Primer desig.* | Sequence 5' → 3' | Description | Use |
| 36 | PDS (rev) | cacaccttgctttctcatcc | Bases 1133-1114 of GenBank acc. M88683 | |
| 42 | 18S-rRNA (for) | aggaattgacggaagggcac | Bases 1142-1446 of GenBank acc. AJ236016 | Load control for RT-PCR |
| 43 | 18S rRNA (rev) | gtgcggcccagaacatctaag | Bases 1466-1446 of GenBank acc. AJ236016 | |
| 44 | ORI (for) | (5' phosphorylated)-ggtctgacgctcagtggaacgaaa | Bases 1828-1851 of pBluescript II KS+ (www. Stratagen.com) version 122001 | omit ORI (ColE1) |
| 45 | ORI (rev) | (5'-phosphorylated)-gtgagctgataccgctcgccgcagcc | Bases 1150-1125 of same pBluescript II KS+ | |

Removal of origin of replication: Inverse PCR with phosphorylated primers was performed in order to remove the bacterial ORI (ColE1). The PCR product was gel-purified and ligated. Several samples of the ORI-less vector were applied to bacteria, but none of the bacterial cells became amp-resistant, indicating the inability of this vector to replicate in bacterial cells.

Example 1

Construction of Geminivirus-based Expression Vectors

TYLCV, IL-60, IL-60-BS and reporter gene derivative plasmids were either agroinoculated or injected into tomato plants and their replication and spread was monitored with symptom observation, PCR analysis and Southern blot. The expression of viral and reporter genes was assessed using PCR, Northern and Western analysis, GUS staining and GFP fluorescence as described above in methods and materials.

Changes in the characteristics of the IL-60 and IL-60-BS constructs—The capsid protein (CP) of Geminiviruses has no role in viral DNA replication but is involved in viral movement and systemic spread in the plant. These characteristics have been mapped to the C-terminal part of CP [Noris, E. et al., J. Virol. 72, 10050-10057 (1998)]. Since one of the critical goals in constructing a vector for introduction of genes into plants, was the maintenance of its spreading capacity, only the N-terminal part of CP was altered by the deletion of 60 bases of the TYLCV, causing the removal of 20 amino acids (positions 26 to 46) from the native viral TYLCV-CP (SEQ ID NO: 5). The resultant CP still carried a bipartite nuclear localization signal (NLS; amino acids 1-20 of SEQ ID NO: 5) although a third part (KRR at position 41-43 of SEQ ID NO: 5) of what may have been a tripartite NLS has been removed.

Additionally, a single-base deletion, and a down stream correction single base insertion, caused a frame shift that altered the sequence of amino acids residing between positions 56 and 91 of the native TYLCV-CP (SEQ ID NO: 5; corresponding to positions 36 to 71 of IL-60-CP—SEQ ID NO: 3), beyond that point, however, the CP sequences of TYLCV and IL-60 are almost identical (FIG. 1*c*). Due to the changes in amino acids 56-91, the sequence GCEGPCKVQS (SEQ ID No.: 46) carried by all tested Geminiviruses is missing from IL-60. In many viruses (but not in TYLCV) this sequence is a part of a zinc-finger motif required for attachment to ssDNA (apparently for encapsidation), a property redundant for a vector.

Deletion at the N terminus of CP also resulted in a deletion of 20 amino acids at the C terminus of the overlapping V2 ORF ("pre-coat"—SEQ ID NO: 6). Motif searches using the PROSITE site (e.g. ELM and MotifScan) indicated that the deleted sequence includes a number of protein: protein recognition motifs such as SH2, SH3, PDZ and a motif recognized by SUMO (a ubiquitin-like protein) for modification. Apparently, TYLCV "pre-coat" functions within higher-order protein complexes [Wartig, L. et al. Virology 228, 132-140 (1997)] Without being bound by theory, it is suggested that the removal of these motifs interfered with the proteins scaffolding properties.

The rep gene product of Geminiviruses is involved with rolling circle replication, which involves the conversion of the gene-expressing dsDNA replicative form to a ssDNA progeny. Recognition of, and binding to, the origin of replication, as well as initiating rolling circle replication by nicking at the origin, are all attributed to the N-terminus of rep. For a biotechnological tool, only the double stranded form of the DNA is required. Therefore, the plasmid element (in this case, the BS plasmid) was inserted to IL-60-BS so as to disrupt the rep protein at its N terminus (position 93 within of SEQ ID NO: 7). The catalytic domain of rep is composed of three motifs, motif III carries an α-helix (position 99-106 of SEQ ID NO: 7, partly given below) including the catalytic tyrosine (Y101) which is required for nicking (in positions 1-111 of SEQ ID NO 7: MPRLFKIYAKNYFLTYPNCSLSKEE-ALSQLKKLETPTNKKYIKVCKELHENGE PHLHVLIQFEGKYQCKNQRFFDLVSPNRSAHFHPNIQ AAK↓SSTDVKTYVEKDGNFID, the arrow indicates the position where the protein was interrupted by the plasmid (the Mptif III is underlined).

ORF C4 (SEQ ID NO: 8) is involved in symptom expression. Insertion of the BS plasmid at the N terminus of rep, also interrupted the overlapping ORF C4 (FIG. 1*a*), thus contributing to the symptomless properties of vector infection.

Thus, the above described alterations to the wild type virus led to the generation of a construct which is capable of replicating (dsDNA to dsDNA) by attracting the host machinery to its origin of replication, retains its movement capacity, yet exhibits a reduced capacity for producing viral ssDNA. In fact, a plant episome has been engineered which, along with the bacterial plasmid component, can replicate and express in bacteria as well as in plants.

IL-60 replicates and spreads in tomato plants—in contrast to the native TYLCV, Agroinoculation of tomato plants with the multimeric form of IL-60 resulted in systemic, but symptomless infection. IL-60 infected plants were kept until they set fruit without expressing any harmful symptoms.

Figure 2:
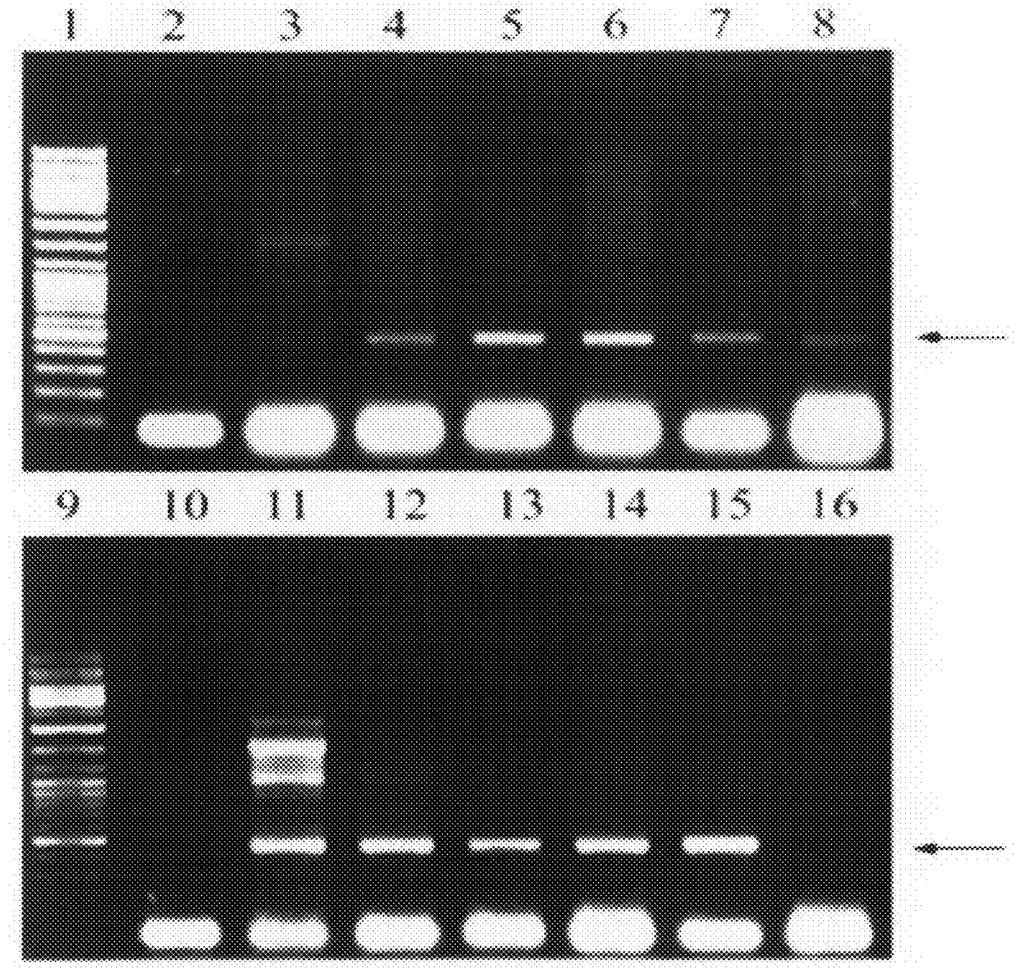
FIG. 2 depicts an ethidium bromide stained gel of PCR products from a post infection time course from a single same Tomato plant infected with the virus-plasmid vector; PCR was performed on DNA template extracted at different times post injection (p.i.) of IL-60-BS-GUS, with primers spanning the virus-plasmid junction of IL-60 and BlueScript (SEQ ID Nos: 18 and 19). Lanes 1 and 9 are size markers, in lanes 2 and 10 DNA was extracted from non-injected plants (negative control), in lane 16 PCR was conducted without a template (negative control), in Lane 11 template was the plasmid IL-60 (positive control), in remaining lanes template DNA was extracted from injected Tomato plant at: 1 day (lane 3), 3 days (lane 4), 7 days (lane 5), 14 days (lane 6), 1 month (lane 7), 2 months (lane 8), 3 months (lane 12), 4 months (lane 13), 6 months (lane 14) and 12 months (lane 15) post injection; arrows indicate the position of the expected 495 bp product.

IL-60-BS replicates and spreads in tomato plants—tomato plants injected with IL-60-BS or IL-60-BS-GUS were analyzed for the presence of the vectors at different times post injection, using PCR analysis with primers aimed at the junction between Bluescript and IL-60 (SEQ ID NO: 18 and 19; FIG. 2). Results show that the vector was found in plants, 3 days post injection (p.i.), and persisted for the duration of the plants life-span (12 months after injection). All the injected plants (more than 64 tomato plants) supported vector replication and spread and did not present any symptom.

Figure 3A:
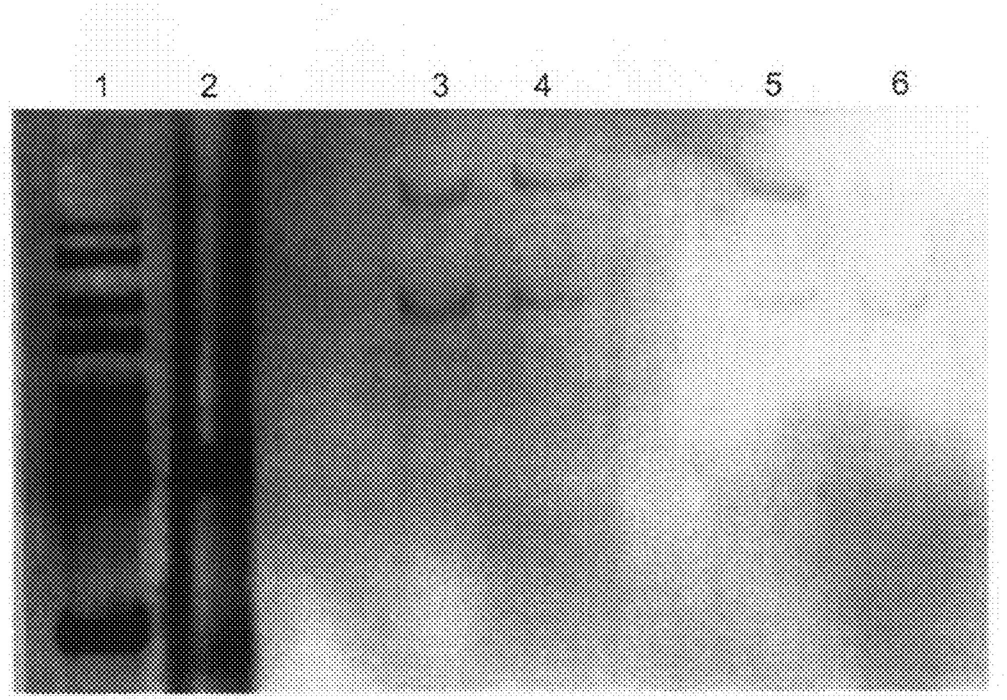
FIG. 3*a* is an autoradigram of a southern blot depicting the presence of non integrated IL-60 in plant cells; DNA was extracted from a TYLCV-infected tomato plant 1 month post injection (lane 2) and an IL-60 injected tomato plant, 2 months post injection (lanes 3-6) and hybridized with a DNA probe against a segment of the TYLCV-CP ORF (SEQ ID NO: 40); Lane 1 is a size marker; bands obtained with IL-60-BS are larger than those of TYLCV due to the insertion of plasmid; In lanes 5 and 6 DNA was cleaved with BglII prior to electrophoresis; similar size of cleaved and non cleaved DNA from IL-60 injected plants indicates that the plasmids were not integrated into the plant genome.
Figure 3B:
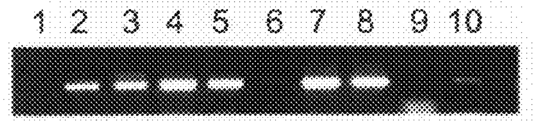
FIG. 3*b* depicts an ethidium bromide stained gel of PCR products illustrating IL-60-BS replication and movement in several plants; Lane 1: negative control (PCR without a template); Lane 9: negative control (PCR performed on DNA extracted from a non-treated tomato); Lane 2: tomato; Lane 3: tobacco; Lane 4: dill; Lane 5: wheat; Lane 6: grapevine, Lane 7: lettuce; Lane 8: squash; Lane 10: cabbage.

IL-60-BS does not integrate into the plant's genome—Total DNA was extracted from tomato leaves remote from the point of IL-60-BS injection and was analyzed for the presence of IL-60-BS by Southern blot, with a probe against the TYLCV-CP gene (FIG. 3*a*) or via PCR (FIG. 3*b*). Southern analysis was done without shearing, and with or without cleaving DNA with BglII. Two major bands were detected in samples from IL-60-BS, as well as TYLCV-infected plants (lanes 3-6, and lane 2 respectively of FIG. 3*a*). In samples from IL-60-BS administered plants (lanes 3-6 of FIG. 3*a*) the two corresponding bands were of a larger size than those of TYLCV alone, due to the presence of the plasmid. Southern blot analysis, together with PCR results, show that IL-60-BS can be found in remote tissues, a long time after the vector has been administered to the plant. Southern blot analysis is far less sensitive than PCR, therefore positive reactions in remote tissues after long time periods can not be attributed to residual, diluted DNA that had been originally administered to the plant. Since BglII does not cleave within IL-60-BS, the fact that the bands from cleaved (lanes 5 and 6 of FIG. 3*a*) and uncleaved (lanes 3 and 4 of FIG. 3*a*) samples were of the same size, indicates that the vector had not been integrated into the plant's genome. If the vector had been integrated, cleaving with BglII would have resulted in longer bands in the cleaved samples as a result of the addition of plant DNA to the detected vector DNA.

Figure 4A:
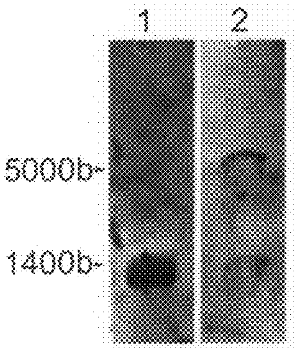
FIG. 4*a* is an autoradigram of a northern blot depicting expression of IL-60-BS in tomato plants; RNA was extracted from either TYLCV infected (SEQ ID NO: 4-lane 1) or IL-60-BS injected (SEQ ID NO: 1-lane 2) plants, and hybridized with a probe against TYLCV-CP (SEQ ID NO:41), 5 months post injection; arrows indicate the approximate size of the RNA bands.
Figure 4B:
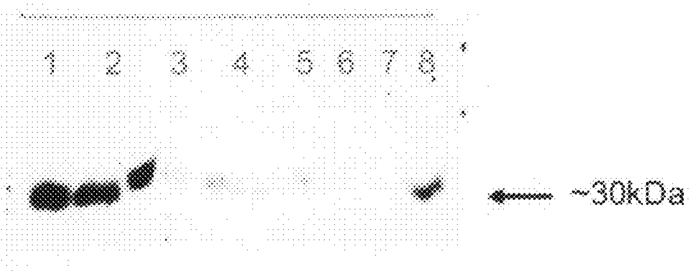
FIG. 4*b* is a western blot image depicting expression of IL-60-BS in tomato plants; protein extracts from either TYLCV-infected plant (positive control—lane 1), IL-60-BS-injected tomato plants (3 weeks post injection—lanes 2-6 and 8), or an untreated tomato plant (negative control—lane 7) were immunoblotted with antibodies against TYLCV-CP.
Figure 7:
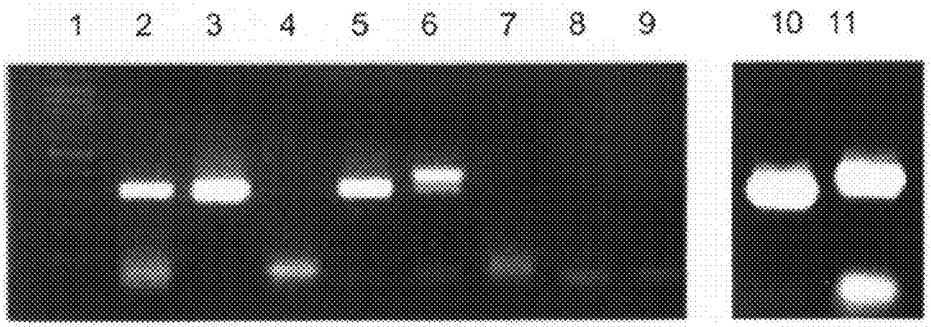
FIG. 7 depicts an ethidium bromide stained gel of PCR products illustrating that IL-60-BS is not transmitted by insects (*Bemisia tabaci*) fed on IL-60-BS-carrying tomato plants and transferred to non carrying tomato plants; DNA from the non carrying tomato plants was tested by PCR for the existence of IL-60-BS; Lane 1 is a size marker; lanes 2, 3 and 5 template DNA was extracted from the IL-60-BS-carrying source plants on which the insect were fed; lanes 7, 8, and 9: template DNA was extracted from the plants to which the insects were transferred; lane 4 template DNA was extracted from an untreated plant (negative control); lane 6 template DNA was extracted from a TYLCV-infected plant (positive control); lane 10 PCR was performed with IL-60-BS as template (positive control); lane 11 DNA was extracted from the source plant shown in lane 6 (providing evidence that TYLCV was successfully transmitted in this experiment)

Viral CP is expressed in IL-60-BS injected plants—RNA was extracted from a tomato leaf further up the point of injection, 5 months after administration of IL-60-BS. RNA samples from IL-60-BS-injected and -TYLCV infected plants were subjected to Northern blot analysis with a probe corresponding to TYLCV-CP (FIG. 4), which revealed transcription leftward from the viral bi-directional promoter [residing within the intergenic region (IR)—FIG. 1*a*]. FIG. 4*a* shows transcription of IL-60-BS (FIG. 4*a*, frame 2) and TYLCV (frame 1) viral genes. IL-60-BS RNA produced a transcript of the expected size, as well as a longer transcript, indicating that the insertion of the plasmid into the virus partially intervened with correct termination. Expression of the viral CP was also shown with Western blot analysis, using antibodies against TYLCV-CP (FIG. 4*b*), on proteins extracted from plants 3 weeks after infection with TYLCV (lane 1) or injection with IL-60-BS (lanes 2-6 and 8).

Expression of foreign genes carried on IL-60-BS—expression of GUS and GFP in plants injected with IL-60-BS-GUS and IL-60-BS-GFP respectively, was assessed by PCR using primers which amplify the reporter genes. Positive reactions with DNA templates from leaves further up from the point of injection were observed as early as 3 days post injection. FIG. 5 shows both genes were expressed, and produced active proteins, as detected by GUS staining (FIGS. 5*a-c*) and GFP fluorescence. GUS activity was followed up periodically and was persistent at least up to 12 months (FIG. 5*b*). TYLCV is a phloem-limited virus, hence GUS expression in tomato was found mostly in the vascular system. However, after a few months (in tomato) GUS activity was also noted in parenchyma cells. IL-60-BS spread also downward of the point of injection and was found in tomato roots. An example of GUS-expressing roots 12 months p.i. is shown in FIG. 5*c*.

Taken together, these results show that a non-pathogenic, mutated construct of TYLCV, which can replicate and move systemically in its host plant, has been generated. IL-60-BS and its derivatives do not integrate into the plant genome and are easily and efficiently introduced into plants, without the need for in-vitro transcription or Agroinoculation. Genes present carried by the IL-60-BS and its derivatives are expressed in plant. Expression is durable, and lasts for the whole life span of the plant, making IL-60-BS an efficient and reliable vector.

Example 2

IL-60-BS-GUS Heritability

Expression of GUS was determined with PCR and GUS staining in both IL-60-BS-GUS carrying parental plants, and their progeny as described above in methods and materials.

IL-60-BS-GUS is not heritable—while the parental plants showed positive results for retention of the IL-60-BS-GUS (FIG. 2 lane 15) in all PCR amplifications, and expressed GUS 12 months post injection, 19 out of the 20 tested progeny did not show positive results with any of the PCR amplifications (part of the progeny tested is given in FIG. 6) and did not express GUS. Parental plant and controls are shown in FIG. 2 (parental plant—lane 15).

Geminiviruses are not seed-transmissible [Kashina, B. D., et al., Phytoparasitica 31, 188-199 (2003)]. Analysis of GUS-expressing plant progeny indicated that the cloned trait is not maternally inherited. The single occasion where weak GUS expression was noted in a progeny plant (lane 2 in FIG. 6) is probably due to "mechanical" vector contamination of the seed cortex, which infected the emerging shoot of the plant, as is the case with several viruses (e.g. Tomato mosaic virus—Hadas, R. et al., Phytoparasitica 32, 421-424 (2004)]

The BIM-LAB instrument (BIO-OZ Biotechnologies Ltd. Yad-Mordechai, Israel) can deliver IL-60-BS to several hundred plants per day and the BIM-TEN instrument (BIO-OZ Biotechnologies Ltd. Yad-Mordechai, Israel) to over 500,000 seedlings per day. This makes large-scale introduction of an external trait to plants at the nursery, safe, feasible and easy. A crop carrying the new trait in a non-transgenic manner can thus be safely grown in the field, with no risk transmission to unwanted seeds, making the present invention the potential method of choice for the safe introduction of new traits to important crops which, otherwise, could hardly be manipulated.

Example 3

IL-60-BS Transmissibility

Transmission of IL-60-BS by *B. tabaci* was tested by PCR of DNA from plants exposed to insects previously exposed to plasmid carrying plants Wild TYLCV is transmitted by the whitefly, *Bemisia tabaci*. To test whether the viral vector is also transmitted through a viral natural transmitter, plants carrying the IL-60-BS vector were fed to *B. tabaci*. Insects were then transferred to tomato plants that do not carry the vector, and transmission of the vector was assessed with PCR. Results show that plants to which insects were transferred did not carry the IL-60-BS vector. These results further substantiate the ability of the present invention to serve as a safe vector for introduction of new traits to selected plants, without succumbing to the risk of these traits being transferred to other less desired plants.

Example 4

Replication and Spread of Ampicillin-deleted IL-60-BS and IL-60-BS-GUS

IL-60-BS$^{amp-}$ and IL-60-BS-GUS$^{amp-}$ administered to tomato plants, were assessed for replication and expression using PCR analysis and GUS activity.

Figure 8A:
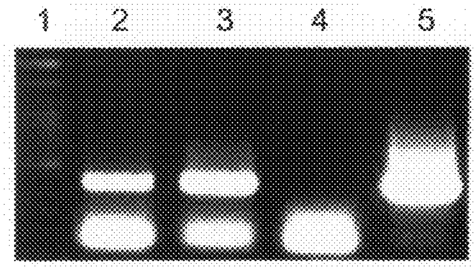
FIG. 8*a* depicts an ethidium bromide stained gel of PCR products illustrating propagation of IL-60-BS$^{amp-}$ in plants; DNA was extracted 10 days post-injection and PCR was performed with primers specific to IL-60; Lane 1 is a size marker; lanes 2 and 3 template DNA was extracted from plants injected with IL-60-BS$^{amp-}$; lane 4 template DNA was extracted from an untreated plant (negative control); lane 5 template DNA was IL-60-BS (positive control)
Figure 8B:
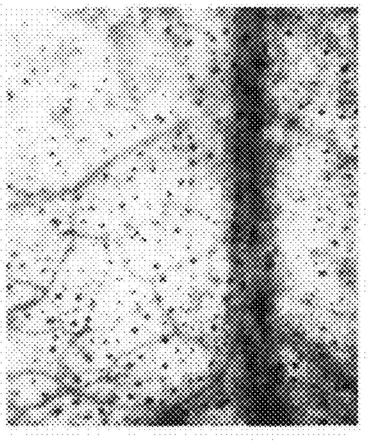
FIG. 8*b* is a photomicrograph of GUS expression in a tomato plant injected with IL-60-BS-GUS$^{amp-}$.

The administration of IL-60-BS into plants is very efficient (over 90%); therefore selection for successful transfection is not required. This allowed the removal of the ampicillin-resistance (amp) gene from the vector. Removal of the ampicillin resistance gene eliminates any possibility of horizontal transmission of the amp gene, which is a significant public safety concern. IL-60-BS$^{amp-}$ and IL-60-BS-GUS$^{amp-}$ were injected to tomato plants. PCR indicated their replication within 3 days p.i. (FIG. 8*a*) and GUS activity was noted 7-10 days later (FIG. 8*b*).

The system described hereinabove, which can be easily administered to large scale crops, without the use of a selectable marker, answers all requirements for a safe and environmentally friendly vector.

Example 5

Trans-activation of a Reporter Gene Placed Adjacent to IR by a Disarmed Helper Component Expression of GUS was determined with PCR and GUS staining in plants administered with either IR-GUS-pD alone, or co-administered with either IL-60-BS, wild type TYLCV or BdMV.

Figure 1B:
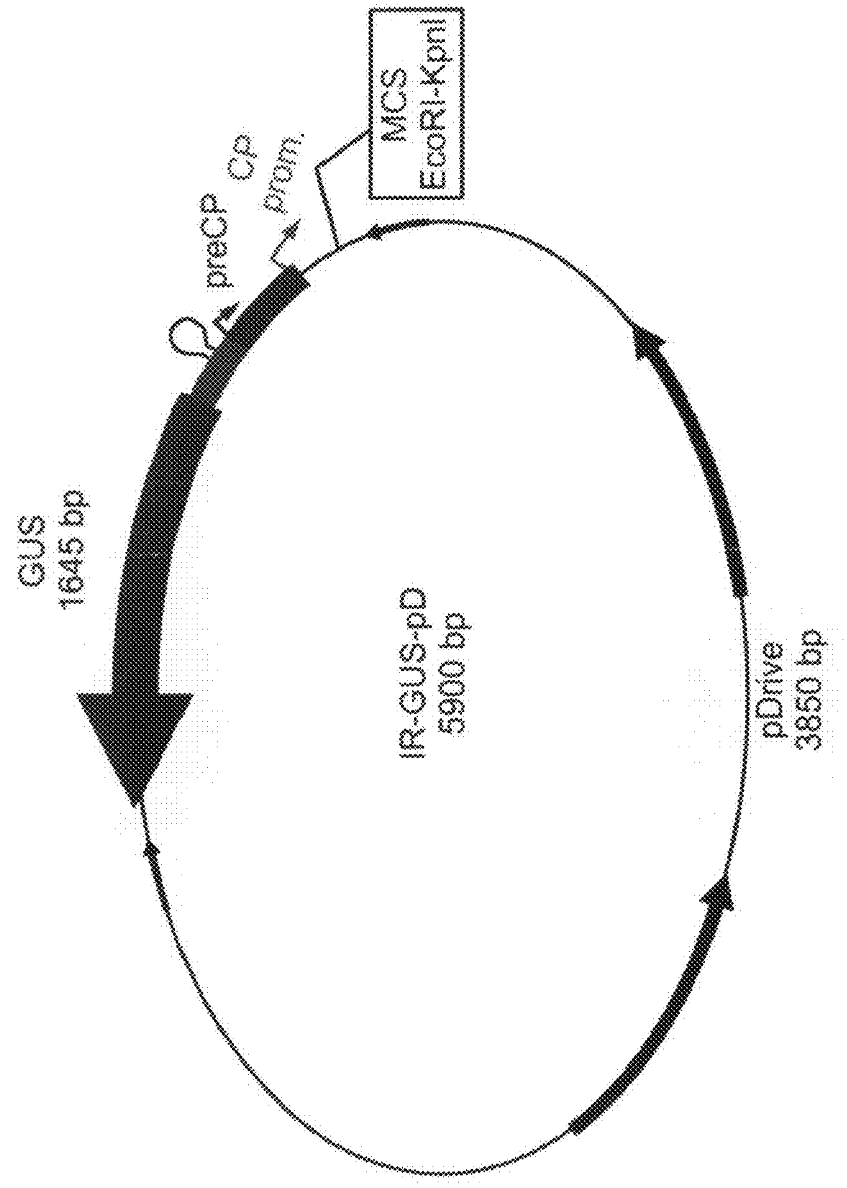
FIG. 1*b* is a map of nucleic acid construct; IR-GUS-pD (SEQ ID NO: 13); a GUS gene was ligated leftward of a truncated IR and a truncated pre-CP ORF; TYLCV-derived sequences were inserted into the plasmid pDRIVE.
Figure 9A:
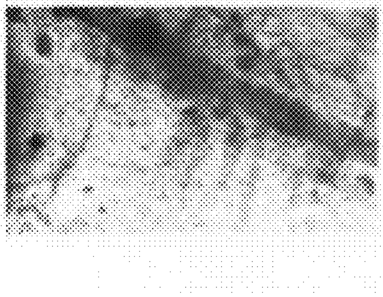
FIGS. 9*a*-9*i* are photomicrographs depicting induced expression of GUS in various plants, following transactivation of IR-GUS-pD by IL-60-BS 3 days (FIGS. 9*b* and 9*c* and 9*h*), and 14 days post injection (all other panels): tomato (*Lycopersicon esculentum*.
Figure 9B:
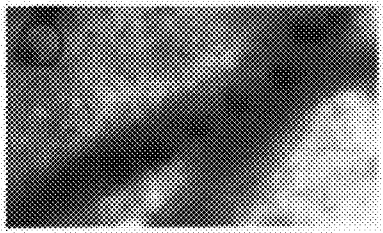
Figure 9C:
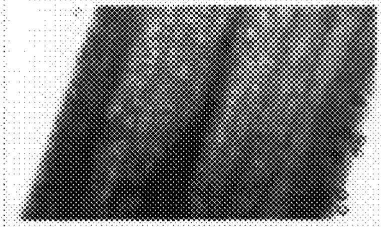
Figure 9D:
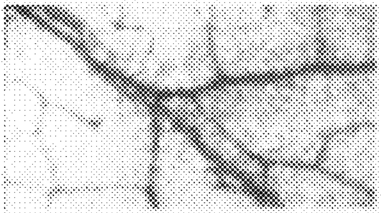
Figure 9E:
Figure 9F:
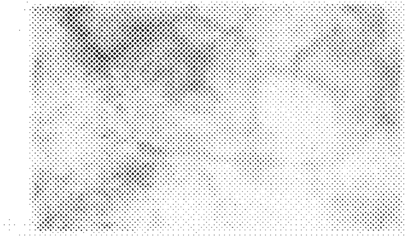
Figure 9G:
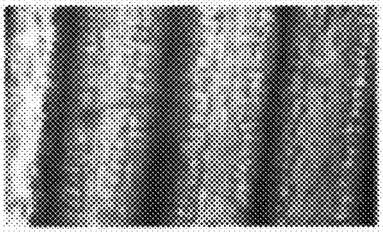
Figure 9H:
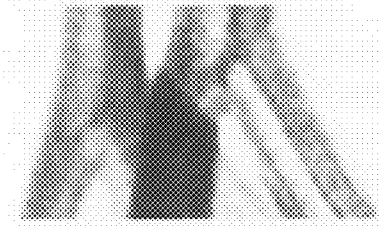
Figure 9I:
Figure 9J:
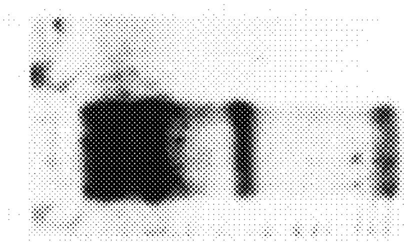
FIG. 9*j* is an autoradigram of a southern blot of DNA was extracted from a tomato plant injected with IR-GUS-pD and IL-60-BS and hybridized with a probe against GUS (SEQ ID NO: 41)
Figure 9K:
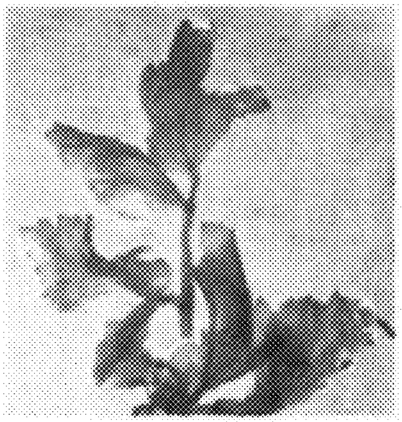
FIGS. 9*k*, 9*l*, 9*m* and 9*n* are macroscopic photographs of GUS-expressing plants: a whole parsley plantlet (FIG. 9*k*), a whole tomato leaf (FIG. 9*l*), a whole onion leaf (FIG. 9*m*) and a whole wheat leaf (FIG. 9*n*)

Expression of IR-GUS-pD using IL-60-BS as a helper component—IR-GUS-pD (FIG. 1*b*) was propagated in *E. coli*, but could not, by itself, replicate in tobacco or tomato plants. However, co-administration of IL-60-BS and IR-GUS-pD resulted in replication of both vectors (as indicated by Southern blot analysis-FIG. 9*j*). Strong expression of GUS in these plants was also noted, as determined by GUS staining.

Figure 9L:
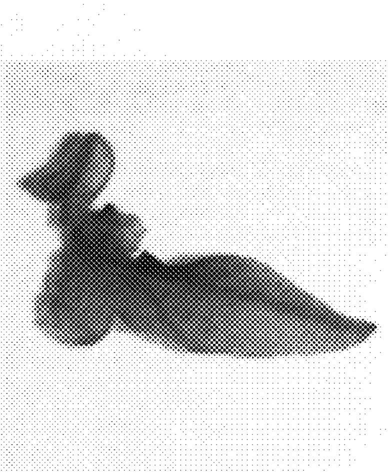
Figure 9M:
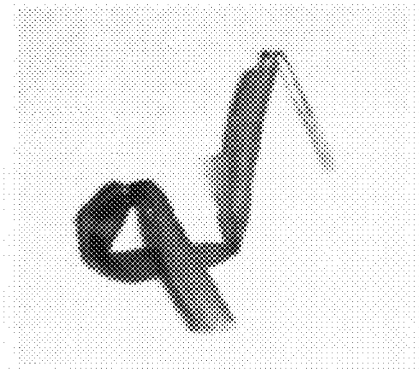
Figure 9N:
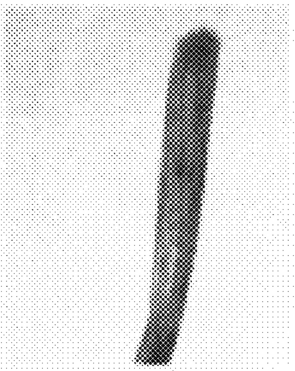
Figure 10:
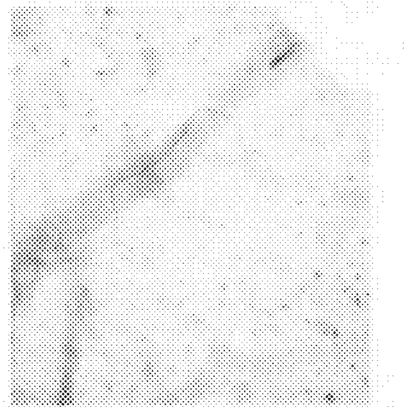
FIG. 10 is a photograph showing induced expression of GUS by IR-GUS-pD following injection of a tomato plant with IL-60-BS 14 days following administration of the IR-GUS-pD construct.

FIGS. 9*k*, 9*l*, 9*m* and 9*n* are macroscopic photographs of GUS-expressing plants: a whole parsley plantlet (FIG. 9*k*), a whole tomato leaf (FIG. 9*l*), a whole onion leaf (FIG. 9*m*) and a whole wheat leaf (FIG. 9*n*);

Inducible Expression of IR-GUS-pD by TYLCV and by IL-60-BS—Plants injected solely with IR-GUS-pD did not express GUS. After fourteen days the plants were challenged with a wild-type TYLCV, and extensive GUS expression was noticed within a few days, but the plants developed severe disease symptoms. However, the disarmed IL-60-BS is able to transactivate a TYLCV-IR controlled gene in a harmless manner as shown by the transactivation of IR-GUS-pD by IL-60-BS (FIG. 10). Results show that an IR-carrying segment of TYLCV fused to a foreign gene and introduced to plants is stable, even though it does not spread in the plant. Its stability may be attributed to its inherent IR sequence. A helper Geminivirus maybe introduced at a later time contributing trans-activating factors engendering the spread of and expression from the IR-carrying segment. If the helper component is IL-60-BS, the outcome is harmless to the plant. This provides an inducible expression system. It also seems that double-injection of IR-GUS-pD together with IL-60-BS brings about a stronger and quicker expression of the foreign gene.

Partial host-range of plants expressing GUS following co-administration of IL-60-BS together with IR-GUS-pD—The host range of TYLCV is quite wide—but limited. IL-60-BS together with IR-GUS-pD were applied to several plants from various botanical families including TYLCV host and non-host plants. Solanaceae, Cucurbitaceae, Umbelliferae, Liliacae, Gramineae (Poaceae), Rosaceae, Musaceae, Vitaceae and Cruciferae]. Tomato (*Lycopersicon esculentum*), tobacco (*Nicotiana tabacum*), petunia (*Petunia hybrida*), cabbage (*Brassica oleracea*), lettuce (*Lactuca sativa*), summer squash (*Cucurbita pepo*), onion (*Allium cepa*), parsley (*Petroselinum crispum*), wheat (*Triticum durum*), rose (*Rosa Hybrida*), banana (*Musa acuminata*), grapevine (*Vitis vinifera*) and dill (*Antheum graveolens*) were injected with IL-60-BS together with IR-GUS-pD, and GUS expression was determined by staining (FIGS. 6*a-i*) show GUS staining results of several of the plants mentioned hereinabove), as well as by PCR, using primers which amplify GUS (FIG. 6*k*). GUS expression was observed in all of the plants injected. In several of them, expression outside of the vascular system was strongly noted, and exceeded GUS expression outside the vascular system when IL-60-BS-GUS was administered (see Example 1 and FIG. 5). TYLCV is a phloem-limited virus, hence GUS expression in tomato was found mostly in the vascular system. However, after a few months (in tomato) GUS activity was also noted in parenchyma cells. When plants were injected with IL-60-BS together with IR-GUS-pD, GUS activity spread outside of the vascular system was much quicker and was noticed in parenchyma cells within 4 weeks from injection. In general, GUS expression was observed within 3 days in several plants (tomato, tobacco, dill) while some other plants required longer periods (up to 2 weeks) before GUS expression was noted.

All the plants tested, including monocots ornamentals and fruit trees were compliable to the vector. In particular, the essential wheat plant was also found to be compatible with the vector, thus opening a wide range of possibilities for the safe expression of various genes in this, and other vital crop plants.

Example 6

Silencing by Co-administration of IL-60-BS and an IR-pD Plasmid Expressing a Tandem Sequence (IR-PDSinvert-pD)

Figure 11A:
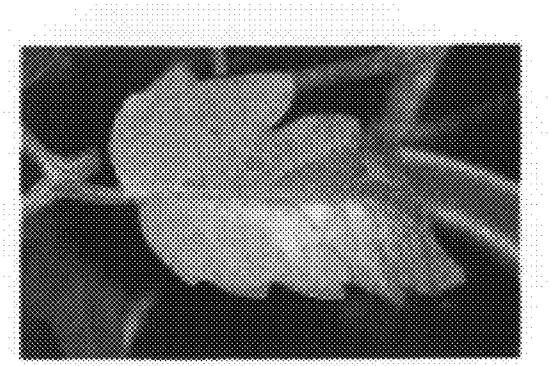
FIGS. 11*a-d* are photographs illustrating effect of silencing of the PDS gene (involved with chlorophyll synthesis) by co-administration of IL-60-BS and IR-PDSinvert-pD on leaf morphology.
Figure 11B:
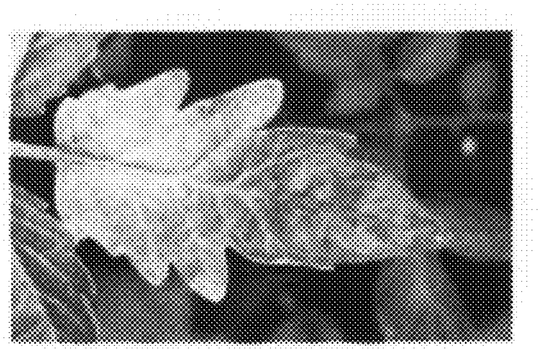
Figure 11C:
Figure 11D:
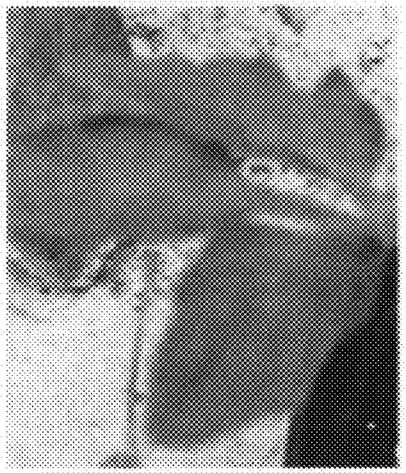

In order to demonstrate gene silencing using exemplary vectors according to the invention, co-administration of IRpD and IL-60-BS, a sequence which causes silencing of the PDS gene (involved in chlorophyll biosynthesis) was inserted into the IR-pD vector, and the resulting IR-PDSinvert-pD (2.5 μg in 30 μl) was co-administered along with IL-60-BS to tomato plants. Four week later discoloring of the leaves was noted (FIG. 11*a*). Five weeks after injection the whole leaf turned yellow (FIG. 11*c*).

Example 7

IL-60-BS does not Integrate into the Plant Genome

In order to confirm that IL-60 based constructs do not integrate into the genome of infected plants, total DNA was extracted from tomato leaves remote from the point of IL-60-BS injection and was subjected to Southern-blot analysis without cleaving or shearing. The membranes were reacted with a DIG-labeled probe corresponding to part of the TYLCV-CP gene (FIG. 12).

Two major bands were detected, as is the case with TYLCV (positive control; lane 2). In samples from leaves of IL-60-administered plants, the two corresponding bands were of a larger size than those of TYLCV alone, due to the presence of the plasmid. Southern analysis is far less sensitive than PCR and therefore, positive reactions in remote tissues after long periods cannot be attributed to residual, dilute samples of the DNA originally administered to the plant.

Figure 12:
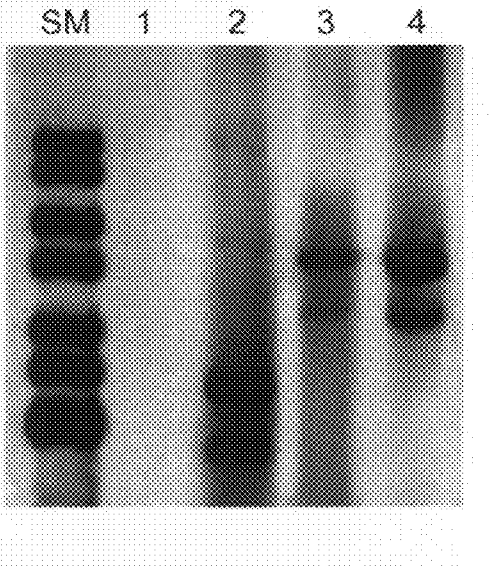
FIG. 12 is an autoradiogram of a Southern-blot analysis of DNA extracted from TYLCV-infected tomato plants and from plants injected with IL-60-BS (2 months post-injection); the blot was probed with a PCR product of a segment of the TYLCV-CP ORF; DNA extracts were: size markers (SM), DNA extract from a healthy tomato (Lane 1), DNA extract (uncleaved) from TYLCV-infected tomato (lane 2), DNA extracts (uncleaved) from IL-60-BS-injected tomatoes (lane 3), DNA extracts (BglII-cleaved) from IL-60-BS-injected tomatoes (lane 4). In lanes 3 and 4, DNA was extracted 30 days post-injection.

FIG. 12 depicts results of a Southern-blot analysis of DNA extracted from TYLCV-infected tomato plants and from plants injected with IL-60-BS (2 months post-injection). The probe was a PCR product of a segment of the TYLCV-CP ORF. The DNA extracts in the various lanes were: size markers (SM), DNA extract from a healthy tomato (Lane 1), DNA extract (uncleaved) from TYLCV-infected tomato (lane 2), DNA extracts (uncleaved) from IL-60-BS-injected tomatoes (lane 3), DNA extracts (BglII-cleaved) from IL-60-BS-injected tomatoes (lane 4).

BglII does not cleave within IL-60-BS. If the vector had been integrated into the plant's genome, then cleavage with BglII would have resulted in bands longer than those in the uncleaved samples. The bands obtained from cleaved and uncleaved samples were of the same size (FIG. 12), indicating that the vector had not been integrated into the plant genome. These results confirm those presented in Example 1.

Example 8

Viral Genes are Expressed in IL-60-BS-Injected Plants In order to confirm expression of viral genes from IL-60 based constructs after injection, RNA was extracted from a tomato leaf further up from the point of injection, 5 months after administration of IL-60-BS.

Figure 13:
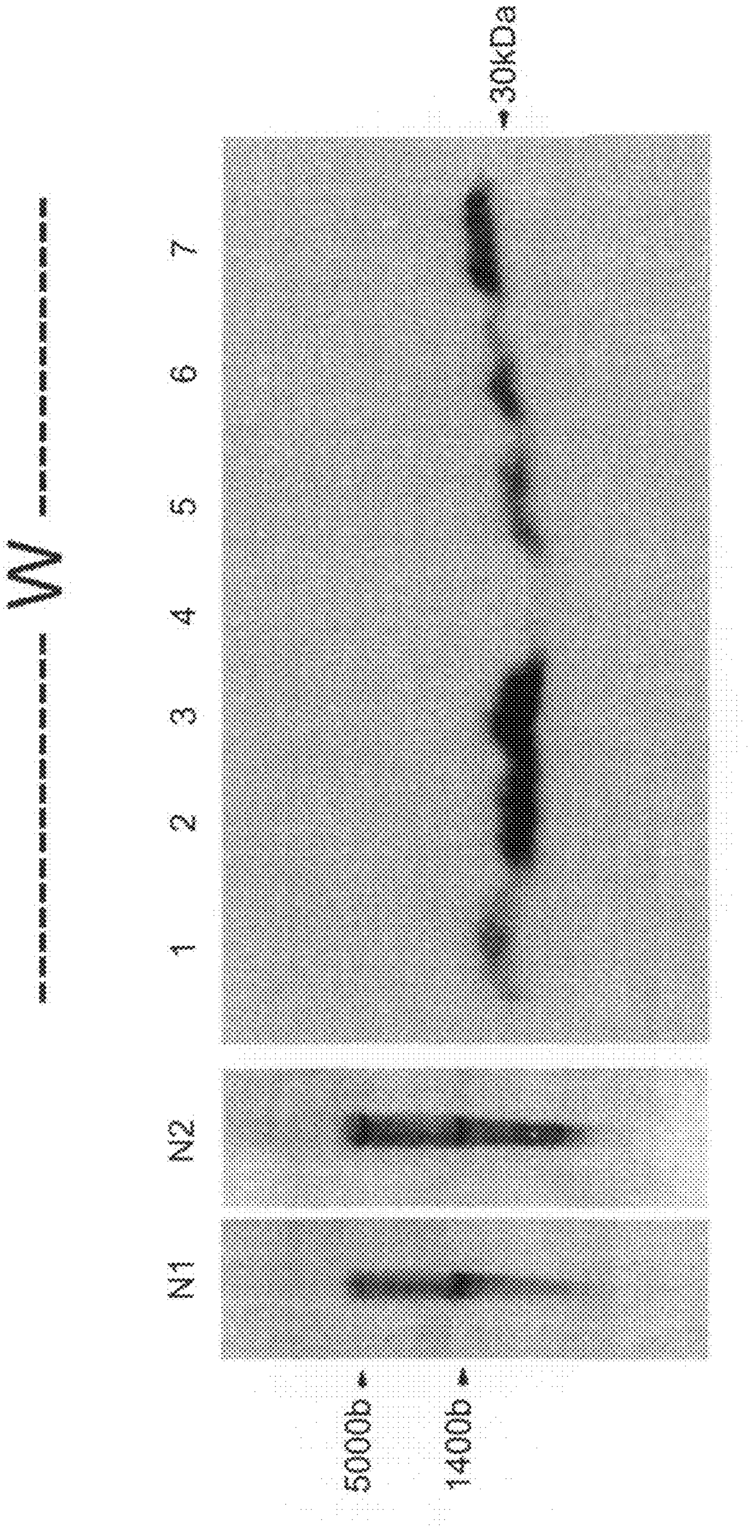
FIG. 13 comprises northern and western blot analyses illustrating expression of IL-60-BS in tomato plants; N1 and N2 are autoradiograms of northern-blots probed with the ORF of TYLCV-CP; N1: RNA from IL-60-BS-injected plants; N2: RNA from TYLCV-infected plants; approximate size of RNA bands is indicated on left; W: western-blot analysis with antibodies to TYLCV-CP; Lane 3: protein extract from a TYLCV-infected plant (positive control); Lane 4: protein extract from an untreated tomato plant (negative control); lanes 1, 2, 5, 6 and 7: protein extracts from IL-60-BS-injected tomato plants (3 weeks post-injection); Western-blot analysis of proteins extracted from IL-60-BS-carrying plants (FIG. 3) indicated expression of the viral CP.

The RNA was subjected to northern-blot analysis, and reacted with a probe corresponding to TYLCV-CP. Since all TYLCV genes are transcribed from the same bi-directional promoter (residing within the IR), the probe revealed only transcription leftward of the IR. FIG. 13 shows that transcription of IL-60-BS occurred, producing a transcript of the expected size, as well as a longer one (indicating that the insertion of the plasmid into the virus partially interfered with correct termination).

Western-blot analysis of proteins extracted from IL-60-BS-carrying plants (FIG. 13) confirmed viral CP expression at the protein level.

FIG. 13 depicts expression of IL-60-BS in tomato plants at both the RNA and protein levels. Panes N1 and N2 are northern-blots probed the ORF of TYLCV-CP. N1 depicts\RNA from IL-60-BS-injected plants and N2 depicts RNA from TYLCV-infected plants. The approximate size of the RNA bands is indicated by arrows.

A western blot (indicated as W in FIG. 13) probed with antibodies to TYLCV-CP confirmed expression of CP at the protein level. Lane 3 depicts a protein extract from a TYLCV-infected plant as a positive control. Lane 4 depicts protein extract from an untreated tomato plant as a negative control. Lanes 1, 2, 5, 6 and 7 depict protein extracts from IL-60-BS-injected tomato plants prepared 3 weeks post-injection.

These results confirm those presented in example 1.

Example 9

Foreign Genes Inserted in IL-60-BS are Expressed in Plants

In order to confirm expression of heterologous genes in the IL-60-BS, IL-60-BS-GUS and IL-60-BS-GFP were introduced into tomato plants. Replication of the constructs was monitored by PCR using primers of the reporter genes (167/408 for GUS and 345/895 for GFP; see table 1. Positive reactions with DNA templates from leaves further up from the point of injection were observed as early as 3 days p.i. (data not shown). GUS activity was detected by staining (Jefferson et al. (1987) *EMBO J.* 6, 3901-3907) and GFP by fluorescence Blumenthal et al. (1999) *Plant Science* 142, 93-99).

FIG. 14 comprises a series of photographs demonstrating IL-60-BS-derived expression of reporter genes in tomato plants. FIG. 14A shows expression of GUS in tomato 1 month post-injection (p.i.). FIG. 14B shows expression of GUS in tomato 12 months p.i. FIG. 14C shows GUS expression in tomato root 12 months p.i.

Figure 14A:
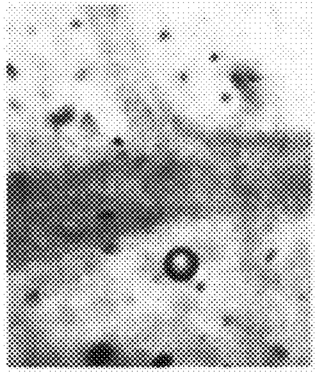
FIGS. 14*a* to 14*c* are photographs illustrating IL-60-BS-derived expression of GUS in tomato plants.
Figure 14B:
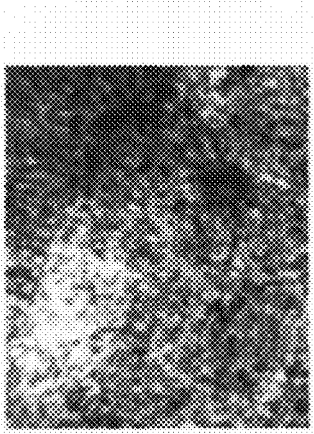
Figure 14C:
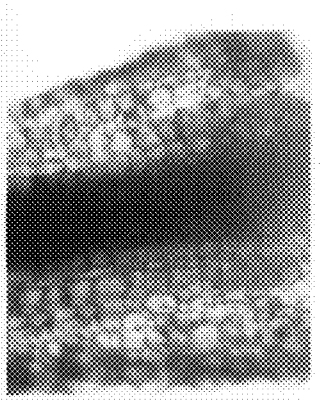
Figure 14D:
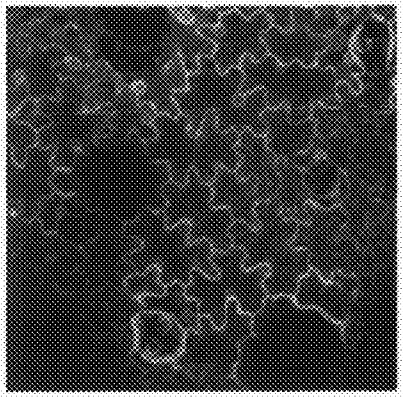
FIGS. 14*d* to 14*g* are photographs illustrating IL-60-BS-derived expression of GFP.
Figure 14E:
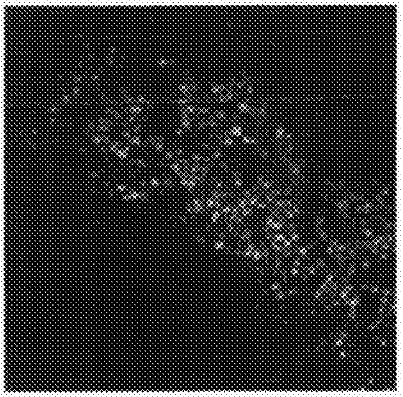
Figure 14F:
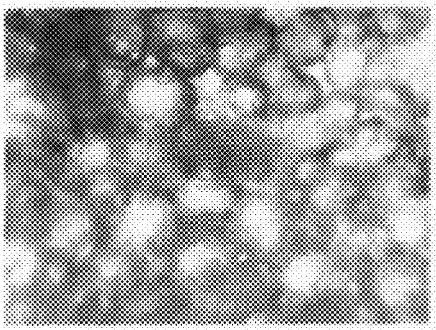
Figure 14G:
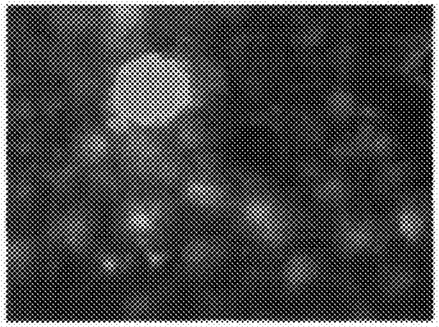

FIG. 14D is provided for comparison and shows transgenic tobacco expressing GFP under control of the 35S promoter. FIG. 14E shows expression of GFP from IL-60-BS. 3 weeks p.i. (images 14D and 14E were photographed through a fluorescence binocular). FIG. 14F and FIG. 14G show IL-60-BS-driven GFP fluorescence in *N. benthamiana* leaf tissue as seen in a dark-field inverted microscope. Image in frame G was programmed to show GFP fluorescence in green.

These results show that IL-60 based vectors can provided expression levels of downstream genes comparable to that available from the 35S plant promoter.

TYLCV is a phloem-limited virus so it is not surprising that reporter gene expression from IL-60 based vectors in tomato was initially observed in the plant's vesicular system (FIG. 14A). However, the vector gradually spread to mesophyll cells (FIGS. 14B and 14E-14G), and eventually throughout the entire plant (FIG. 14C and FIG. 9*l* hereinabove). Surprisingly, in some plants (e.g. wheat, onion and dill), expression of reporter genes was detectable outside the vesicular system almost immediately following injection of the vector.

The GFP construct employed in this series of experiments carried a leader peptide directing the gene product to the cytoplasmic endoreticulum. As expected, GFP was confined to the cytoplasm in the control 35S transgenic plants (FIG. 14D).

In sharp contrast, GFP expressed by the IL-60-based vector appeared to be secreted into the cell's vacuole (FIGS. 14 E to 14G).

Results presented in FIG. 14 show that both GUS and GFP reporter genes were expressed and produced active proteins.

GUS activity was followed up periodically and persisted for at least 12 months (data not shown).

These results confirm the results of example 1.

Example 10

Exemplary Biotechnologapplication Engendering Viral Resistance and/or Disease Recovery The IL-60 vector system can produce stable expression in plants but is transmitted vertically (i.e. to progeny via seeds) or horizontally via insect vectors. These properties suggest that the vector is well suited to use in commercial agricultural biotechnology. One example of such an ag-biotech application is protection against viruses. Protection against viruses can be implemented as either a prophylactic anti-infection measure or a curative remedy for infected plants. This example presents one strategy for protection against TYLCV, which is a commercially important plant pathogen. This illustrative example makes use of the fact that post-transcriptional gene silencing has been reported to play a role in the plant's reaction to infection.

Specifically, In the case of TYLCV, the product of ORF C4 has been reported to be the viral-silencing suppressor (Bisaro (2006) *Virology* 344, 158-168). This recent finding suggested engendering non-transgenic resistance/tolerance by silencing C4, thereby arresting the virus's ability to exercise counter-silencing measures.

Figure 1E:
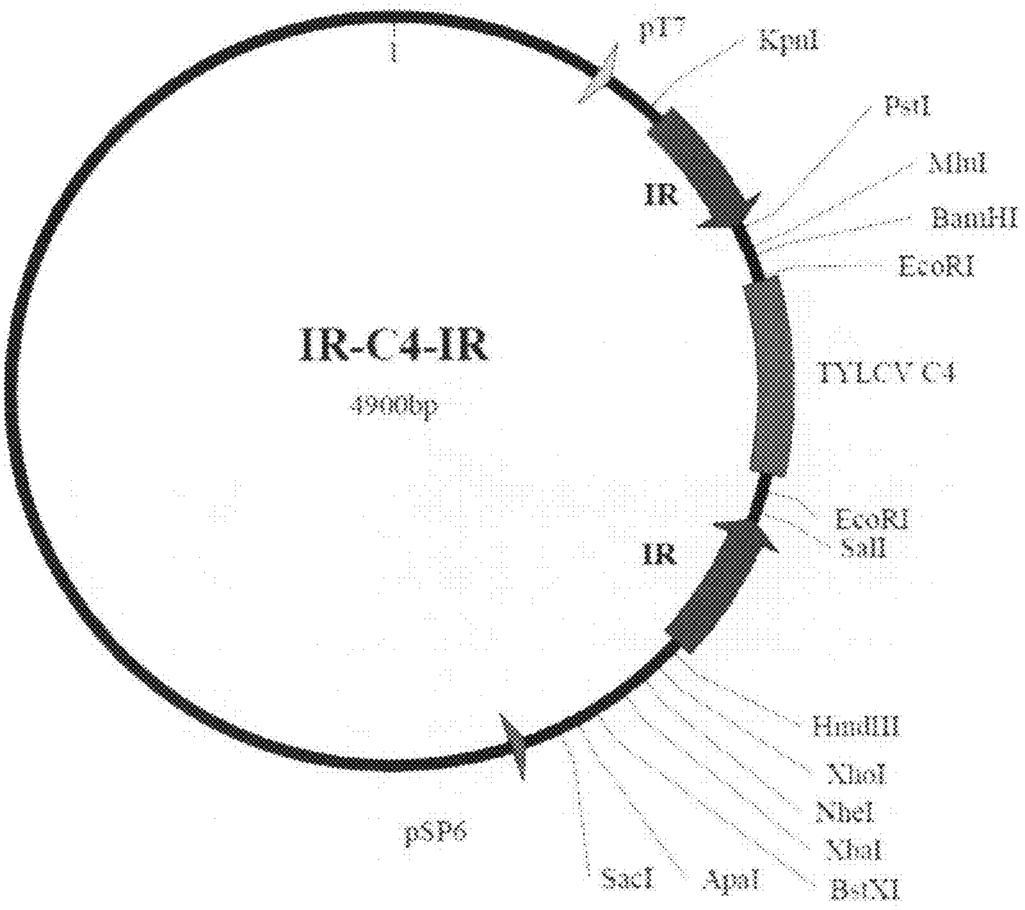
FIG. 1*e* is a map of nucleic acid construct IR-C4-IR; indicating ORF C4 of TYLCV inserted between two opposing IR promoters.

In order to silence C4, the C4 ORF was placed between two opposing IR promoters to produce the IR-C4-IR construct (FIG. 1*e*), as described hereinabove, and injected into tomato plants. This construct cannot replicate in the plant, but by virtue of its inherent IR, can be induced by the invading virus to replicate, move and be expressed. The expressed dsRNA form of C4 is expected to initiate the silencing of C4-carrying transcripts. In the absence (or presence of reduced levels) of C4, the virus can no longer suppress its own silencing by the host plant, and resistance (or tolerance) results.

Tomato seedlings were injected with IR-C4-IR (2 μg/plant). Seven days later, these plants, as well as their control, non-injected counterparts, were whitefly-inoculated with TYLCV (placing 30 viruliferous insects per plant). Sixty days post-inoculation, all of the control plants exhibited severe symptoms, while the IR-C4-IR-treated plants showed only very mild or no symptoms. Determination of the virus titer by quantitative PCR indicated a reduction of viral DNA (over a million-fold) in the C4-silenced non-symptomatic plants. Development of resistance was detected, by quantitative PCR and Southern blot analyses, as early as 1 week post-inoculation (data not shown). Furthermore, recovery from infection was obtained following injection of IR-C4-IR into plants which had already been heavily infected (inoculated in the laboratory or collected in the field). The results of the engendered resistance/tolerance are shown at both phenotypic and molecular levels in FIG. 15.

Figure 15A:
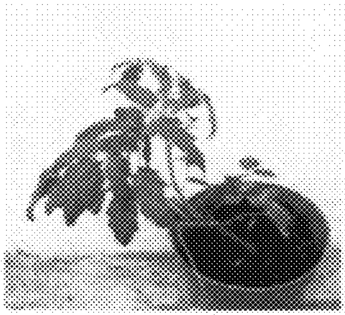
FIGS. 15*a* to 15*f* are photographs of plants illustrating TYLCV resistance/tolerance obtained by C4 silencing according to an exemplary embodiment of the invention.
Figure 15B:
Figure 15C:

FIGS. 15A and 15B depict injected with IR-C4-IR 7 days prior to TYLCV inoculation. The plant in frame FIG. 15C is a TYLCV-infected control, not treated with IR-C4-IR. Pictures were taken 30 days post-inoculation. FIG. 15A shows a symptomless resistant plant, and FIG. 15B shows a plant with mild symptoms.

Figure 15D:
Figure 15E:
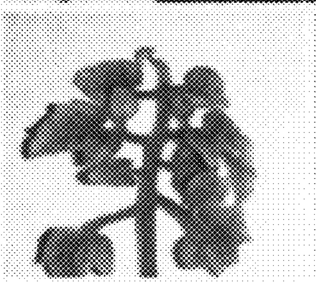
Figure 15F:
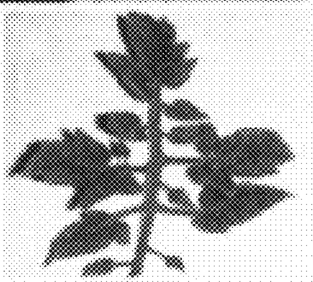

FIGS. 15D, 15E and 15F show an example of recovery. The plant shown in FIG. 15D was injected with IR-C4-IR 3 months after TYLCV inoculation. New growth of the heavily infected plant was symptomless. Specifically, the plant overcame stunting and produced flowers and normal-looking fruit.

FIG. 15E shows symptomatic leaves of the lower part of the plant of FIG. 15D which grew prior to IR-C4-IR injection.

FIG. 15F shows symptomless leaves from the upper part of the plant of FIG. 15D which grew after IR-C4-IR injection.

FIGS. 15 G and 15 H illustrate the reduction in virus titer at the molecular level in resistant and recovered plants using quantitative PCR with TYLCV-CP primers.

Figure 15G:
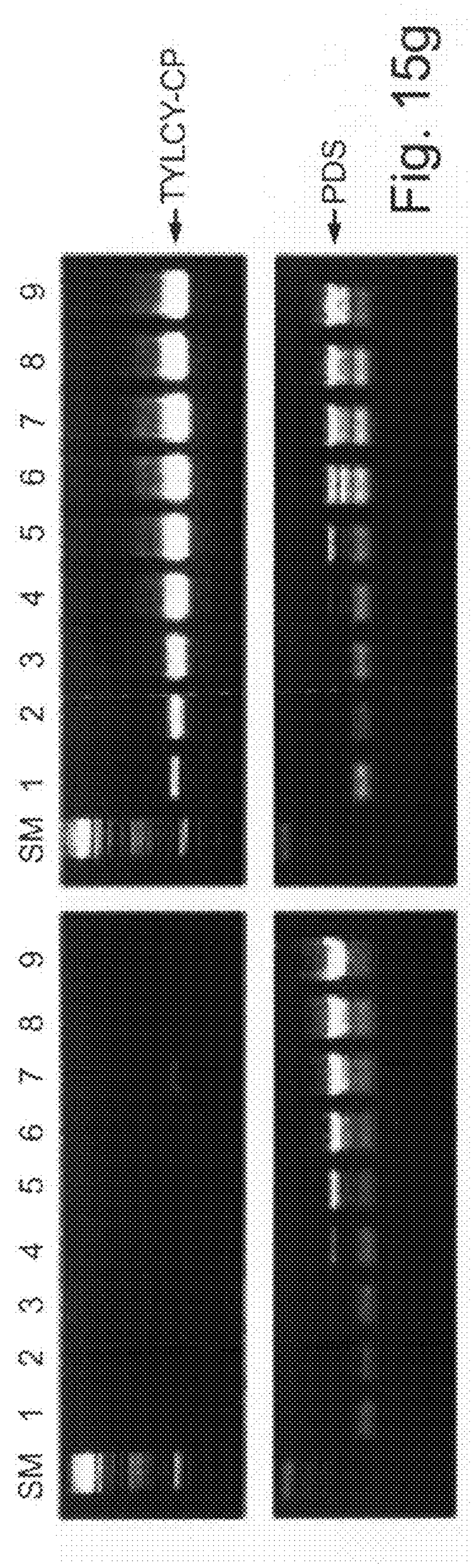
FIGS. 15*g* and 15*h* are ethidium bromide stained gels of products of quantitative RT-PCR with TYLCV-CP primers demonstrating a reduction in virus titer in resistant and recovered plants.

FIG. 15G shows PCR products with DNA of the IR-C4-IR treated plant of FIG. 15A (upper left) and the untreated plant of FIG. 15CC (upper right), following 18 to 34 PCR cycles (3 cycle intervals; lanes 1-9 in each gel). The lower frames show the results obtained with the same DNA similarly amplified with primers for the constitutive gene PDS as a loading control. In the various experiments a reduction of virus titer of approximately 250,000 to 16-million fold was obtained in IR-C4_IR plants compared to untreated control. When an already-infected plant was treated with IR-C4-IR the titer in leaves emerging after treatment compared to those existing before treatment was about 100,000-fold less.

Figure 15H:
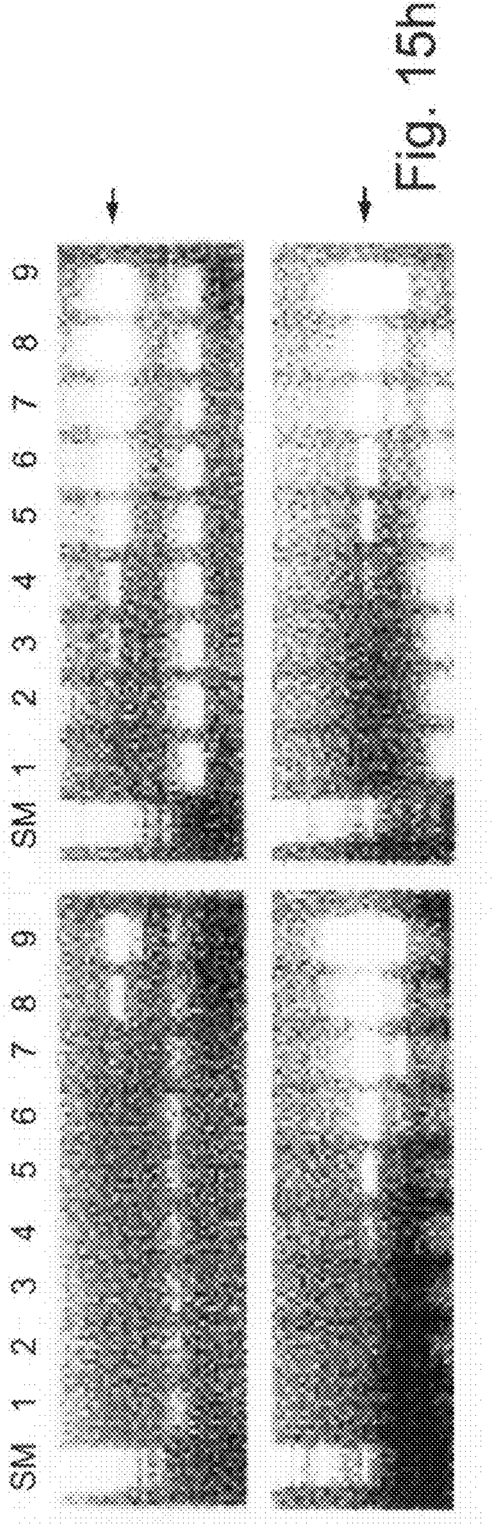

FIG. 15H shows the results of a similar quantitative PCR experiment conducted on DNA extracted from the recovered upper leaves (upper left frame) and symptomatic lower leaves (upper right frame) of the plant of FIG. 15D. Loading controls are and conditions are as in FIG. 15G.

Results presented in this example demonstrate that viral vectors according to exemplary embodiments of the invention can prevent viral infection and/or reduce viral titer in infected plants. Reduction of titer is sufficient to significantly reduce and/or eliminate viral symptoms.

Example 11

Comparative Quantification of the Level of Expression in IL-60 Systems Cis vs Trans Activation It was visually observed that co-administration of IL-60-BS and IR-GUS-pD (or IR-GFP-pD) to activate a gene on the IR-PD helper virus in trans produced higher levels of expression than the same reporter genes expressed directly from IL-60-BS in cis.

In order to confirm this visual observation, levels of reporter gene expression resulting from IR-GUS-pD and IR-GFP-pD co-administered with IL-60-BS were tested quantitatively (see METHODS) relative to their expression in transgenic plants driven by the strong plant promoter 35S. In both cases, IL-60-derived expression was comparable to that of 35S-derived expression. Expression levels of the different tested cases were approximately 0.25- to 2-fold those in the control transgenic plants. The actual rates for GUS, obtained by the MUG assay (fluorescence units/μg protein/hour) were 3.7 for 35S-derived expression in tobacco, 2.9 for IL-60-derived expression in *N. benthamiana,* 0.9 in petunia and 6.6 in onion. The rates for GFP (fluorescence units per cell) were 1.67 for 35S-GFP and 1.81 for IR-pD-GFP co-injected with IL-60-BS (both in tobacco). As described hereinabove, the intracellular localization of the expressed protein in the transgenic plants differed from that in the IL-60-treated plants.

These results indicate that the vector system comprising IL-60-BS and an IR-heterologous gene-IR-pD construct provide an alternative to transgenic plant generation which offers comparable, sometimes superior, expression levels of the heterologous gene when compared to the 35S transgenic expression system.

Example 12

Corroboration of Silencing by RT PCR

In order to corroborate results of silencing of PDS observed photypically and described above in Example 6, quantitative RT-PCR of plants expressing IR-PDSinvert-pD under the control of IL-60-BS was performed. *N. benthamiana* plants were tested.

Figure 16:
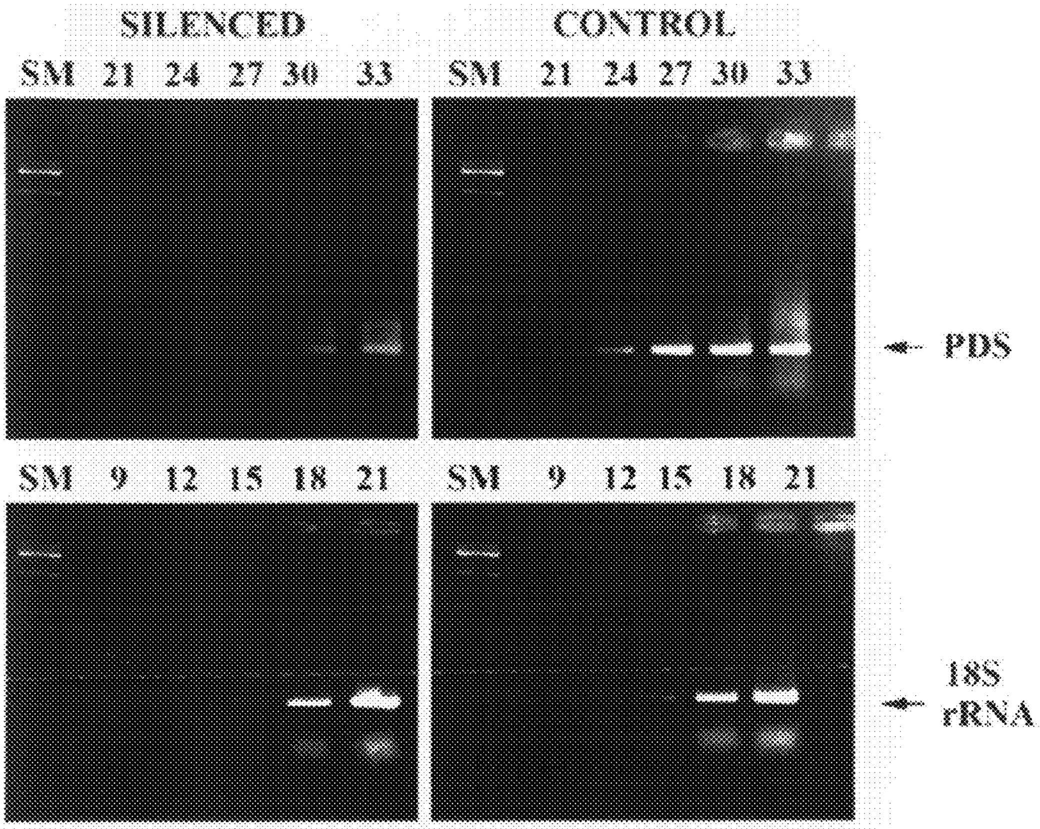
FIG. 16 are ethidium bromide stained gels of products of a quantitative RT-PCR assay corroborating the silencing phenomenon represented phenotypically in tomato plants depicted in FIG. 11 hereinabove; SM: size markers; for other lanes, numbers above each lane represent cycle number, top two frames show the results obtained from control and silenced plants respectively; a PCR product first appears at cycle 21 in the control, and at cycle 30 in the silenced plant; two bottom frames represent results obtained following amplification of 18S ribosomal RNA from the same plants; in both cases, a PCR product was first noticed at cycle 15.

FIG. 16 presents ethidium bromide stained gels of PCR products. SM indicates size markers. The numbers above each lane represent cycle number. The top two frames show the results obtained from the control and silenced plants as indicated. A PCR product first appears at cycle 21 in the control, and at cycle 30 in the silenced plant. This indicates a suppression of about 512 fold ($2^9$).

The two bottom frames represent results obtained following amplification of the 18S ribosomal RNA from the same plants as a loading control. In both cases, a PCR product was first noticed at cycle 15. These results indicate that loading was substantially equivalent.

Overall, results presented in FIG. 16 provide molecular confirmation for the phenotypic indication of PDS silencing described in Example 6.

Example 13

Corroboration of Replication of IL-60-BS$^{amp-}$ in Plants

In order to corroborate results presented in Example 4, PCR was performed on DNA from a series of tomato plants infected with IL-60-BS$^{amp-}$ using appropriate primers (SEQ ID NOs.: 16 and 17).

Figure 17:
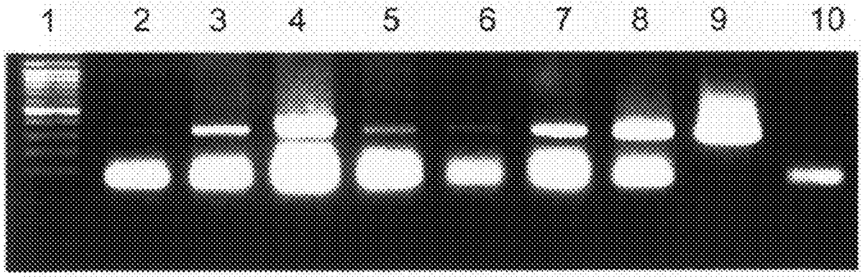
FIG. 17 is an ethidium bromide stained gel of PCR products from reaction with primers that differentiate between IL-60 and TYLCV (SEQ ID NOs,: 16 and 17) demonstrating that IL-60-$BS^{amp-}$ replicates in plants; Lane 1: size markers; Lane 9: positive control with IL-60-BS template; Lane 10: negative control with DNA extracted from untreated tomato plant; Lanes 2-8: DNA extracted from various tomato plants injected with IL-60-$BS^{amp-}$ (3 weeks post-injection)

FIG. 17 is an ethidium bromide stained gel of PCR products. Size markers appear in lane 1. In lane 9 the template DNA was IL-60-BS (positive control). In lane 10: template DNA was extracted from an untreated tomato plant (negative control). Lanes 2-8 comprise PCR products from DNA extracted from various tomato plants injected with IL-60-BS$^{amp-}$ (3 weeks post-injection).

These results corroborate this presented hereinabove in Example 4 and FIG. 8*a*.

Example 14

IL-60-BS Replicates in Plants Independent of Origin if Replication

In order to demonstrate that IL-60-BS replicates in plant cells independent of the bacterial origin of replication, a construct in which the plasmid's origin of replication (ORI) as described in METHODS was prepared. The ORI deleted construct was injected into *N. benthamiana* plants.

Figure 18:
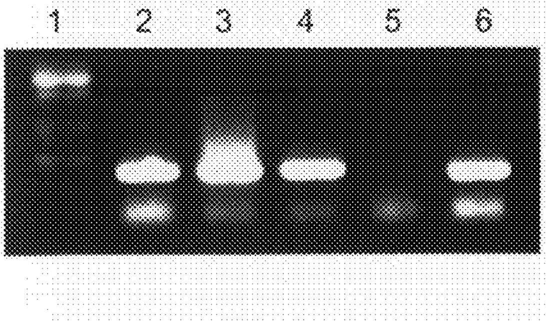
FIG. 18 is an ethidium bromide stained gel of PCR products from reaction with primers that differentiate between IL-60 and TYLCV (SEQ ID NOs,: 16 and 17) demonstrating that IL-60-BS devoid of ColE1 replicates in plants; Lane 1: size markers; Lane 2: positive control with DNA extracted from an IL-60-BS-injected tomato plant; Lane 3: positive control with IL-60-BS DNA; Lane 5: negative control with DNA extracted from an untreated plant; Lanes 4 and 6: DNA extracted from tomato plants injected with ORI-less IL-60-BS (4 weeks post-injection)

FIG. 18 is an ethidium bromide stained gel of PCR products (primers SEQ ID NOs.: 16 and 17) demonstrating deletion of ORI does not prevent plasmid replication in plants. Size markers are presented in Lane 1. Results from template DNA extracted from an IL-60-BS-injected tomato plant are presented as a positive control in lane 2. Results from IL-60-BS template DNA are presented in lane 3 (additional positive control) Lane 5 presents results from template DNA extracted from an untreated plant as a negative control. Lanes 4 and 6 present results from template DNA extracted from tomato plants injected with ORI-less IL-60-BS (4 weeks post-injection).

Results of Examples 13 and 14 clearly demonstrate that removal of the amp-resistance gene (ca. 1000 bp) and/or the ORI (ca. 700 bp) from the plasmid do not interfere with vector replication and/or movement in plants. However, these portions of the vector an be important in shuttling between plants and bacteria and/or as a spacer interrupting the viral rep gene.

Removal of the ORI results in a construct which cannot replicate in bacterial cells. In an exemplary embodiment of the invention, a vector which cannot replicate in bacterial cells contributes to a reduction in concern about possible vector escape to plant or soil bacteria.

Example 15

Induction of Vector by Insect Transmitted TYLCV

In order to demonstrate that wild type TYLCV transmitted by an insect vector can induce expression of a vector in trans, IR-PDSinvert-pD was injected into tomato plants. Three days following injection the plants were insect-inoculated with TYLCV. Bleaching was noticed 3 weeks after inoculation (prior to the appearance of viral symptoms).

Figure 19:
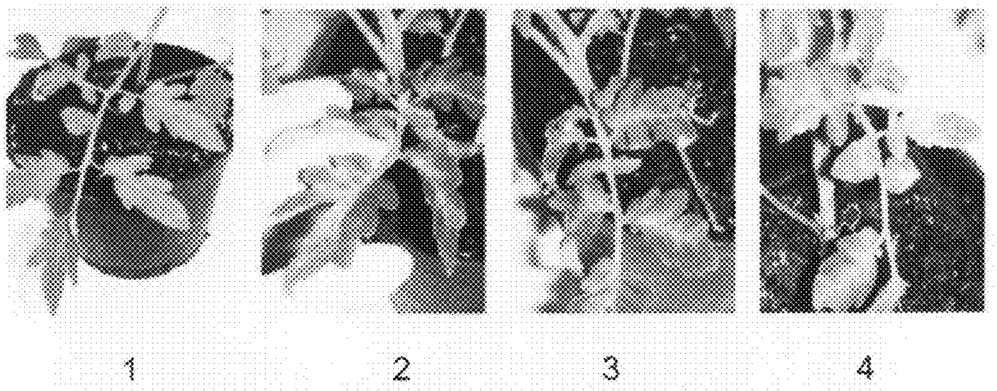
FIG. 19 is a series of photographs depicting tomato plants injected with a construct comprising a segment of the tomato gene for PDS (bases 937-1035 of GenBank accession no. M88683) inserted between two opposing IRs (replacing C4 in FIG. 1*e*) and then insect-inoculated with TYLCV three days subsequently; bleaching is apparent prior to the appearance of viral symptoms at 3 weeks after inoculation in plants 2, 3 and 4; plant 1 was injected with IR-PDS-IR but not inoculated with TYLCV and exhibits no bleaching.

FIG. 19 is a series of photographs depicting: (1) A control plant (injected with IR-PDS-IR but not inoculated with TYLCV); and (2, 3 and 4) plants injected with IR-PDS-IR and inoculated with TYLCV.

These results demonstrate the capacity of exemplary vectors according to embodiments of the invention to respond to viral infection prior to the onset of viral symptoms in infected plants. Optionally, this strategy can be employed to limit economic effects of viral infection in the field. In an exemplary embodiment of the invention, an exemplary vector according to the invention is activated by viral infection and a translation product from the exemplary vector kills only those leaves infected by the virus. Optionally, this occurs before the virus can spread systemically through the plant.

Example 16

Expression of an Entire Operon

In order to demonstrate that exemplary vectors according to the invention can be used to express multigene operons, the entire PRN operon (as a single piece carrying all 4 genes) of *P. fluorescence* (corresponding to bases 424-6165 of GenBank accession # U74493; SEQ ID No.: 49) in place of GUS in IR-GUS-pD (FIG. 1*b*) The resultant plasmid, pIR-PRN, was injected into tomato or bean plants along with IL-60-BS (each construct injected at 5 µg/plant). The constructs were injected into tomato sterns, or into swelled bean seeds.

Figure 20:
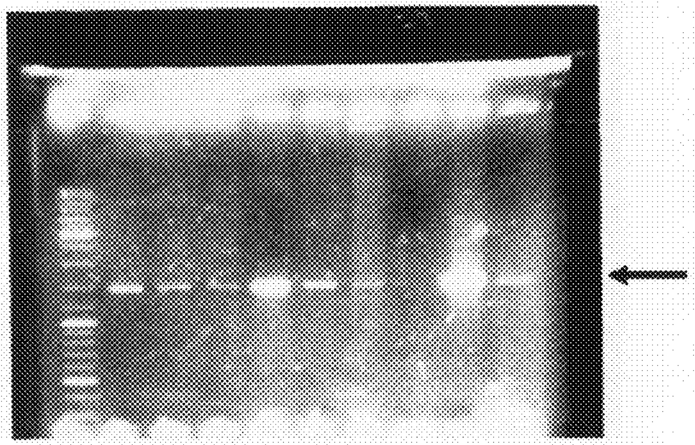
FIG. 20 depicts an ethidium bromide stained gel of PCR products of tomato DNA extracted 7 days post injection with pIR-PRN+IL-60-BS; Primers detecting the gene prn-C (gcgaacgaacacgatagcaa and cgtcaatgagggcgtgaa; SEQ ID NOs.: 49 and 50 respectively) were used for amplification; arrow indicates an amplified band of 1463 bp; Lane 1 is loaded with size markers; lanes 2 to 10 each show PCR products from an extract of a different pIR-PRN+IL-60-BS injected plant.

FIG. 20 is an ethidium bromide stained gel of PCR products of tomato DNA extracted 7 days post injection with pIR-PRN+IL-60-BS. SEQ ID NOs.: 47 and 48 (gcgaacgaacacgatagcaa and cgtcaatgagggcgtgaa; respectively) were employed as primers for detection of prn-C DNA An arrow at the right indicates an amplified band of 1463 bp corresponding to prn-C. DNA samples were extracted from non injected leaves. Lane 1 is loaded with size markers and lanes 2 to 10 each show PCR products from an extract of a different pIR-PRN+IL-60-BS treated plant.

PCR results indicate the presence of PRN operon in leaves remote from the point of injection, confirming systemic spread of the vectors throughout the plant. These results confirm results of similar experiments conducted with IL-60-BS and other IR-pD constructs.

Example 17

Expression of prn Operon in Plants Imparts Resistance to Fungal Infection

In order to demonstrate that overexpression of the prn operon in plants can impart resistance to bacterial infection plants were injected with pIR-PRN and IL-60-BS. Plants were challenged by inoculation with *Rhyzoctonia solani* seven days after injection. Uninjected plants served as controls.

Figure 21:
FIG. 21 is a photograph of a pair of plants providing an example of PRN-engendered resistance to *Rhyzoctonia solani*; the plant on the left has not been treated while the plant on the right has been injected with pIR-PRN+IL-60-BS 7 days prior to inoculation with *R. solani*; Pictures were taken 4 days after inoculation with *Rhyzoctonia solani;*

FIG. 21 is a photograph depicting an uninjected tomato plant on the left and a pIR-PRN and IL-60-BS injected plant on the right. The picture was taken four days after inoculation with *R. solani*. The uninjected plant is wilted and dying as a result of the bacterial inoculation.

Figure 22:
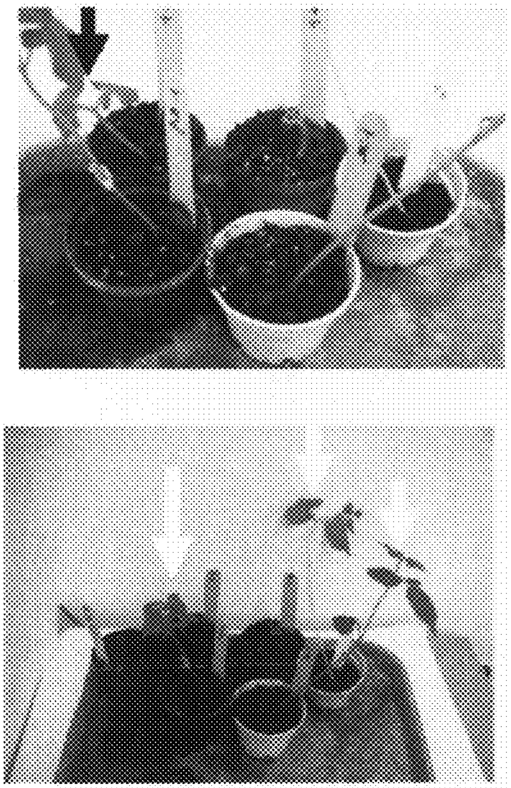
FIG. 22 is a pair of photographs of bean plants from seeds injected with pIR-PRN+IL-60-BS (indicated by arrows) and untreated seeds (no arrows) after inoculation with *Rhyzoctonia solani*; pictures were taken 4 days after germination (6 days after injection)

FIG. 22 is a pair of photographs of bean plants from seeds injected with pIR-PRN+IL-60-BS (indicated by arrows) and untreated seeds (no arrows) after inoculation with *Rhyzoctonia solani*. Fungal infection was by placing seeds in soil infested with the fungus. Plants germinating from seeds injected with pIR-PRN+IL-60-BS are clearly more robust than the untreated plants. Pictures were taken 4 days after germination (6 days after injection of seeds).

This example clearly demonstrates the protective effect of prn overexpression using exemplary vectors according to an embodiment of the invention to protect against fungal challenge.

Example 18

In Vitro Assay of prn Protective Effect

In order to demonstrate that antifungal products of the prn operon are distributed throughout the plant, samples of discs cut out of tomato stems following inoculation with *R. solani* were placed in small (5 cm) culture plates with PDA (potato dextrose agar) at 28° C. Fungus infection, as determined by spread of mycelium, was detected every day for 2 weeks.

Figure 23:
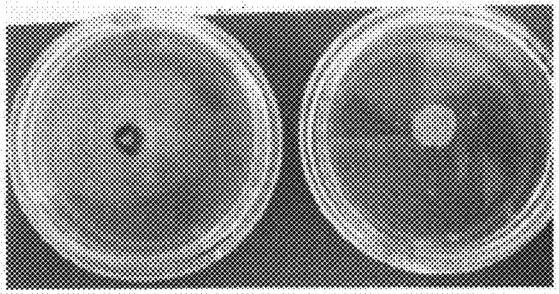
FIG. 23 is a photograph of stem discs from *Rhyzoctonia*-infected tomato plants incubated on potato dextrose agar (PDA); left dish contains a plant disc from untreated plant and exhibits significant spread of mycelium; right dish contains a plant disc from pIR-PRN-treated plant and exhibits no significant spread of mycelium.

FIG. 23 is a photograph of the stem discs from *Rhyzoctonia*-infected tomato plants incubated on PDA. The left dish contains a plant disc from an untreated plant and exhibits significant spread of mycelium. The right dish contains a plant disc from pIR-PRN-treated plant and exhibits no significant spread of mycelium;

Mycelia developed within a day in plates with *Rhyzoctonia*-inoculated untreated plant discs, but did not develop in plates with discs from *Rhyzoctonia*-inoculated during two weeks.

These results confirm that the protective material was distributed throughout the plant.

Example 19

Isolation of an Antifungal Product from pIR-PRN and IL-60-BS Infected Plants

In order to demonstrate that the antibacterial effect described in examples 17 and 18 is associated with a metabolic product of the prn operon, plant extracts were prepared and analyzed by thin layer chromatography.

Plant extracts were prepared from three grams of tomato plant stem tissue from plants pre-injected with pIR-PRN+IL-60-BA by homogenization in 10 ml of ethyl acetate, filtering through cheesecloth to remove crude debris, and evaporation in the cold to produce a dry residue. The dry residue was dissolved in 100 μl of acetonitrile.

Aliquots of the plant extract were analyzed by thin-layer chromatography (TLC). Samples were applied to TLC plates covered with silica gel (SIL G25, Macherey-Nagel GmbH, Düren, Germany) and chromatographed in chloroform: methanol (19:1). After drying PRN was visualized by spraying with Ehrlich Reagent (2 g p-dimethylaminobenzolaldehyde in 10 ml ethanol and 10 ml HCl).

Figure 24:
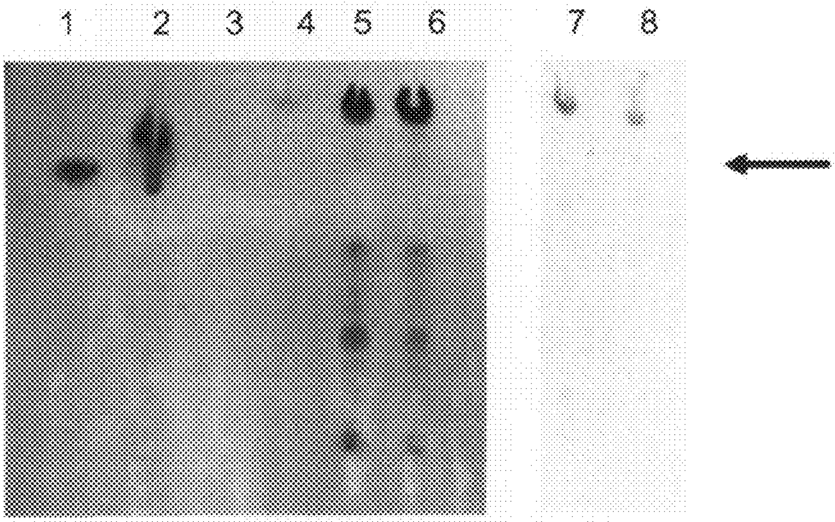
FIG. 24 is a photograph of silica gel TLC plates developed with Ehrlich reagent analysis for PRN; lane 1: PRN standard (Sigma Aldrich; St Louis Mo.; USA); Lane 3: empty; lanes 2 to 6 contain extracts from pIR-PRN-treated plants; Lane 2 (50 μl); Lane 4 (2 μl); Lane 5 (10 μl); Lane 6 (10-μl of extract from a different pIR-PRN-treated plant); Lanes 7 and 8: 10 μl of extracts from untreated plants; arrow indicates position of PRN.

FIG. 24 is a photograph of silica gel TLC plates developed with Ehrlich reagent as described above. Lane 1 was loaded with a PRN standard (Sigma Aldrich; St Louis Mo.; USA) and lanes 2 to 6 contain different volumes of extract from pIR-PRN-treated plants; Lane 2 (50 μl); Lane 4 (2 μl); Lane 5 (10 μl; Lane 6 (10 μl of extract from a different pIR-PRN-treated plant). Lanes 7 and 8 were loaded with extracts from untreated plants 10 μl. Lane 3 was left empty. An on the right indicates position of PRN.

Results presented in FIG. 24 indicate that a reactive substance of the same mobility as that of a commercially-obtained PRN standard was found in pIR-PRN-treated plant extracts and not in extracts of untreated plants. These results suggest that the TLC characterized substance was responsible for the antifungal activity described in example 18.

Example 20

Antifungal Activity of Extracts of pIR-PRN-Treated Tomato Plants

In order to demonstrate that the prn identified in plant extracts is biologically active, extracts prepared as described in Example 19 were applied to Petri dishes of PDA inoculated with *Botrytis* spp. and incubated for 30 hours at 28° C.

Figure 25:
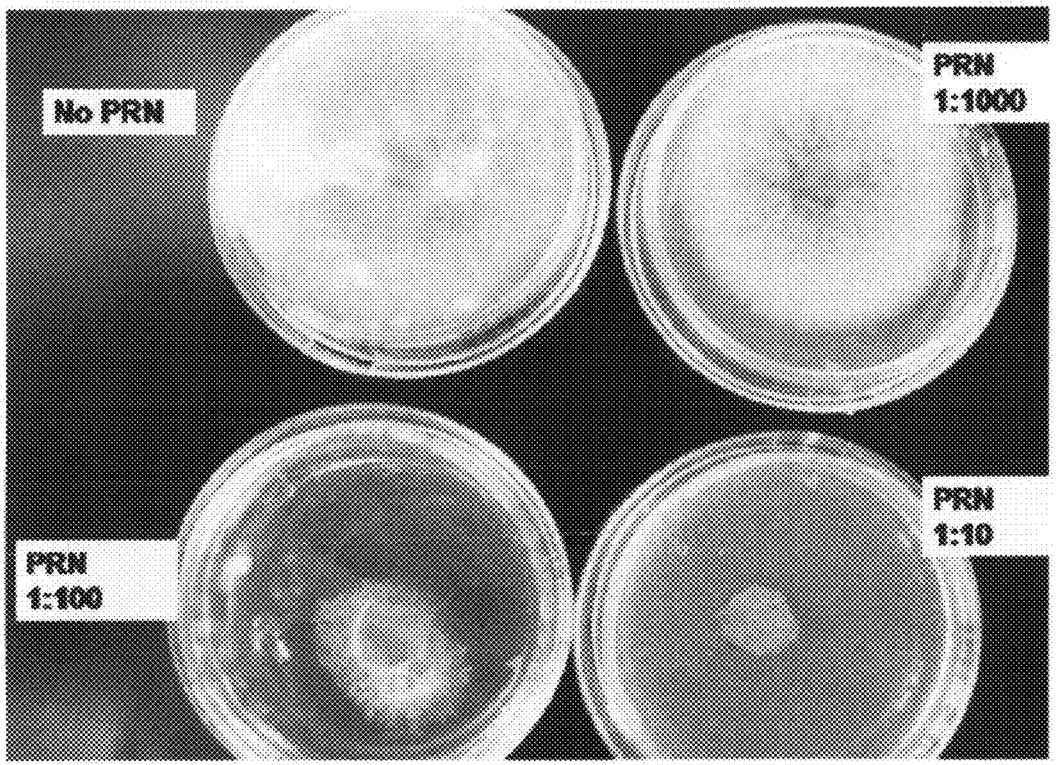
FIG. 25 is a photograph of Petri dishes of PDA inoculated with *Botrytis* spp. and incubated for 30 hours at 28° C.; upper left plate was spotted with 50 μl of acetonitrile ("no PRN"); serial dilutions of 50 μl PRN plant extract were applied to the growing medium in other dishes as indicated.

FIG. 25 is a photograph of the Petri dishes inoculated with *Botrytis* spp. The upper left plate was spotted with 50 μl of acetonitrile ("no PRN"; negative control) Remaining plates were spotted with serial dilutions of 50 μl of a PRN plant extract. Dilutions are indicated next to each dish.

It is clear from FIG. 25 that extracts from plants expressing the PRN operon inhibited fungal growth in a concentration dependent manner while an extract from un-treated plant did not inhibit fungal growth.

Results presented in Examples 17 to 20 indicate that plants treated with pIR-PRN+Il-60-BS produce an antibacterial/antifungal substance that co-migrates with synthetic PRN in a TLC assay. Demonstrated ability of the plant-produced PRN (in plant tissue and plant extracts) to inhibit fungal growth of *Rhyzoctonia* and *Botrytis* suggests that it is active against the full range of species that are sensitive to bacterial prn. Demonstration of the protective effect of prn produced by an exemplary vector according to the invention in both tomato and bean suggests that the vector can regulate translation of multi-gene constructs, including, but not limited to, bacterial operons in a wide range of plant species. Alternatively, or additionally, prn produced by an exemplary vector according to the invention in both tomato and bean suggests that the vector can transform a wide variety of plants into bioreactors, even for non-protein products.

Results presented in Examples 17 to 20 demonstrate feasibility of non-transgenic plant bioreactors. In addition, the exemplary embodiments of vectors described hereinabove and demonstrated in the examples are characterized by a high degree of safety. The high degree of safety results from one or more of lack of vertical transmission via seeds, lack of horizontal transmission via insect vectors, absence of selectable markers, inability to replicate in bacteria and expression only via induction.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

According to exemplary embodiments of the invention, geminivirus sequences described as providing a specific functional activity can be replaced by shorter, or different, geminivirus sequences which provide the functional activity, optionally at a higher or a lower level.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A tomato yellow leaf curl virus (TYLCV) Geminivirus based expression construct comprising a polynucleotide sequence encoding:

(i) a TYLCV coat protein (CP) having a deletion in nucleotides encoding an N-terminal 100 amino acids of said CP, wherein said deletion results in a deletion in the C terminus of the TYLCV V2 protein; and (ii) a TYLCV replicase having an insertion, wherein said insertion results in a reduced capability of rolling circle, single stranded DNA replication compared to an unmodified TYLCV replicase, and further wherein said insertion of said TYLCV replicase results in an insertion in the open reading frame of the C4 protein of said TYLCV.

2. The expression construct of claim 1, wherein the expression construct comprises a heterologous polynucleotide sequence encoding a molecule selected from the group consisting of a reporter molecule, an antiviral molecule, a viral moiety, an antifungal molecule, an antibacterial molecule, an insect resistance molecule, a herbicide resistance molecule, a biotic or abiotic stress tolerance molecule, a pharmaceutical molecule, a growth inducing molecule and a growth inhibiting molecule.

3. The expression construct of claim 1, wherein the expression construct includes a heterologous polynucleotide larger than 1 kb.

4. The expression construct of claim 1, comprising a bacterial polynucleotide sequence.

5. The expression construct of claim 1, wherein the expression construct is adapted for expression in a plant host selected from the group consisting of Solanaceae, Cucurbitaceae, Umbelliferae, Liliacae, Gramineae (Poaceae), Rosaceae, Musaceae, Vitacea, and Cruciferae.

6. The expression construct of claim 1, comprising a dysfunctional bacterial origin of replication.

7. A method of expressing a molecule of interest in a plant cell comprising introducing into the plant cell a TYLCV Geminivirus based expression construct comprising a polynucleotide sequence encoding:

(i) a TYLCV coat protein (CP) having a deletion in nucleotides encoding an N-terminal 100 amino acids of said CP, wherein said deletion results in a deletion in the C terminus of the TYLCV V2 protein: and (ii) a TYLCV replicase having an insertion, wherein said insertion results in a reduced capability of rolling circle, single stranded DNA replication compared to an unmodified TYLCV replicase, and further wherein said insertion o said TYLCV replicase results in an insertion in the open reading frame of the C4 protein of said TYLCV; and (iii) a heterologous polynucleotide sequence encoding the molecule of interest.

8. The method of claim 7, wherein said expression construct construct further includes a bacterial polynucleotide sequence.

9. The method of claim 7, wherein the molecule of interest is selected from the group consisting of a reporter molecule, an antiviral molecule, a viral moiety, an antifungal molecule, an antibacterial molecule, an insect resistance molecule, a herbicide resistance molecule, a biotic or abiotic stress tolerance molecule, a pharmaceutical molecule, a growth inducing molecule, and a growth inhibiting molecule.

10. The method of claim 7, wherein the plant cell is from a plant selected from the group consisting of a Solanaceae, a Cucurbitaceae, an Umbelliferae, a Liliacae, a Gramineae (Poaceae), a Rosaceae Musaceae, Vitacea and a Cruciferae.

11. A tomato yellow leaf curl virus (TYLCV) Geminivirus based expression construct comprising a TYLCV intergenic region (IR) polynucleotide sequence covalentiv linked to a polynucleotide sequence of interest, being devoid of a C2, C3 and replicase polynucleotide sequence, the construct being capable of systemic symptomless spread in a plant host when expressed simultaneously with the expression construct of claim 1 or a wild type TYLCV.

12. A method of expressing a polynucleotide sequence of interest in a plant cell comprising introducing into the plant cell the TYLCV Geminivirus based expression construct of claim 11, thereby expressing the polynucleotide sequence of interest.

13. The method of claim 12, further comprising inoculating the plant with a Geminivirus following said introducing.

14. The method of claim 13, wherein said Geminivirus is a wild type Geminivirus.

15. The method of claim 13, wherein said Geminivirus is a modified Geminivirus.

* * * * *